US012692552B2

(12) United States Patent
Artsiomenka et al.

(10) Patent No.: US 12,692,552 B2
(45) **Date of Patent: *Jul. 28, 2026**

(54) MICROSATELLITE INSTABILITY DETECTION IN CELL-FREE DNA

(71) Applicant: Guardant Health, Inc., Redwood City, CA (US)

(72) Inventors: Aliaksandr Artsiomenka, Mountain View, CA (US); Marcin Pawel Sikora, Burlingame, CA (US); Catalin Barbacioru, Fremont, CA (US); Darya Chudova, San Jose, CA (US); Martina I. Lefterova, Redwood City, CA (US)

(73) Assignee: GUARDANT HEALTH, INC., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/219,819

(22) Filed: May 27, 2025

(65) Prior Publication Data

US 2025/0283181 A1 Sep. 11, 2025

Related U.S. Application Data

(63) Continuation of application No. 18/500,890, filed on Nov. 2, 2023, now Pat. No. 12,344,902, which is a continuation of application No. 18/456,362, filed on Aug. 25, 2023, which is a continuation of application No. 16/907,034, filed on Jun. 19, 2020, now Pat. No. 11,773,451, which is a continuation of application No. PCT/US2019/048999, filed on Aug. 30, 2019.

(60) Provisional application No. 62/857,048, filed on Jun. 4, 2019, provisional application No. 62/823,578, filed on Mar. 25, 2019, provisional application No. 62/726,182, filed on Aug. 31, 2018.

(51) Int. Cl.
*C12Q 1/6886* (2018.01)
*G16B 20/20* (2019.01)
*G16B 30/10* (2019.01)
*G16B 40/20* (2019.01)

(52) U.S. Cl.
CPC ........... *C12Q 1/6886* (2013.01); *G16B 20/20* (2019.02); *G16B 30/10* (2019.02); *G16B 40/20* (2019.02)

(58) Field of Classification Search
None
See application file for complete search history.

(56) References Cited

U.S. PATENT DOCUMENTS

| | | | |
|---|---|---|---|
| 5,912,148 | A | 6/1999 | Eggerding |
| 6,130,073 | A | 10/2000 | Eggerding |
| 6,210,891 | B1 | 4/2001 | Nyren et al. |
| 6,258,568 | B1 | 7/2001 | Nyren |
| 6,582,908 | B2 | 6/2003 | Fodor et al. |
| 6,818,395 | B1 | 11/2004 | Quake et al. |
| 6,833,246 | B2 | 12/2004 | Balasubramanian |
| 6,911,345 | B2 | 6/2005 | Quake et al. |
| 6,969,488 | B2 | 11/2005 | Bridgham et al. |
| 7,115,400 | B1 | 10/2006 | Adessi et al. |
| 7,169,560 | B2 | 1/2007 | Lapidus et al. |
| 7,170,050 | B2 | 1/2007 | Turner et al. |
| 7,282,337 | B1 | 10/2007 | Harris |
| 7,302,146 | B2 | 11/2007 | Turner et al. |
| 7,313,308 | B2 | 12/2007 | Turner et al. |
| 7,329,492 | B2 | 2/2008 | Hardin et al. |
| 7,476,503 | B2 | 1/2009 | Turner et al. |
| 7,482,120 | B2 | 1/2009 | Buzby |
| 7,501,245 | B2 | 3/2009 | Quake et al. |
| 7,537,898 | B2 | 5/2009 | Bost et al. |
| 9,598,731 | B2 | 3/2017 | Talasaz |
| 9,902,992 | B2 | 2/2018 | Talasaz et al. |
| 10,793,916 | B2 | 10/2020 | Talasaz |
| 2001/0053519 | A1 | 12/2001 | Fodor et al. |
| 2003/0152490 | A1 | 8/2003 | Trulson et al. |
| 2011/0160078 | A1 | 6/2011 | Fodor et al. |
| 2012/0208706 | A1 | 8/2012 | Downing et al. |
| 2015/0292033 | A1 | 10/2015 | Wang et al. |

(Continued)

FOREIGN PATENT DOCUMENTS

| | | | |
|---|---|---|---|
| EP | 3601615 | A1 | 2/2020 |
| WO | 2011143656 | A2 | 11/2011 |

(Continued)

OTHER PUBLICATIONS

Lanman et al. (PLoS One Oct. 16, 2015:27 pages).*

(Continued)

*Primary Examiner* — Lori A. Clow

(74) *Attorney, Agent, or Firm* — Stephen W. Chen

(57) ABSTRACT

Provided herein are methods for determining the microsatellite instability status of samples. In one aspect, the methods include quantifying a number of different repeat lengths present at each of a plurality of microsatellite loci from sequence information to generate a site score for each of the plurality of the microsatellite loci. The methods also include comparing the site score of a given microsatellite locus to a site specific trained threshold for the given microsatellite locus for each of the plurality of the microsatellite loci and calling the given microsatellite locus as being unstable when the site score of the given microsatellite locus exceeds the site specific trained threshold for the given microsatellite locus to generate a microsatellite instability score, which includes a number of unstable microsatellite loci from the plurality of the microsatellite loci.

15 Claims, 12 Drawing Sheets

Specification includes a Sequence Listing.

(56) References Cited

U.S. PATENT DOCUMENTS

| | | | |
|---|---|---|---|
| 2016/0326597 | A1 | 11/2016 | Chan et al. |
| 2017/0198351 | A1 | 7/2017 | Lee et al. |
| 2017/0213008 | A1 | 7/2017 | Venn |
| 2017/0313775 | A1 | 11/2017 | Diaz et al. |
| 2017/0327567 | A1 | 11/2017 | Skokos et al. |
| 2017/0327590 | A1 | 11/2017 | Lowy et al. |
| 2018/0080068 | A1 | 3/2018 | Kamps-Hughes et al. |
| 2019/0023787 | A1 | 1/2019 | Diaz et al. |
| 2019/0169685 | A1 | 6/2019 | Georgiadis et al. |

FOREIGN PATENT DOCUMENTS

| | | | |
|---|---|---|---|
| WO | 2015103037 | A2 | 7/2015 |
| WO | 2016077553 | A1 | 5/2016 |
| WO | 2016081947 | A2 | 5/2016 |
| WO | 2017151502 | A1 | 9/2017 |
| WO | 2017151517 | A1 | 9/2017 |
| WO | 2017151524 | A1 | 9/2017 |
| WO | 2018068028 | A1 | 4/2018 |
| WO | 2018085862 | A2 | 5/2018 |
| WO | 2018175501 | A1 | 9/2018 |
| WO | 2019018757 | A1 | 1/2019 |
| WO | 2019133937 | A1 | 7/2019 |
| WO | 2020056347 | A1 | 3/2020 |
| WO | 2021022225 | A1 | 2/2021 |

OTHER PUBLICATIONS

Astier, Y. et al. "Toward Single Molecule DNA Sequencing: Direct Identification of Ribonucleoside and Deoxyribonucleoside 5'-Monophosphates by Using an Engineered Protein Nanopore Equipped with a Molecular Adapter" J Am Chem Soc (2006) 128(5):1705-1710.

Beck, J. et al. "Next Generation Sequencing of Serum Circulating Nucleic Acids from Patients with Invasive Ductal Breast Cancer Reveals Differences to Healthy and Nonmalignant Controls" Mol Canc Res ((2010) 8(3):335-342.

Chang, L. et al. "Microsatellite Instability: A Predictive Biomarker for Cancer Immunotherapy" Appl Immunohistochem Mol Morphol, (2018) 26(2):e15-e21.

Choudhury, Y. et al. "An enhanced next-generation sequencing liquid biopsy assay for simultaneous detection of somatic variants, microsatellite instability and viral DNA" J Clin Oncology (2018) 36(15_Suppl): e24107, 1 page.

Deng, A. et al. "Monitoring microsatellite instability (MSI) in circulating tumor DNA by next-generation DNA-seq" J Clin Oncology (2018) 36(15_Suppl):12025, 1 page.

Georgiadis, A. et al. "Noninvasive Detection of Microsatellite Instability and High Tumor Mutation Burden in Cancer Patients Treated with PD-1 Blockade" Clin Canc Res (2019) 25(23):7024-7034.

Gupta, P. et al. "Abstract 3652:Analytical validation of a novel circulating tumor DNA detection platform for targeted an immunotherapy selection" Cancer Res (2018) 78(13_Suppl):3652, 2 pages.

Hause, R.J. et al. "Classification and characterization of microsatellite instability across 18 cancer types" Nature Medicine (2016) 22(11):1342-1350.

International search report and opinion dated Feb. 10, 2020 for PCT/US2019/048999.

Koh, W-J. et al. "NCCN Clinical Practice Guidelines in Oncology, Cervical Cancer, Version 3.2019" (2019) J Natl Compr Canc Netw.; 17:64-84.

Le, D.T. et al. "PD-1 Blockade in Tumors with Mismatch-Repair Deficiency" NEJM (2015) 372:2509-2520.

Levy, S.E. et al. "Advancements in Next-Generation Sequencing" Ann Rev Genomics & Hum Genetics (2016) 17:95-115.

Liu, L. et al. "Comparison of Next-Generation Sequencing Systems" J Biomed & Biotech (2012) Article ID251364:1-11.

Maclean, D. et al. "Application of 'next-generation' sequencing technologies to microbial genetics" Nature Rev Microbiol (2009) 7:287-296.

Mayrhofer, M. et al. "Cell-free DNA profiling of metastatic prostrate cancer reveals microsatellite instability, structural rearrangements and clonal hematopoiesis" Genome Medicine 10(1): 13 pages, Yr: 2018.

Office Action for U.S. Appl. No. 18/500,890, dated Aug. 14, 2024.

Pardoll, D.M. "The blockade of immune checkpoints in cancer immunotherapy" Nature Rev Cancer (2012) 12:252-264.

Salipante, S.J. et al. "Microsatellite Instability Detection by Next Generation Sequencing" Clin Chem (2014) 60(9):1192-1199.

Van Dijk, E.L. et al. "Library preparation methods for next-generation sequencing: tone down the bias" Exp Cell Res (2014) 322(1):12-20.

Voelkerding, K.V. et al. "Next-generation sequencing: from basic research to diagnostics" Clin Chem (2009) 55:641-658.

Willis, J. et al. "Validation of Microsatellite Instability Detection Using a Comprehensive Plasma-Based Genotyping Panel" Clin Canc Res (2019) pp. 7035-7045.

Zhao, J. et al. "Abstract 1675: Analytical validation of MSI High detection with GuardantOMNI" BioInformatics, Convergence Science, and Systems Biology (2019) p. 1675.

Kathiresan, N. et al. "Accelerating next generation sequencing data analysis with system level optimizations" Sci Reports (2017) 7:9058, 11 pages.

Schmitt, et al. Detection of ultra-rare mutations by next-generation sequencing. Proc Natl Acad Sci U S A. Sep. 4, 2012;109(36):14508-13. doi: 10.1073/pnas.1208715109. Epub Aug. 1, 2012, 6 pages.

* cited by examiner

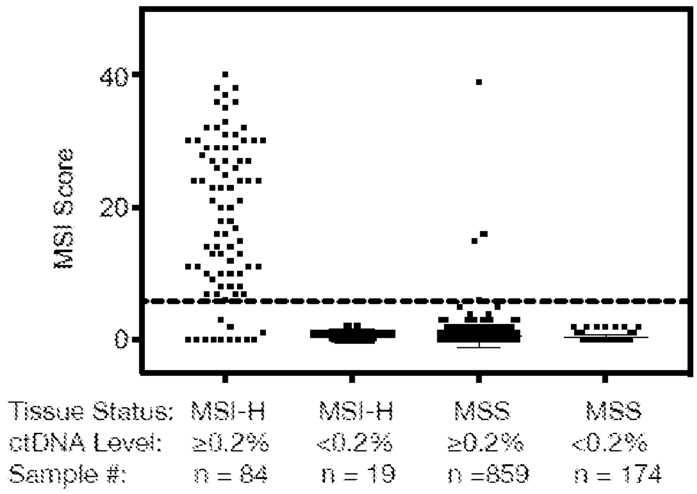
FIGURE 10A
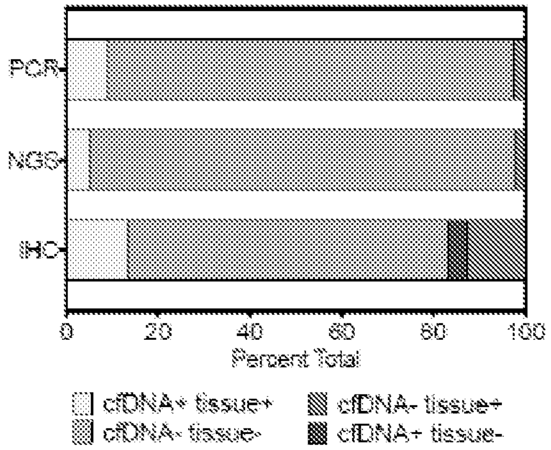
FIGURE 10B
| | |
|---|---|
| **Total Samples** | 1145 |
| **Unique Evaluable Patients** | 949 |
| **PPA** | 87% (71/82, 77-93%) |
| **NPA** | 99.5% (863/867, 98.7-99.8%) |
| **PPV** | 95% (71/75, 86-98%) |
| **Accuracy** | 98.4% (934/949, 97.3-99.1%) |
FIGURE 10C

MICROSATELLITE INSTABILITY DETECTION IN CELL-FREE DNA

CROSS-REFERENCE TO RELATED APPLICATIONS

This application is a continuation of U.S. patent application Ser. No. 18/500,890, filed Nov. 2, 2023, which is a continuation of continuation of U.S. patent application Ser. No. 18/456,362, filed Aug. 25, 2023, U.S. patent application Ser. No. 16/907,034, filed Aug. 30, 2019, now issued as 11,773,451, which is a continuation of International Patent Application No. PCT/US2019/048999, filed Aug. 30, 2019, all of which claim the benefit of, and relies on the filing dates of, U.S. provisional patent application Nos. 62/726,182, filed Aug. 31, 2018, 62/823,578, filed Mar. 25, 2019, and 62/857,048, filed Jun. 4, 2019, the entire disclosures of which are incorporated herein by reference.

SEQUENCE LISTING

The Sequence Listing submitted May 27, 2025 as a text file named "38007_0013U7.xml," created on May 27, 2025 and having a size of 1,956 bytes is hereby incorporated by reference pursuant to 37 C.F.R. § 1.52(e)(5).

BACKGROUND

Repetitive nucleic acid elements are patterns of nucleotides (DNA or RNA) that occur in multiple copies throughout eukaryotic and prokaryotic genomes. Examples of such repetitive elements, include microsatellites, short tandem repeats (STRs), and minisatellites, among others. Microsatellites typically include repeat units of less than 10 base pairs. STRs generally include repeat units of two to thirteen nucleotides that are often repeated hundreds of times in a given stretch of nuclear DNA. STR analysis is a common tool used in forensic analysis. Minisatellites are repetitive elements that typically have repeat units from about 10 to 60 base pairs.

Microsatellites, in particular, are highly polymorphic DNA-repeat regions. Microsatellite instability (MSI) is a guideline-recommended biomarker used in assessment of prognosis and treatment choices, including checkpoint inhibitors recently approved for the treatment of cancers with MSI high (MSI-H) status. Plasma-based next generation DNA sequencing (NGS) tests are increasingly used for comprehensive genomic profiling of cancer, however, methods to detect MSI status from cell-free DNA (cfDNA) data are underdeveloped. Additionally, the impact of variable tumor shedding on MSI detection has not been previously evaluated.

There remains a need for methods and related aspects that are useful in assessing the repetitive element instability status, including MSI, in various samples, especially cfDNA samples.

SUMMARY

This application discloses methods, computer readable media, and systems that are useful in determining the microsatellite and/or other repetitive DNA instability status of cell-free DNA (cfDNA) samples from patients and which help guide disease prognosis and treatment decisions. Typically, at least a portion of the methods disclosed herein are computer implemented and achieve results with a high degree of concordance with those obtained using more conventional polymerase chain reaction (PCR)-based MSI assessment approaches.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

In one aspect, the present disclosure provides a method of determining a repetitive nucleic acid instability status of a nucleic acid sample. The method includes (a) quantifying a number of different repeat lengths present at each of a plurality of repetitive nucleic acid loci from sequence information to generate a site score for each of the plurality of the repetitive nucleic acid loci. The sequence information is from a population of repetitive nucleic acid loci in the nucleic acid sample. The method also includes (b) calling a given repetitive nucleic acid locus as being unstable when the site score of the given repetitive nucleic acid locus exceeds a site specific trained threshold for the given repetitive nucleic acid locus to generate a repetitive nucleic acid instability score comprising a number of unstable repetitive nucleic acid loci from the plurality of the repetitive nucleic acid loci. In addition, the method also includes (c) classifying the repetitive nucleic acid instability status of the nucleic acid sample as being unstable when the repetitive nucleic acid instability score exceeds a population trained threshold for the population of repetitive nucleic acid loci in the nucleic acid sample, thereby determining the repetitive nucleic acid instability status of the nucleic acid sample.

In another aspect, the present disclosure provides a method of determining a repetitive DNA instability status of a sample (e.g. cell-free DNA (cfDNA) sample). The method includes (a) quantifying a number of different repeat lengths present at each of a plurality of repetitive DNA loci from sequence information to generate a site score for each of the plurality of the repetitive DNA loci. The sequence information is from a population of repetitive DNA loci in the sample. The method also includes (b) comparing the site score of a given repetitive DNA locus to a site specific trained threshold for the given repetitive DNA locus for each of the plurality of the repetitive DNA loci. The method further includes (c) calling the given repetitive DNA locus as being unstable when the site score of the given repetitive DNA locus exceeds the site specific trained threshold for the given repetitive DNA locus to generate a repetitive DNA instability score comprising a number of unstable repetitive DNA loci from the plurality of the repetitive DNA loci. In addition, the method also includes (d) classifying the repetitive DNA instability status of the sample as being unstable when the repetitive DNA instability score exceeds a population trained threshold for the population of repetitive DNA loci in the sample, thereby determining the repetitive DNA instability status of the sample. The methods disclosed herein are typically at least partially computer implemented.

In another aspect, the present disclosure provides a method of determining a microsatellite instability (MSI) status of a sample. The includes (a) quantifying a number of different repeat lengths present at each of a plurality of microsatellite loci from sequence information to generate a site score for each of the plurality of the microsatellite loci in which the sequence information is from a population of microsatellite loci in the sample. The method also includes (b) comparing the site score of a given microsatellite locus to a site specific trained threshold for the given microsatellite locus for each of the plurality of the microsatellite loci. The method further includes (c) calling the given microsatellite locus as being unstable when the site score of the given microsatellite locus exceeds the site specific trained threshold for the given microsatellite locus to generate a microsatellite instability score comprising a number of unstable microsatellite loci from the plurality of the microsatellite loci. In addition, the method also includes (d) classifying the MSI status of the sample as being unstable when the microsatellite instability score exceeds a population trained threshold for the population of microsatellite loci in the sample, thereby determining the MSI status of the sample.

In another aspect, the present disclosure provides a method of determining a microsatellite instability (MSI) status of a sample. The method includes (a) receiving sequence information from a population of microsatellite loci in the sample, and (b) quantifying a number of different repeat lengths present at each of a plurality of the microsatellite loci from the sequence information to generate a site score for each of the plurality of the microsatellite loci. The method also includes (c) comparing the site score of a given microsatellite locus to a site specific trained threshold for the given microsatellite locus for each of the plurality of the microsatellite loci. The method further includes (d) calling the given microsatellite locus as being unstable when the site score of the given microsatellite locus exceeds the site specific trained threshold for the given microsatellite locus to generate a microsatellite instability score comprising a number of unstable microsatellite loci from the plurality of the microsatellite loci. In addition, the method also includes (e) classifying the MSI status of the sample as being unstable when the microsatellite instability score exceeds a population trained threshold for the population of microsatellite loci in the sample, thereby determining the MSI status of the sample.

In another aspect, the present disclosure provides a method of identifying one or more customized therapies for treating a disease in a subject. The method includes (a) quantifying a number of different repeat lengths present at each of a plurality of microsatellite loci from sequence information to generate a site score for each of the plurality of the microsatellite loci in which the sequence information is from a population of microsatellite loci in a sample. The method also includes (b) comparing the site score of a given microsatellite locus to a site specific trained threshold for the given microsatellite locus for each of the plurality of the microsatellite loci. The method further includes (c) calling the given microsatellite locus as being unstable when the site score of the given microsatellite locus exceeds the site specific trained threshold for the given microsatellite locus to generate a microsatellite instability score comprising a number of unstable microsatellite loci from the plurality of the microsatellite loci. The method also includes (d) classifying the MSI status of the sample as being unstable when the microsatellite instability score exceeds a population trained threshold for the population of microsatellite loci in the sample to identify an unstable sample. In addition, the method also includes (e) comparing the microsatellite instability status of the sample to one or more comparator results that are indexed with one or more therapies to identify one or more customized therapies for treating the disease in the subject.

In another aspect, the present disclosure provides a method of treating a disease in a subject. The method includes (a) quantifying a number of different repeat lengths present at each of a plurality of microsatellite loci from sequence information to generate a site score for each of the plurality of the microsatellite loci, wherein the sequence information is from a population of microsatellite loci in a sample. The method also includes (b) comparing the site score of a given microsatellite locus to a site specific trained threshold for the given microsatellite locus for each of the plurality of the microsatellite loci. The method further includes (c) calling the given microsatellite locus as being unstable when the site score of the given microsatellite locus exceeds the site specific trained threshold for the given microsatellite locus to generate a microsatellite instability score comprising a number of unstable microsatellite loci from the plurality of the microsatellite loci. The method also includes (d) classifying the MSI status of the sample as being unstable when the microsatellite instability score exceeds a population trained threshold for the population of microsatellite loci in the sample to identify an unstable sample. The method also includes (e) comparing the microsatellite instability status of the sample to one or more comparator results that are indexed with one or more therapies to identify one or more customized therapies for treating the disease in the subject. In addition, the method also includes (f) administering at least one of the identified customized therapies to the subject when there is a substantial match between the microsatellite instability status of the sample and the comparator results, thereby treating the disease in the subject.

In another aspect, the present disclosure provides a method of treating a disease in a subject. The method includes administering one or more customized therapies to the subject, thereby treating the disease in the subject, in which the customized therapies have been identified by: (a) quantifying a number of different repeat lengths present at each of a plurality of microsatellite loci from sequence information to generate a site score for each of the plurality of the microsatellite loci, wherein the sequence information is from a population of microsatellite loci in a sample. The method also includes (b) comparing the site score of a given microsatellite locus to a site specific trained threshold for the given microsatellite locus for each of the plurality of the microsatellite loci. The method further includes (c) calling the given microsatellite locus as being unstable when the site score of the given microsatellite locus exceeds the site specific trained threshold for the given microsatellite locus to generate a microsatellite instability score comprising a number of unstable microsatellite loci from the plurality of the microsatellite loci. The method also includes (d) classifying the MSI status of the sample as being unstable when the microsatellite instability score exceeds a population trained threshold for the population of microsatellite loci in the sample to identify an unstable sample. The method further includes (e) comparing the microsatellite instability status of the sample to one or more comparator results that are indexed with one or more therapies. In addition, the method also includes (f) identifying one or more customized therapies for treating the disease in the subject when there is a substantial match between the microsatellite instability status of the sample and the comparator results.

In some embodiments, the site scores of the plurality of the microsatellite loci comprise likelihood scores. In certain of these embodiments, the likelihood scores comprise probabilistic log likelihood-based scores that discriminate biological signal derived from a number of nucleic acid fragments (in some embodiments—cfDNA fragments) of somatic origin in the sample from noise arising from post-sample collection artifacts in the sample. In some embodiments, the methods include determining the probabilistic log likelihood-based score for an individual microsatellite locus in the sequence information from the sample using at least two parameters in which at least a first parameter comprises allele frequencies and at least a second parameter comprises at least one error mode. Typically, the allele frequencies comprise frequencies of nucleic acids comprising different repeat lengths in the sequence information from the sample. In some embodiments, the at least one error mode comprises a random error mode and a strand specific error mode. In certain embodiments, the site scores of the plurality of the microsatellite loci comprise a difference between or ratio of: (a) a score measuring a support of observed sequences for a null hypothesis that the given microsatellite locus is stable, and (b) a score measuring a support of observed sequences for an alternate hypothesis that the given microsatellite locus is unstable. In some embodiments, the site scores of the plurality of the microsatellite loci are generated using one or more of: a likelihood criterion, a log-likelihood criterion, a posterior probability criterion, an Akaike information criterion (AIC), a Bayesian information criterion, and/or the like.

In some embodiments, the site scores of the plurality of the microsatellite loci comprise Akaike Information Criterion (AIC)-based site scores that test for a presence of somatic indels at the plurality of the microsatellite loci. In certain of these embodiments, a given AIC-based site score is calculated using the formula of:

$$AIC = k - \log - \text{likelihood},$$

where k is the number of parameters used in a model. Optionally, the methods include estimating the parameters of the model using a maximum likelihood estimation (MLE). In some of these embodiments, the methods include determining the MLE using a Nelder-Mead algorithm. In certain embodiments, the methods include calculating a null hypothesis score (e.g., a score measuring a support of observed sequences for a null hypothesis that the given microsatellite locus is stable) of the model using the formula of:

$$AIC_0 = k - \log\left(Pr\left(obs|\beta, \gamma\right)\right),$$

where $AIC_0$ is the null hypothesis, k is the number of parameters used in the model, Pr is probability, obs comprises repeat lengths of observed sequencing reads covering the given microsatellite locus, β is at least one strand specific error parameter, and γ is at least one random error parameter. In certain embodiments, obs is a number of observed sequencing reads covering the given microsatellite locus In some of these embodiments, the methods include calculating an alternate hypothesis score (e.g., a score measuring a support of observed sequences for an alternate hypothesis that the given microsatellite locus is unstable) of the model using the formula of:

$$AIC_{min} = \min_\alpha \left(k - \log\ \left(Pr\left(obs|\beta, \gamma, \alpha\right)\right),\right.$$

where $AIC_{min}$ is the alternate hypothesis, $\min_\alpha$ an effect of minimizing over all values of α, k is the number of parameters used in the model, Pr is probability, obs comprises repeat lengths of observed sequencing reads covering the given microsatellite locus, β is at least one strand specific error parameter, γ is at least one random error parameter, and α is at least one allele frequency, wherein α is a vector of allele frequencies such that the sum of one or more $\alpha_i$ is equal to one. In some embodiments, obs is a number of observed sequencing reads covering the given microsatellite locus In certain of these embodiments, the methods include detecting change in the model to determine site scores (i.e., AAIC) using the formula of:

$$\Delta AIC = AIC_0 - AIC_{min}.$$

In some of these embodiments, γ comprises: (a) a rate of read-level errors where a microsatellite length observed within a sequencing read is one repeat unit longer than an expected microsatellite length for a strand of an originating nucleic acid molecule; and/or (b) a rate of read-level errors where a microsatellite length observed within a sequencing read is one repeat unit shorter than an expected microsatellite length for a strand of an originating nucleic acid molecule. In certain of these embodiments, β comprises: (a) a rate of strand-level errors where an expected microsatellite length of a sense strand is one repeat unit longer than an expected microsatellite length of an nucleic acid originating molecule; (b) a rate of strand-level errors where an expected microsatellite length of an antisense strand is one repeat unit longer than an expected microsatellite length of an nucleic acid originating molecule; (c) a rate of strand-level errors where an expected microsatellite length of a sense strand is one repeat unit shorter than an expected microsatellite length of an nucleic acid originating molecule; and/or, (d) a rate of strand-level errors where an expected microsatellite length of an antisense strand is one repeat unit shorter than an expected microsatellite length of an nucleic acid originating molecule. Typically, the method includes calling the given microsatellite locus as being unstable when the site score of the given microsatellite locus statistically exceeds the site specific trained threshold for the given microsatellite locus.

In some embodiments, a AIC-based site score is calculated using the formula of:

$$AIC = 2\,(k - \log - \text{likelihood}),$$

where k is the number of parameters used in a model. In these embodiments, $AIC_0$ and $AIC_{min}$ are calculated using the above formula.

For clarity purposes, in the embodiments that determine AIC-based score using the formula AIC=2(k−log-likelihood), the site specific threshold that is used to classify a site as unstable will be twice the site specific threshold used in the previous embodiment, where the AIC-based score is determined using the formula AIC=k−log-likelihood.

Typically, a mutant allele fraction (MAF) of the sample (e.g. cfDNA sample) is estimated. In some of these embodiments, a tumor fraction of the sample (e.g. cfDNA sample) is estimated. In certain embodiments, the tumor fraction comprises a maximum mutant allele fraction (MAF) of all somatic mutations identified in the nucleic acids in the sample (e.g. cfDNA sample). In some embodiments, the tumor fraction is below about 0.05%, about 0.1%, about 0.2%, about 0.5%, about 1%, about 2%, about 3%, about 4%, about 5%, about 6%, about 7%, about 8%, about 9%, about 10%, about 11%, about 12%, about 13%, about 14%, or about 15% of all nucleic acids in the sample (e.g. cfDNA sample). In some embodiments, the plurality of microsatellite loci comprises all of the population of microsatellite loci, whereas in other embodiments, the plurality of microsatellite loci comprises a subset of the population of microsatellite loci. In certain embodiments, the methods include determining the site specific trained threshold and/or the population trained threshold from sequence information from a population of microsatellite loci in one or more training DNA samples. In some of these embodiments, the training DNA samples comprise non-tumor cfDNA training samples and/or DNA from one or more tumor types.

In some embodiments, the methods comprise a sensitivity of at least about 94% at a limit of detection (LOD) of about a 0.1-0.4% tumor fraction of nucleic acids in the sample. In some embodiments, the methods comprise analytical specificity of at least about 99% for non-tumor DNA in the sample. In certain embodiments, the determined MSI status of the sample comprises at least about 90%, 91%, 92%, 93%, 94% 95%, 96%, 97%, 98%, or 99% concordance with a corresponding MSI status of the sample determined using a PCR-based MSI assessment technique across a tumor fraction range of about 1% to about 15%. In some of these embodiments, the concordance is 100%. In some embodiments, the methods include classifying the MSI status of the sample as MSI-high (MSI-H) when the microsatellite instability score is greater than about 1, about 2, about 3, about 4, about 5, about 6, about 7, about 8, about 9, about 10, about 15, about 20, about 30, about 40, about 50, or more unstable microsatellite loci from the plurality of the microsatellite loci. In certain embodiments, the methods include classifying the MSI status of the sample as MSI-high (MSI-H) when the number of unstable microsatellite loci comprises about 0.1%, about 1%, about 2%, about 3%, about 4%, about 5%, about 10%, about 15%, about 20%, or about 25% of the plurality of the microsatellite loci. In some embodiments, the number of different repeat lengths comprises a frequency of each different repeat length present at each of the plurality of microsatellite loci.

In various embodiments, the present disclosure includes methods of selecting customized therapies for treating disease in subjects, and/or methods of treating disease in subjects. In some of these embodiments, the disease comprises a cancer comprising at least one tumor type selected from the group consisting of, but not limited to: biliary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, Wilms tumor, leukemia, acute lymphocytic leukemia (ALL), acute myeloid leukemia (AML), chronic lymphocytic (CLL), chronic myeloid (CML), chronic myelomonocytic (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T cell lymphomas, non-Hodgkin lymphoma, precursor T-lymphoblastic lymphoma/leukemia, peripheral T cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas. prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, and uterine sarcoma.

In some embodiments, the therapies comprise at least one immunotherapy (e.g., checkpoint inhibitor antibody, autologous cytotoxic T cells, personalized cancer vaccine, etc.). In certain embodiments, for example, the immunotherapy comprises an antibody against PD-1, PD-2, PD-L1, PD-L2, CTLA-4, OX40, B7.1, B7He, LAG3, CD137, KIR, CCR5, CD27, CD40, or CD47. In some embodiments, the immunotherapy comprises administration of a pro-inflammatory cytokine against at least one tumor type. Optionally, the immunotherapy comprises administration of T cells against at least one tumor type.

In some embodiments, the methods include obtaining the sample from a subject. Essentially any sample type is optionally utilized. In certain embodiments, for example, the sample is tissue, blood, plasma, serum, sputum, urine, semen, vaginal fluid, feces, synovial fluid, spinal fluid, saliva, and/or the like. Typically, the subject is a mammalian subject (e.g., a human subject). In some embodiments, the sample is blood. In some embodiments, the sample is plasma. In some embodiments, the sample is serum. In some embodiments, the sample comprises cell-free DNA (i.e., cfDNA sample). In some embodiments, the cfDNA sample comprises circulating tumor nucleic acids.

In certain embodiments, the methods include receiving the sequence information generated from the sample in which the sequence information comprises sequencing reads from the population of microsatellite loci in the sample. In some embodiments, the methods include amplifying one or more segments of nucleic acids in the sample to generate at least one amplified nucleic acid. In certain embodiments, the methods include sequencing nucleic acids from the sample to generate the sequence information. In some embodiments, the sample can be cfDNA sample. In these embodiments, the sequence information comprises cfDNA sequencing reads from the population of microsatellite loci in the cfDNA sample. In some embodiments, the sequence information is obtained from targeted segments of nucleic acids in the sample in which the targeted segments are obtained by selectively enriching one or more regions from the nucleic acids in the sample prior to sequencing. In some of these embodiments, the methods include amplifying the obtained targeted segments prior to sequencing. In these embodiments, the methods typically include attaching one or more adapters comprising molecular barcodes to the nucleic acids prior to amplification. In some embodiments, the methods included attaching one or more sample indexes via amplification prior to the sequencing. Essentially any nucleic acid sequencing technique is optionally used or adapted for use in performing the methods disclosed herein. For example, the sequencing is optionally selected from targeted sequencing, intron sequencing, exome sequencing, whole genome sequencing, and/or the like. In some embodiments, the sequencing is targeted sequencing. In some embodiments, the methods include sequencing at least about 50, about 100, about 150, about 200, about 250, about 500, about 750, about 1,000, about 1,500, about 2,000, or more targeted genomic regions in the nucleic acids of the sample to generate the sequence information.

In another aspect, the present disclosure provides a system, comprising a controller comprising, or capable of accessing, computer readable media comprising non-transitory computer-executable instructions which, when executed by at least one electronic processor perform at least: (a) receiving sequence information from a population of microsatellite loci in a sample; (b) quantifying a number of different repeat lengths present at each of a plurality of the microsatellite loci from the sequence information to generate a site score for each of the plurality of the microsatellite loci; (c) comparing the site score of a given microsatellite locus to a site specific trained threshold for the given microsatellite locus for each of the plurality of the microsatellite loci; (d) calling the given microsatellite locus as being unstable when the site score of the given microsatellite locus exceeds the site specific trained threshold for the given microsatellite locus to generate a microsatellite instability score comprising a number of unstable microsatellite loci from the plurality of the microsatellite loci; and (e) classifying the MSI status of the sample as being unstable when the microsatellite instability score exceeds a population trained threshold for the population of microsatellite loci in the sample to thereby determine the MSI status of the sample.

In some embodiments, the system includes a nucleic acid sequencer operably connected to the controller, which nucleic acid sequencer is configured to provide the sequence information from the population of microsatellite loci in the sample. In some of these embodiments, the nucleic acid sequencer is configured to perform pyrosequencing, single-molecule sequencing, nanopore sequencing, semiconductor sequencing, sequencing-by-synthesis, sequencing-by-ligation or sequencing-by-hybridization on the nucleic acids to generate sequencing reads. In certain embodiments, the system includes a sample preparation component operably connected to the controller, which sample preparation component is configured to prepare the sample (in some cases, cfDNA sample) to be sequenced by a nucleic acid sequencer. In some of these embodiments, the sample preparation component is configured to selectively enrich regions from the nucleic acids in the sample. In certain embodiments, the sample preparation component is configured to attach one or more adapters comprising molecular barcodes to the nucleic acids. In some embodiments, the system includes a nucleic acid amplification component operably connected to the controller, which nucleic acid amplification component is configured to amplify the DNA (in some cases, cfDNA). In certain of these embodiments, the nucleic acid amplification component is configured to amplify selectively enriched regions from the nucleic acids in the sample.

In certain embodiments, the system includes a material transfer component operably connected to the controller, which material transfer component is configured to transfer one or more materials between a nucleic acid sequencer and a sample preparation component. In some embodiments, the system includes a database operably connected to the controller, which database comprises one or more comparator results that are indexed with one or more therapies, and wherein the electronic processor further performs at least: (f) comparing the microsatellite instability status of the sample to one or more comparator results, wherein a substantial match between the microsatellite instability score and the comparator results indicates a predicted response to therapy for a subject.

In yet another aspect, the present disclosure provides a computer readable media comprising non-transitory computer-executable instructions which, when executed by at least one electronic processor perform at least: (a) receiving sequence information from a population of microsatellite loci in a sample; (b) quantifying a number of different repeat lengths present at each of a plurality of the microsatellite loci from the sequence information to generate a site score for each of the plurality of the microsatellite loci; (c) comparing the site score of a given microsatellite locus to a site specific trained threshold for the given microsatellite locus for each of the plurality of the microsatellite loci; (d) calling the given microsatellite locus as being unstable when the site score of the given microsatellite locus exceeds the site specific trained threshold for the given microsatellite locus to generate a microsatellite instability score comprising a number of unstable microsatellite loci from the plurality of the microsatellite loci; and (e) classifying the MSI status of the sample as being unstable when the microsatellite instability score exceeds a population trained threshold for the population of microsatellite loci in the sample to thereby determine the MSI status of the sample.

The systems and computer readable media disclosed herein include various embodiments. In some embodiments, for example, the site scores of the plurality of the microsatellite loci comprise likelihood scores. In certain of these embodiments, the likelihood scores comprise probabilistic log likelihood-based scores that discriminate biological signal derived from a number of nucleic acid fragments (in some embodiments-cfDNA fragments) of somatic origin in the sample from noise arising from post-sample collection artifacts in the sample. The probabilistic log likelihood-based score for an individual microsatellite locus in the sequence information from the sample is typically determined using at least two parameters, wherein at least a first parameter comprises allele frequencies and at least a second parameter comprises at least one error mode. The allele frequencies comprise frequencies of nucleic acids comprising different repeat lengths in the sequence information from the sample. The at least one error mode typically comprises a random error mode and a strand specific error mode. In some embodiments, the site scores of the plurality of the microsatellite loci comprise a difference between or ratio of: (a) a score measuring a support of observed sequences for a null hypothesis that the given microsatellite locus is stable, and (b) a score measuring a support of observed sequences for an alternate hypothesis that the given microsatellite locus is unstable. In some embodiments, the site scores of the plurality of the microsatellite loci are generated using one or more statistical model selection criteria, such as a likelihood criterion, a log-likelihood criterion, a posterior probability criterion, an Akaike information criterion (AIC), a Bayesian information criterion, and/or the like.

In some embodiments of the systems or computer readable media, the site scores of the plurality of the microsatellite loci comprise Akaike Information Criterion (AIC)-based site scores that test for a presence of somatic indels at the plurality of the microsatellite loci. In certain embodiments, for example, a given AIC-based site score is calculated using the formula of:

$$AIC = k - \log - \text{likelihood},$$

where k is the number of parameters used in a model. Optionally, the parameters of the model are estimated using a maximum likelihood estimation (MLE). In some of these embodiments, the MLE is determined using a Nelder-Mead algorithm. In certain embodiments, a null hypothesis score of the model is calculated using the formula of:

$$AIC_0 = k - \log(Pr(obs|\beta, \gamma)),$$

where $AIC_0$ is the null hypothesis, k is the number of parameters used in the model, Pr is probability, obs comprises repeat lengths of observed sequencing reads covering the given microsatellite locus, β is at least one strand specific error parameter, and γ is at least one random error parameter. In some embodiments, an alternate hypothesis score of the model is calculated using the formula of:

$$AIC_{min} = \min_\alpha (k - \log(Pr(obs|\beta, \gamma, \alpha)),$$

where $AIC_{min}$ is the alternate hypothesis, $\min_\alpha$ an effect of minimizing over all values of α, k is the number of parameters used in the model, Pr is probability, obs comprises repeat lengths of observed sequencing reads covering the given microsatellite locus, β is at least one strand specific error parameter, γ is at least one random error parameter, and α is at least one allele frequency, wherein α is a vector of allele frequencies such that the sum of one or more $\alpha_i$ is equal to one. In these embodiments, change in the model is typically detected to determine site scores using the formula of:

$$\Delta AIC = AIC_0 - AIC_{min}.$$

In some embodiments, γ comprises: (a) a rate of read-level errors where a microsatellite length observed within a sequencing read is one repeat unit longer than an expected microsatellite length for a strand of an originating nucleic acid molecule; and/or (b) a rate of read-level errors where a microsatellite length observed within a sequencing read is one repeat unit shorter than an expected microsatellite length for a strand of an originating nucleic acid molecule. In certain embodiments, β comprises: (a) a rate of strand-level errors where an expected microsatellite length of a sense strand is one repeat unit longer than an expected microsatellite length of an nucleic acid originating molecule; (b) a rate of strand-level errors where an expected microsatellite length of an antisense strand is one repeat unit longer than an expected microsatellite length of an nucleic acid originating molecule; (c) a rate of strand-level errors where an expected microsatellite length of a sense strand is one repeat unit shorter than an expected microsatellite length of an nucleic acid originating molecule; and/or, (d) a rate of strand-level errors where an expected microsatellite length of an antisense strand is one repeat unit shorter than an expected microsatellite length of an nucleic acid originating molecule.

In certain embodiments of the systems or computer readable media, the given microsatellite locus is called as being unstable when the site score of the given microsatellite locus statistically exceeds the site specific trained threshold for the given microsatellite locus. Typically, a tumor fraction that comprises a maximum mutant allele fraction (MAF) of all somatic mutations identified in the nucleic acids in the sample is estimated. In certain embodiments, the tumor fraction is below about 0.05%, about 0.1%, about 0.2%, about 0.5%, about 1%, about 2%, about 3%, about 4%, about 5%, about 6%, about 7%, about 8%, about 9%, about 10%, about 11%, about 12%, about 13%, about 14%, or about 15% of all nucleic acids in the sample. In some embodiments, the plurality of microsatellite loci comprises all of the population of microsatellite loci, whereas in other embodiments, the plurality of microsatellite loci comprises a subset of the population of microsatellite loci. In certain embodiments, the site specific trained threshold and/or the population trained threshold is determined from sequence information from a population of microsatellite loci in one or more training DNA samples. Optionally, the MSI status of the sample is classified as MSI-high (MSI-H) when the microsatellite instability score is greater than about 1, about 2, about 3, about 4, about 5, about 6, about 7, about 8, about 9, about 10, about 15, about 16, about 17, about 18, about 19, about 20, about 30, about 40, about 50, or more unstable microsatellite loci from the plurality of the microsatellite loci. In some embodiments, the MSI status of the sample is classified as MSI-high (MSI-H) when the number of unstable microsatellite loci comprises about 0.1%, about 1%, about 2%, about 3%, about 4%, about 5%, about 10%, about 15%, about 20%, or about 25% of the plurality of the microsatellite loci.

In yet another aspect, the present disclosure provides a system, comprising a communication interface that obtains, over a communication network, sequencing information from one of more nucleic acids in a sample from the subject; and a computer in communication with the communication interface, wherein the computer comprises at least one computer processor and a computer readable medium comprising machine-executable code that, upon execution by at least one computer processor, implements a method comprising: (a) receiving sequence information from a population of microsatellite loci in a sample; (b) quantifying a number of different repeat lengths present at each of a plurality of the microsatellite loci from the sequence information to generate a site score for each of the plurality of the microsatellite loci; (c) comparing the site score of a given microsatellite locus to a site specific trained threshold for the given microsatellite locus for each of the plurality of the microsatellite loci; (d) calling the given microsatellite locus as being unstable when the site score of the given microsatellite locus exceeds the site specific trained threshold for the given microsatellite locus to generate a microsatellite instability score comprising a number of unstable microsatellite loci from the plurality of the microsatellite loci; and (e) classifying the MSI status of the sample as being unstable when the microsatellite instability score exceeds a population trained threshold for the population of microsatellite loci in the sample to thereby determine the MSI status of the sample.

In some embodiments, the sequence information is provided by a nucleic acid sequencer. Typically, the nucleic acid sequencer performs pyrosequencing, single-molecule sequencing, nanopore sequencing, semiconductor sequencing, sequencing-by-synthesis, sequencing-by-ligation, sequencing-by-hybridization, and/or another sequencing technique on the nucleic acids to generate sequencing reads. In some embodiments, the nucleic acid sequencer uses a clonal single molecule array derived from the sequencing library to generate the sequencing reads. In certain embodiments, the nucleic acid sequencer comprises a chip having an array of microwells for sequencing the sequencing library to generate the sequencing reads.

The computer readable medium of the systems disclosed herein typically include a memory, a hard drive or a computer server. In some embodiments, the communication network includes one or more computer servers capable of distributed computing. In some embodiments, the distributed computing is cloud computing. In some embodiments, the computer is located on a computer server that is remotely located from the nucleic acid sequencer. In some embodiments, the systems disclosed herein include an electronic display in communication with the computer over a network, wherein the electronic display comprises a user interface for displaying results upon implementing (i)-(iv). In some of these embodiments, the user interface is a graphical user interface (GUI) or web-based user interface. In some embodiments, the electronic display is in a personal computer. In certain embodiments, the electronic display is in an internet enabled computer. In some of these embodiments, the internet enabled computer is located at a location remote from the computer. Typically, the computer readable medium comprises a memory, a hard drive or a computer server. In some embodiments, the communication network comprises a telecommunication network, an internet, an extranet, or an intranet.

In some embodiments, the results of the systems and methods disclosed herein are used as an input to generate a report. The report may be in a paper or electronic format. For example, the MSI score and/or MSI status obtained by the methods and systems disclosed herein can be displayed directly in such a report. Alternatively or additionally, diagnostic information or the one or more customized therapies based on the MSI status can be included in the report. In some embodiments, the report is communicated to the subject (e.g. a patient) or health care provider.

In some embodiments, the methods, systems or computer readable media, further comprises classifying the repetitive nucleic acid instability status of the nucleic acid sample as being stable if the repetitive nucleic acid instability score is below or at the population trained threshold for the population of repetitive nucleic acid loci in the nucleic acid sample.

In some embodiments, the methods, systems or computer readable media, further comprises classifying the repetitive DNA instability status of the sample as being stable if the repetitive DNA instability score is below or at the population trained threshold for the population of repetitive DNA loci in the sample.

In some embodiments, the methods, systems or computer readable media, further comprises classifying the microsatellite instability status of the sample as being stable if the microsatellite instability score is below or at the population trained threshold for the population of microsatellite loci in the sample.

The various steps of the methods disclosed herein, or steps carried out by the systems disclosed herein, may be carried out at the same or different times, in the same or different geographical locations, e.g. countries, and/or by the same or different people.

BRIEF DESCRIPTION OF THE DRAWINGS

The accompanying drawings, which are incorporated in and constitute a part of this specification, illustrate certain embodiments, and together with the written description, serve to explain certain principles of the methods, computer readable media, and systems disclosed herein. The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

FIG. 6A is a plot showing hierarchical clustering of Akaike Information Criterion scores for 99 candidate microsatellite loci from cfDNA sequencing results from 84 healthy donors. Loci with poor unique molecule coverage are shown in black, while loci with excessive technical artifact are shown in dark grey. Robust but consistent measurements of microsatellite repeat length, defining an informative site, are shown in light gray. Arrows indicate three Bethesda loci included in this study. FIG. 6B is a plot showing observed error rate reduction associated with each component of Digital Sequencing.

FIG. 7C is a plot showing sample-level MSI scores for 499 independent replicates of two microsatellite-stable (MSS) and two MSI-H contrived materials run across 499 separate sequencing runs. Dashed line indicates the sample-level threshold for MSI detection.

FIGS. 10A-10C show concordance data of ctDNA MSI status with tissue testing. FIG. 10A is a plot showing sample-level MSI scores for 1137 cfDNA samples categorized by tissue test result and observed tumor fraction. Dashed line indicates the sample level threshold for MSI detection. FIG. 10B is a plot showing concordance result categorized by tissue test methodology. FIG. 10C is a table showing descriptive statistics for the evaluable unique patient cohort.

FIG. 11A is a plot showing positive axis reports ctDNA MSI prevalence across 16 most prevalent tumor types in the sample set. Negative axis reports the tissue MSI prevalence across the same based on Hause et. al (52). The total number of samples are reported each with the number of MSI-H samples in parentheses. FIG. 11B is a plot showing sample-level MSI scores by tumor type for tumor types with ≥5 MSI-H samples. Dashed line indicates the sample-level threshold for MSI detection. FIG. 11C is a plot showing frequency of individual microsatellite sites contributing to MSI-H samples by tumor type for tumor types with ≥5 MSI-H samples. UCEC, uterine corpus endometrial carcinoma; STAD, stomach adenocarcinoma; COAD, colon adenocarcinoma; PRAD, prostate adenocarcinoma; COUP, cancer of unknown primary; BLCA, bladder carcinoma; CHCA, cholangiocarcinoma; HNSC, head and neck squamous cell carcinoma; LUSC, lung squamous cell carcinoma; BRST, breast carcinoma; PANC, pancreatic adenocarcinoma; LUNG, lung cancer, not otherwise specified; LIHC, liver hepatocellular carcinoma; KIRC, kidney renal cell carcinoma; OV ovarian carcinoma; LUAD, lung adenocarcinoma.

FIG. 13A is a swimmer plot of duration of pembrolizumab therapy in months. Baseline (FIGS. 13B and 13C) and post-therapy (FIGS. 13D and 13E) CT, (FIGS. 13B and 13D) and gastroendoscopy (FIGS. 13C and 13E) for Patient 2.

DEFINITIONS

Figure 1:
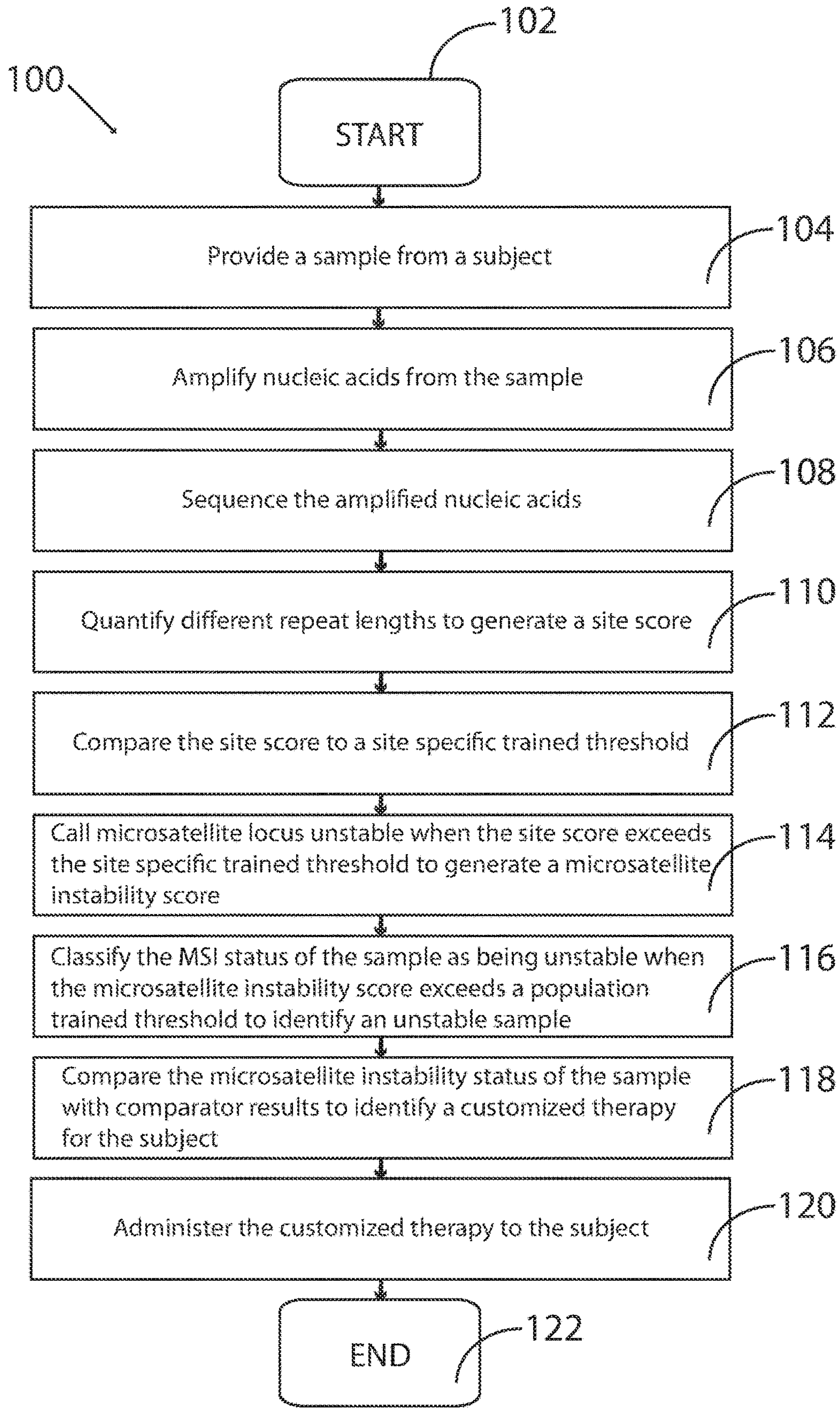
FIG. 1 is a flow chart that schematically depicts exemplary method steps of determining microsatellite instability (MSI) status according to some embodiments of the invention.

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons of ordinary skill in the art upon reading this disclosure and so forth.

It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this disclosure pertains. In describing and claiming the methods, computer readable media, and systems, the following terminology, and grammatical variants thereof, will be used in accordance with the definitions set forth below.

About: As used herein, "about" or "approximately" as applied to one or more values or elements of interest, refers to a value or element that is similar to a stated reference value or element. In certain embodiments, the term "about" or "approximately" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Adapter: As used herein, "adapter" refers to a short nucleic acid (e.g., less than about 500 nucleotides, less than about 100 nucleotides, or less than about 50 nucleotides in length) that is typically at least partially double-stranded and used to link to either or both ends of a given sample nucleic acid molecule. Adapters can include nucleic acid primer binding sites to permit amplification of a nucleic acid molecule flanked by adapters at both ends, and/or a sequencing primer binding site, including primer binding sites for sequencing applications, such as various next-generation sequencing (NGS) applications. Adapters can also include binding sites for capture probes, such as an oligonucleotide attached to a flow cell support or the like. Adapters can also include a nucleic acid tag as described herein. Nucleic acid tags are typically positioned relative to amplification primer and sequencing primer binding sites, such that a nucleic acid tag is included in amplicons and sequence reads of a given nucleic acid molecule. The same or different adapters can be linked to the respective ends of a nucleic acid molecule. In some embodiments, an adapter of the same sequence is linked to the respective ends of the nucleic acid molecule except that the nucleic acid tag differs. In some embodiments, the adapter is a Y-shaped adapter in which one end is blunt ended or tailed as described herein, for joining to a nucleic acid molecule, which is also blunt ended or tailed with one or more complementary nucleotides. In still other example embodiments, an adapter is a bell-shaped adapter that includes a blunt or tailed end for joining to a nucleic acid molecule to be analyzed. Other examples of adapters include T-tailed and C-tailed adapters.

Administer: As used herein, "administer" or "administering" a therapeutic agent (e.g., an immunological therapeutic agent) to a subject means to give, apply or bring the composition into contact with the subject. Administration can be accomplished by any of a number of routes, including, for example, topical, oral, subcutaneous, intramuscular, intraperitoneal, intravenous, intrathecal and intradermal.

Akaike Information Criterion: As used herein, "Akaike information criterion" or "AIC" refers to a criterion for selecting a statistical model from among a finite set of models and includes a penalty term for the number of parameters in the model. In some embodiments, the model with the lowest AIC is selected.

Allele Frequency: As used herein, "allele frequency" refers to the relative frequency of an allele at a particular locus in a population or in a given subject. Allele frequency is typically expressed as a fraction or percentage.

Amplify: As used herein, "amplify" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes.

Barcode: As used herein, "barcode" or "molecular barcode" in the context of nucleic acids refers to a nucleic acid molecule comprising a sequence that can serve as a molecular identifier. For example, individual "barcode" sequences are typically added to each DNA fragment during next-generation sequencing (NGS) library preparation so that each sequencing read can be identified and sorted before the final data analysis.

Cancer Type: As used herein, "cancer," "cancer type" or "tumor type" refers to a type or subtype of cancer defined, e.g., by histopathology. Cancer type can be defined by any conventional criterion, such as on the basis of occurrence in a given tissue (e.g., blood cancers, central nervous system (CNS), brain cancers, lung cancers (small cell and non-small cell), skin cancers, nose cancers, throat cancers, liver cancers, bone cancers, lymphomas, pancreatic cancers, bowel cancers, rectal cancers, thyroid cancers, bladder cancers, kidney cancers, mouth cancers, stomach cancers, breast cancers, prostate cancers, ovarian cancers, lung cancers, intestinal cancers, soft tissue cancers, neuroendocrine cancers, gastroesophageal cancers, head and neck cancers, gynecological cancers, colorectal cancers, urothelial cancers, solid state cancers, heterogeneous cancers, homogenous cancers), unknown primary origin and the like, and/or of the same cell lineage (e.g., carcinoma, sarcoma, lymphoma, cholangiocarcinoma, leukemia, mesothelioma, melanoma, or glioblastoma) and/or cancers exhibiting cancer markers, such as Her2, CA15-3, CA19-9, CA-125, CEA, AFP, PSA, HCG, hormone receptor and NMP-22. Cancers can also be classified by stage (e.g., stage 1, 2, 3, or 4) and whether of primary or secondary origin.

Cell-Free Nucleic Acid: As used herein, "cell-free nucleic acid" refers to nucleic acids not contained within or otherwise bound to a cell or, in some embodiments, nucleic acids naturally remaining in a sample following the removal of intact cells. Cell-free nucleic acids can include, for example, all non-encapsulated nucleic acids sourced from a bodily fluid (e.g., blood, plasma, serum, urine, cerebrospinal fluid (CSF), etc.) from a subject. Cell-free nucleic acids include DNA (cfDNA), RNA (cfRNA), and hybrids thereof, including genomic DNA, mitochondrial DNA, circulating DNA, siRNA, miRNA, circulating RNA (cRNA), tRNA, IRNA, small nucleolar RNA (snoRNA), Piwi-interacting RNA (piRNA), long non-coding RNA (long ncRNA), and/or fragments of any of these. Cell-free nucleic acids can be double-stranded, single-stranded, or a hybrid thereof. A cell-free nucleic acid can be released into bodily fluid through secretion or cell death processes, e.g., cellular necrosis, apoptosis, or the like. Some cell-free nucleic acids are released into bodily fluid from cancer cells, e.g., circulating tumor DNA (ctDNA). Others are released from healthy cells. CtDNA can be non-encapsulated tumor-derived fragmented DNA. Another example of cell-free nucleic acids is fetal DNA circulating freely in the maternal blood stream, also called cell-free fetal DNA (cffDNA). A cell-free nucleic acid can have one or more epigenetic modifications, for example, a cell-free nucleic acid can be acetylated, 5-methylated, ubiquitylated, phosphorylated, sumoylated, ribosylated, and/or citrullinated.

Comparator Result: As used herein, "comparator result" means a result or set of results to which a given test sample or test result can be compared to identify one or more likely properties of the test sample or result, and/or one or more possible prognostic outcomes and/or one or more customized therapies for the subject from whom the test sample was taken or otherwise derived. Comparator results are typically obtained from a set of reference samples (e.g., from subjects having the same disease or cancer type as the test subject and/or from subjects who are receiving, or who have received, the same therapy as the test subject). In certain embodiments, for example, a microsatellite instability status of the sample (e.g. unstable cfDNA sample) is compared with comparator results to identify substantial matches between the microsatellite instability status of the cfDNA test sample and microsatellite instability status determined for a set of reference samples. The microsatellite instability scores determined for the set of reference samples are typically indexed with one or more customized therapies. Thus, when a substantial match is identified, the corresponding customized therapies are thereby also identified as potential therapeutic pathways for the subject from whom the test sample was taken.

Control Sample: As used herein, "control sample" or "control DNA sample" refers to a sample of known composition and/or having known properties and/or known parameters (e.g., known tumor fraction, known coverage, known microsatellite instability score, and/or the like) that is analyzed along with or compared to test samples in order to evaluate the accuracy of an analytical procedure.

Coverage: As used herein, "coverage" refers to the number of nucleic acid molecules that represent a particular base position.

Customized Therapy: As used herein, "customized therapy" refers to a therapy that is associated with a desired therapeutic outcome for a subject or population of subjects selected based on a given criterion, e.g. having a given microsatellite instability status or being within a defined range of microsatellite instability scores.

Deoxyribonucleic Acid or Ribonucleic Acid: As used herein, "deoxyribonucleic acid" or "DNA" refers to a natural or modified nucleotide which has a hydrogen group at the 2'-position of the sugar moiety. DNA typically includes a chain of nucleotides comprising four types of nucleotide bases; adenine (A), thymine (T), cytosine (C), and guanine (G). As used herein, "ribonucleic acid" or "RNA" refers to a natural or modified nucleotide which has a hydroxyl group at the 2'-position of the sugar moiety. RNA typically includes a chain of nucleotides comprising four types of nucleotides; A, uracil (U), G, and C. As used herein, the term "nucleotide" refers to a natural nucleotide or a modified nucleotide. Certain pairs of nucleotides specifically bind to one another in a complementary fashion (called complementary base pairing). In DNA, adenine (A) pairs with thymine (T) and cytosine (C) pairs with guanine (G). In RNA, adenine (A) pairs with uracil (U) and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "sequence information," "nucleic acid sequence," "nucleotide sequence", "genomic sequence," "genetic sequence," or "fragment sequence," or "nucleic acid sequencing read" denotes any information or data that is indicative of the order and identity of the nucleotide bases (e.g., adenine, guanine, cytosine, and thymine or uracil) in a molecule (e.g., a whole genome, whole transcriptome, exome, oligonucleotide, polynucleotide, or fragment) of a nucleic acid such as DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion-or pH-based detection systems, and electronic signature-based systems.

Immunotherapy: As used herein, "immunotherapy" refers to treatment with one or more agents that act to stimulate the immune system so as to kill or at least to inhibit growth of cancer cells, and preferably to reduce further growth of the cancer, reduce the size of the cancer and/or eliminate the cancer. Some such agents bind to a target present on cancer cells; some bind to a target present on immune cells and not on cancer cells; some bind to a target present on both cancer cells and immune cells. Such agents include, but are not limited to, checkpoint inhibitors and/or antibodies. Checkpoint inhibitors are inhibitors of pathways of the immune system that maintain self-tolerance and modulate the duration and amplitude of physiological immune responses in peripheral tissues to minimize collateral tissue damage (see, e.g., Pardoll, Nature Reviews Cancer 12, 252-264 (2012)). Exemplary agents include antibodies against any of PD-1, PD-2, PD-L1, PD-L2, CTLA-4, OX40, B7.1, B7He, LAG3, CD137, KIR, CCR5, CD27, CD40, or CD47. Other exemplary agents include proinflammatory cytokines, such as IL-1B, IL-6, and TNF-α. Other exemplary agents are T-cells activated against a tumor, such as T-cells activated by expressing a chimeric antigen targeting a tumor antigen recognized by the T-cell.

Indel: As used herein, “indel” refers to a mutation that involves the insertion or deletion of one or more nucleotides in the genome of a subject.

Indexed: As used herein, “indexed” refers to a first element (e.g., microsatellite instability score) linked to a second element (e.g., a given therapy).

Instability Status: As used herein, “instability status” or “instability score” (e.g. repetitive nucleic acid/repetitive DNA instability status or score, microsatellite instability status or score) in the context of repetitive nucleic acids refers to a measure or determination of whether a given repetitive nucleic acid locus or population of repetitive nucleic acid loci in one or more nucleic acid samples exhibit a level or degree of mutation (e.g., variable repeat length, etc.) above, at, or below a threshold level determined for that locus or population of loci. For clarity, instability status and instability score are not interchangeable but are rather related concepts. The instability status is based on the instability score. For example, if the instability score of the sample is below or at the population trained threshold, then the sample is classified as stable sample (e.g., for MSI-MSS or MSI-Low) and if the instability score of the sample is above the population trained threshold, then the sample is classified as unstable sample (e.g., for MSI-MSI-High).

Limit of Detection (LoD): As used herein, “limit of detection” or “LoD” means the smallest amount of a substance (e.g., a nucleic acid) in a sample that can be measured by a given assay or analytical approach.

Maximum MAF: As used herein, “maximum MAF” or “max MAF” refers to the maximum MAF of all somatic variants in a sample.

Microsatellite: As used herein, “microsatellite” refers to a repetitive nucleic acid having repeat units of less than about 10 base pairs or nucleotides in length.

Minisatellite: As used herein, “minisatellite” refers to a repetitive nucleic acid having repeat units from about 10 to about 60 base pairs or nucleotides in length.

Mutant Allele Fraction: As used herein, “mutant allele fraction”, “mutation dose,” or “MAF” refers to the fraction of nucleic acid molecules harboring an allelic alteration or mutation at a given genomic position. MAF is generally expressed as a fraction or a percentage. For example, an MAF is typically less than about 0.5, 0.1, 0.05, or 0.01 (i.e., less than about 50%, 10%, 5%, or 1%) of all somatic variants or alleles present at a given locus.

Mutation: As used herein, “mutation” refers to a variation from a known reference sequence and includes mutations such as, for example, single nucleotide variants (SNVs), copy number variants or variations (CNVs)/aberrations, insertions or deletions (indels), gene fusions, transversions, translocations, frame shifts, duplications, repeat expansions, and epigenetic variants. A mutation can be a germline or somatic mutation. In some embodiments, a reference sequence for purposes of comparison is a wildtype genomic sequence of the species of the subject providing a test sample, typically the human genome.

Neoplasm: As used herein, the terms “neoplasm” and “tumor” are used interchangeably. They refer to abnormal growth of cells in a subject. A neoplasm or tumor can be benign, potentially malignant, or malignant. A malignant tumor is referred to as a cancer or a cancerous tumor.

Next Generation Sequencing: As used herein, “next generation sequencing” or “NGS” refers to sequencing technologies having increased throughput as compared to traditional Sanger-and capillary electrophoresis-based approaches, for example, with the ability to generate hundreds of thousands of relatively small sequence reads at a time. Some examples of next generation sequencing techniques include, but are not limited to, sequencing by synthesis, sequencing by ligation, and sequencing by hybridization.

Nucleic Acid Tag: As used herein, “nucleic acid tag” refers to a short nucleic acid (e.g., less than about 500 nucleotides, about 100 nucleotides, about 50 nucleotides, or about 10 nucleotides in length), used to distinguish nucleic acids from different samples (e.g., representing a sample index), or different nucleic acid molecules in the same sample (e.g., representing a molecular barcode), of different types, or which have undergone different processing. The nucleic acid tag comprises a predetermined, fixed, non-random, random or semi-random oligonucleotide sequence. Such nucleic acid tags may be used to label different nucleic acid molecules or different nucleic acid samples or sub-samples. Nucleic acid tags can be single-stranded, double-stranded, or at least partially double-stranded. Nucleic acid tags optionally have the same length or varied lengths. Nucleic acid tags can also include double-stranded molecules having one or more blunt-ends, include 5' or 3' single-stranded regions (e.g., an overhang), and/or include one or more other single-stranded regions at other locations within a given molecule. Nucleic acid tags can be attached to one end or to both ends of the other nucleic acids (e.g., sample nucleic acids to be amplified and/or sequenced). Nucleic acid tags can be decoded to reveal information such as the sample of origin, form, or processing of a given nucleic acid. For example, nucleic acid tags can also be used to enable pooling and/or parallel processing of multiple samples comprising nucleic acids bearing different molecular barcodes and/or sample indexes in which the nucleic acids are subsequently being deconvolved by detecting (e.g., reading) the nucleic acid tags. Nucleic acid tags can also be referred to as identifiers (e.g. molecular identifier, sample identifier). Additionally, or alternatively, nucleic acid tags can be used as molecular barcodes (e.g., to distinguish between different molecules or amplicons of different parent molecules in the same sample or sub-sample). This includes, for example, uniquely tagging different nucleic acid molecules in a given sample, or non-uniquely tagging such molecules. In the case of non-unique tagging applications, a limited number of tags (i.e., molecular barcodes) may be used to tag the nucleic acid molecules such that different molecules can be distinguished based on their endogenous sequence information (for example, start and/or stop positions where they map to a selected reference genome, a sub-sequence of one or both ends of a sequence, and/or length of a sequence) in combination with at least one molecular barcode. Typically, a sufficient number of different molecular barcodes are used such that there is a low probability (e.g., less than about a 10%, less than about a 5%, less than about a 1%, or less than about a 0.1% chance) that any two molecules may have the same endogenous sequence information (e.g., start and/or stop positions, sub-sequences of one or both ends of a sequence, and/or lengths) and also have the same molecular barcode.

Polynucleotide: As used herein, "polynucleotide", "nucleic acid", "nucleic acid molecule", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Oligonucleotides often range in size from a few monomeric units, e.g. 3-4, to hundreds of monomeric units. Whenever a polynucleotide is represented by a sequence of letters, such as "ATGCCTG," it will be understood that the nucleotides are in 5'→3' order from left to right and that in the case of DNA, "A" denotes deoxyadenosine, "C" denotes deoxycytidine, "G" denotes deoxyguanosine, and "T" denotes deoxythymidine, unless otherwise noted. The letters A, C, G, and T may be used to refer to the bases themselves, to nucleosides, or to nucleotides comprising the bases, as is standard in the art.

Population Trained Threshold: As used herein, "population trained threshold" in the context of repetitive nucleic acids refers to a separately determined aggregate maximum number of unstable repetitive nucleic acid loci (e.g., a number of unstable microsatellite loci) expected to be observed in a training DNA sample (e.g., a non-tumor sample, a tumor sample, etc.)

that includes those loci. A population trained threshold is typically used to characterize an experimentally determined repetitive nucleic acid instability score for a particular sample.

Processing: As used herein, the terms "processing", "calculating", and "comparing" can be used interchangeably. In certain applications, the terms refer to determining a difference, e.g., a difference in number or sequence. For example, repetitive DNA instability score (e.g., microsatellite instability score), gene expression, copy number variation (CNV), indel, and/or single nucleotide variant (SNV) values or sequences can be processed.

Reference Sequence: As used herein, "reference sequence" refers to a known sequence used for purposes of comparison with experimentally determined sequences. For example, a known sequence can be an entire genome, a chromosome, or any segment thereof. A reference sequence typically includes at least about 20, at least about 50, at least about 100, at least about 200, at least about 250, at least about 300, at least about 350, at least about 400, at least about 450, at least about 500, at least about 1000, or more nucleotides. A reference sequence can align with a single contiguous sequence of a genome or chromosome or can include non-contiguous segments that align with different regions of a genome or chromosome. Exemplary reference sequences, include, for example, human genomes, such as, hG19 and hG38.

Repeat Length: As used herein, "repeat length" in the context of repetitive nucleic acids refers to the number of repeat units present at a given repetitive nucleic acid locus. To illustrate, the following single-stranded nucleic acid strand has a repeat length of eight (SEQ ID NO: 1):

5'-CGAGGATTATTATTATTATTATTATTATTGCACT-'3.

Repeat Unit: As used herein, "repeat unit" in the context of repetitive nucleic acids refers to the individual nucleotide pattern or motif (e.g., homopolymer or heteropolymer) that is repeated at a given repetitive nucleic acid locus. To illustrate, the following single-stranded nucleic acid strand has a repeat unit of "ATT" (SEQ ID NO: 1):

5'-CGAGGATTATTATTATTATTATTATTATTGCACT-'3.

Repetitive Nucleic Acid: As used herein, "repetitive nucleic acid" or "repetitive element" refers to a recurring pattern of nucleotides that is present in multiple copies throughout a given genome and/or a population of genomes. Repetitive nucleic acid include repetitive DNA and repetitive RNA. Non-limiting examples of repetitive nucleic acids include microsatellites, terminal repeats, tandem repeats, minisatellites, satellite DNA, interspersed repeats, transposable elements (e.g., DNA transposons, retrotransposons (e.g., LTR-retrotransposons (HERVs) and LTR-retrotransposons (HERVs)), etc.), clustered regularly interspaced short palindromic repeats (CRISPR), direct repeats, inverted repeats, mirror repeats, and everted repeats.

Repetitive Nucleic Acid Instability Score: As used herein, "repetitive nucleic acid instability score" (e.g., repetitive DNA instability score, microsatellite instability score, etc.) in the context of repetitive nucleic acids refers to an aggregate number of repetitive nucleic acid loci from a population of repetitive nucleic acid loci in a given sample that are called or otherwise determined to be unstable. This repetitive nucleic acid instability score is a sample-level score (or sample score) and is different from the site score, which is specific to the locus.

Sample: As used herein, "sample" means anything capable of being analyzed by the methods and/or systems disclosed herein.

Sensitivity: As used herein, "sensitivity" means the probability of detecting the presence of a mutation at a given MAF and coverage.

Sequencing: As used herein, "sequencing" refers to any of a number of technologies used to determine the sequence (e.g., the identity and order of monomer units) of a biomolecule, e.g., a nucleic acid such as DNA or RNA. Exemplary sequencing methods include, but are not limited to, targeted sequencing, single molecule real-time sequencing, exon or exome sequencing, intron sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and a combination thereof. In some embodiments, sequencing can be performer by a gene analyzer such as, for example, gene analyzers commercially available from Illumina, Inc., Pacific Biosciences, Inc., or Applied Biosystems/Thermo Fisher Scientific, among many others.

Sequence Information: As used herein, "sequence information" in the context of a nucleic acid polymer means the order and identity of monomer units (e.g., nucleotides, etc.) in that polymer.

Site Score: As used herein, "site score" refers to a measure of likelihood of presence of additional repeat lengths apart from germline repeat length at a given repetitive nucleic acid locus in a sample. In certain embodiments, a site score is determined for a given locus by calculating a delta Akaike information criterion (αAIC) for the locus.

Site Specific Trained Threshold: As used herein, "site specific trained threshold" refers to a separately determined maximum value of a site score for a given repetitive nucleic acid locus (e.g., a given microsatellite locus) such that this locus is stable.

Somatic Mutation: As used herein, "somatic mutation" means a mutation in the genome that occurs after conception. Somatic mutations can occur in any cell of the body except germ cells and accordingly, are not passed on to progeny.

Specificity: As used herein, "specificity" in the context of a diagnostic analysis or assay refers to the extent to which the analysis or assay detects an intended target analyte to the exclusion of other components of a given sample.

Substantial Match: As used herein, "substantial match" means that at least a first value or element is at least approximately equal to at least a second value or element. In certain embodiments, for example, customized therapies are identified when there is at least a substantial or approximate match between a microsatellite instability score and a comparator result.

Subject: As used herein, "subject" refers to an animal, such as a mammalian species (e.g., human) or avian (e.g., bird) species, or other organism, such as a plant. More specifically, a subject can be a vertebrate, e.g., a mammal such as a mouse, a primate, a simian or a human. Animals include farm animals (e.g., production cattle, dairy cattle, poultry, horses, pigs, and the like), sport animals, and companion animals (e.g., pets or support animals). A subject can be a healthy individual, an individual that has or is suspected of having a disease or a predisposition to the disease, or an individual that is in need of therapy or suspected of needing therapy. The terms "individual" or "patient" are intended to be interchangeable with "subject."

For example, a subject can be an individual who has been diagnosed with having a cancer, is going to receive a cancer therapy, and/or has received at least one cancer therapy. The subject can be in remission of a cancer. As another example, the subject can be an individual who is diagnosed of having an autoimmune disease. As another example, the subject can be a female individual who is pregnant or who is planning on getting pregnant, who may have been diagnosed of or suspected of having a disease, e.g., a cancer, an autoimmune disease.

Threshold: As used herein, "threshold" refers to a separately determined value used to characterize or classify experimentally determined values.

Training DNA sample: As used herein, "training DNA sample" refers to a DNA sample used in estimating the site specific trained threshold and population trained threshold. The training DNA sample dataset comprises one or more training DNA samples. The training DNA samples comprise one or more normal DNA samples and/or tumor DNA samples. In some embodiments, the training DNA samples comprise one or more samples with MSI-High and/or MSI-Low/MSS status.

Tumor Fraction: As used herein, "tumor fraction" refers to the estimate of the fraction of nucleic acid molecules derived from a tumor in a given sample. For example, the tumor fraction of a sample can be a measure derived from the max MAF of the sample or coverage of the sample or length of the cfDNA fragments in the sample or any other selected feature of the sample. In some embodiments, the tumor fraction of a sample is equal to the max MAF of the sample.

Unstable: As used herein, "unstable" or "instability" in the context of repetitive nucleic acids refers to a level of mutation (e.g., indels or the like) observed at a given repetitive nucleic acid locus or in a given population of repetitive nucleic acid loci in a nucleic acid sample (e.g., a cfDNA sample) that exceeds a threshold (e.g., a site specific trained threshold—locus level; a population trained threshold—sample level; or the like).

DETAILED DESCRIPTION

Introduction

Cancer encompasses a large group of genetic diseases with the common characteristics of abnormal cell growth and the potential to metastasize beyond the cells' site of origin within the body. The underlying molecular basis of the disease are mutations and/or epigenetic changes that lead to a transformed cellular phenotype, whether those deleterious changes were acquired through heredity or have a somatic basis. To complicate matters, these molecular changes typically vary, not only among patients having the same type of cancer, but even within a given patient's own tumor.

In view of the mutational variability observed in most cancers, one of the challenges of cancer care is to identify therapies to which patients will most likely be responsive given their individualized cancer type. Various biomarkers are used to match cancer patients with appropriate treatments, including cancer immunotherapies. One biomarker of response is microsatellite instability (MSI), which is a condition of, or predisposition to, genetic hypermutability that is caused by an impaired DNA mismatch repair (MMR) mechanism. Cancer patients with microsatellite instability classified as being high (MSI-H or MSI-High) frequently exhibit an accumulation of somatic mutations in tumor cells that leads to a range of molecular and biological changes including high tumor mutational burden, increased expression of neoantigens and abundant tumor-infiltrating lymphocytes. Chang et al. "Microsatellite Instability: A Predictive Biomarker for Cancer Immunotherapy," Appl Immunohistochem Mol Morphol, 26(2):e15-e21 (2018). These changes have been linked to increased sensitivity to checkpoint inhibitor drugs, such as pembrolizumab (Keytruda®), which is used to treat advanced melanoma, head and neck squamous cell carcinoma, non-small cell lung cancer (NSCLC), and classical Hodgkin lymphoma. To date, the application of this response biomarker has been essentially limited to the assessment of MSI status in solid tumor samples using standard PCR-based techniques.

This disclosure provides methods, computer readable media, and systems that are useful in determining and analyzing MSI in patient samples, especially cell-free DNA (cfDNA) samples. The MSI status determined using these methods and related aspects helps guide disease prognosis and treatment decisions. The results achieved with the methods and related aspects disclosed herein generally have a high degree of concordance with, for example, those obtained using more conventional PCR-based MSI assessment approaches.

Methods of Determining Microsatellite Instability Status

This application discloses various methods of accurately determining the microsatellite instability (MSI) status and/or other repetitive DNA instability status of samples (especially, cell-free DNA (cfDNA) samples). In certain embodiments, the methods of assessing MSI status include targeted sequencing of cfDNA, for example, using the Digital Sequencing platform from Guardant Health, Inc. (Redwood City, CA, USA), allows broad coverage of simple repeats where microsatellite instability can occur across a wide range of cancer types. Digital Sequencing platform is an NGS panel of cancer-related genes utilizing high-quality sequencing of cell-free DNA (which could comprise circulating tumor DNA) isolated from a simple, non-invasive blood draw. Digital Sequencing employs pre-sequencing preparation of a digital library of individually tagged cfDNA molecules combined with post-sequencing bioinformatic reconstruction to eliminate nearly all false positives. To illustrate, FIG. 1 provides a flow chart that schematically depicts exemplary method steps of determining the MSI status according to some embodiments of the invention. As shown, method 100 includes quantifying a number of different repeat lengths present at each of a plurality of microsatellite loci from sequence information to generate a site score for each of the plurality of the microsatellite loci in step 110. The sequence information is typically obtained from a population of microsatellite loci in a cfDNA sample. As described further herein, the number of different repeat lengths present at a given microsatellite locus is quantified using a probabilistic log likelihood-based site score in some embodiments. As also described further herein, other quantification approaches are also optionally utilized so long as they too accurately discriminate biological signal derived from relatively small numbers of cfDNA fragments of somatic origin from noise arising, for example, from technical or post-sample collection artifacts (e.g., amplification artifacts, sequencing artifacts, and the like) in samples.

Method 100 also includes comparing the site score of a given microsatellite locus to a site specific trained threshold for that specific microsatellite locus in step 112. The experimentally determined site score of a particular locus and its corresponding site specific trained threshold are typically compared for each of the plurality of the microsatellite loci. The site specific trained threshold of a given locus is generally a predetermined value for that particular locus derived from a population of training DNA samples, such as a cohort of normal or non-tumor cfDNA samples. As shown, method 100 further includes calling a given microsatellite locus as being unstable when the site score (e.g., a likelihood score or the like) of that given microsatellite locus exceeds (e.g., is statistically greater than) the site specific trained threshold for that given microsatellite locus in step 114. Based upon these comparisons, a microsatellite instability score is generated, which includes the number of microsatellite loci called as being unstable from the plurality of the microsatellite loci (e.g., is an overall or aggregate MSI score for the sample). In addition, method 100 also includes classifying the MSI status of the cfDNA sample as being unstable when the microsatellite instability score exceeds a population trained threshold for the population of microsatellite loci in the cfDNA sample to thereby identify an unstable cfDNA sample (e.g., score or predict the sample as being MSI-High) in step 116. In other words, the MSI status of a sample is determined by the presence of a minimum number of unstable microsatellite loci in certain embodiments. The population trained threshold is generally a predetermined value derived from a population of training DNA samples, such as a cohort of normal or non-tumor cfDNA samples.

In some embodiments, thresholds (e.g., site specific trained thresholds, population trained thresholds, and the like) are determined or otherwise derived from at least one training DNA sample dataset. A training DNA sample dataset typically includes from at least about 25 to at least about 30,000 or more training samples. In some embodiments, the training DNA sample dataset includes about 50, 75, 100, 150, 200, 300, 400, 500, 600, 700, 800, 900, 1,000, 2,500, 5,000, 7,500, 10,000, 15,000, 20,000, 25,000, 50,000, 100,000, 1,000,000, or more training DNA samples.

In certain embodiments, method 100 includes additional upstream and/or downstream steps. In some embodiments, for example, method 100 starts in step 102 with providing the sample from the subject in step 104 (e.g., providing a blood sample taken from the subject). In these embodiments, the workflow of method 100 also typically includes amplifying nucleic acids in the sample to generate amplified nucleic acids in step 106 and sequencing the amplified nucleic acids to generate sequence information in step 108, before quantifying the number of different repeat lengths present at each of a plurality of microsatellite loci from the sequence information in step 110. Nucleic acid amplification (including related sample preparation), nucleic acid sequencing, and related data analysis are described further herein.

In some embodiments, method 100 includes various steps that are downstream from the identification of unstable cfDNA samples in step 116. Some examples of these, include comparing the microsatellite instability status of a cfDNA sample to comparator results that are indexed with therapies to identify customized therapies for treating the disease (e.g., cancer or another genetic-based disease, disorder, or condition) in the subject in step 118. In other exemplary embodiments, method 100 also includes administering at least one of the identified customized therapies to the subject when there is a substantial match between the microsatellite instability status of the sample and the comparator results in step 120 before ending in step 122 (e.g., to treat cancer or another disease, disorder, or condition of the subject).

The methods described herein include various alternative embodiments. For example, site scores of microsatellite loci optionally include likelihood scores. In some embodiments, likelihood scores include probabilistic log likelihood-based scores. In some of these embodiments, the methods include determining the probabilistic log likelihood-based score for an individual microsatellite locus in sequence information obtained from a sample using various parameters, such as allele frequencies and one or more error modes (e.g., random error modes, strand specific error mode, and/or the like). Allele frequencies generally include observed frequencies of nucleic acids having different repeat lengths at a given microsatellite locus in sequence information obtained from the sample. In some embodiments, a site score of a particular microsatellite locus includes a difference between or a ratio of: (a) a score measuring a support of observed nucleic acid sequences for a null hypothesis that the given microsatellite locus is stable, and (b) a score measuring a support of observed nucleic acid sequences for an alternate hypothesis that the given microsatellite locus is unstable. Null hypothesis is the hypothesis with minimum AIC score among all hypothesis with assumption that site is stable and alternate hypothesis is the hypothesis with minimum AIC score among all hypothesis with assumption that the site is unstable. Typically, site scores are generated using various measures of model accuracy, such as a likelihood criterion, a log-likelihood criterion, a posterior probability criterion, an Akaike information criterion (AIC), a Bayesian information criterion, and/or the like. Additional details regarding statistical modeling, including measures of statistical model accuracy, that are optionally adapted for using in performing the methods disclosed herein are provided in, for example, Bruce, Practical Statistics for Data Scientists: 50 Essential Concepts, 1st Ed., O'Reilly Media (2017), Freedman et al., Statistics, 4th Ed., W. W. Norton & Company (2007), James et al., An Introduction to Statistical Learning: with Applications in R, 1st Ed., Springer (2013), and Hastie et al., The Elements of Statistical Learning: Data Mining, Inference, and Prediction, 2nd Ed., Springer (2016), which are each incorporated by reference in their entirety.

To further illustrate, a site score of a given microsatellite locus optionally includes an AIC-based site score that tests for a presence of somatic indels at that microsatellite locus. In some of these embodiments, a given AIC-based site score is calculated using the formula of:

$$AIC = k - \log - \text{likelihood},$$

where k is the number of parameters used in a model. In some embodiments, the methods include estimating the parameters of the model using a maximum likelihood estimation (MLE) (e.g., using a Nelder-Mead algorithm or another simplex search algorithm). The methods optionally include calculating a null hypothesis of the model using the formula of:

$$AIC_0 = k - \log\left(Pr\left(obs|\beta, \gamma\right)\right),$$

where $AIC_0$ is the null hypothesis, k is the number of parameters used in the model, Pr is probability, obs is a number of observed sequencing reads covering the given microsatellite locus, β is at least one strand specific error parameter, and γ is at least one random error parameter. In some of these embodiments, the methods include calculating an alternate hypothesis of the model using the formula of:

$$AIC_{min} = \min_\alpha\left(k - \log\left(Pr\left(obs|\beta, \gamma, \alpha\right)\right)\right),$$

where $AIC_{min}$ is the alternate hypothesis, $mina_\alpha$ an effect of minimizing over all values of α, k is the number of parameters used in the model, Pr is probability, obs is a number of observed sequencing reads covering the given microsatellite locus, β is at least one strand specific error parameter, γ is at least one random error parameter, and α is at least one allele frequency, wherein α is a vector of allele frequencies such that the sum of one or more $\alpha_i$ is equal to one. Changes in the model used to determine sites scores (4AIC) are typically detected using the formula of:

$$\Delta AIC = AIC_0 - AIC_{min}.$$

In certain embodiments, the parameter γ includes (a) a rate of read-level errors where a microsatellite length observed within a sequencing read is one repeat unit longer than an expected microsatellite length for a strand of an originating nucleic acid molecule, and/or (b) a rate of read-level errors where a microsatellite length observed within a sequencing read is one repeat unit shorter than an expected microsatellite length for a strand of an originating nucleic acid molecule. In some embodiments, the parameter β includes (a) a rate of strand-level errors where an expected microsatellite length of a sense strand is one repeat unit longer than an expected microsatellite length of an nucleic acid originating molecule, (b) a rate of strand-level errors where an expected microsatellite length of an antisense strand is one repeat unit longer than an expected microsatellite length of an nucleic acid originating molecule, (c) a rate of strand-level errors where an expected microsatellite length of a sense strand is one repeat unit shorter than an expected microsatellite length of an nucleic acid originating molecule, and/or (d) a rate of strand-level errors where an expected microsatellite length of an antisense strand is one repeat unit shorter than an expected microsatellite length of an nucleic acid originating molecule.

In some embodiments, a AIC-based site score is calculated using the formula of:

$$AIC = 2\,(k - \log - \text{likelihood}),$$

where k is the number of parameters used in a model. In these embodiments, $AIC_0$ and $AIC_{min}$ are calculated using the above formula.

For clarity purposes, in the embodiments that determine AIC-based score using the formula AIC=2(k–log-likelihood), the site specific threshold that is used to classify a site as unstable will be twice the site specific threshold used in the previous embodiment, where the AIC-based score is determined using the formula AIC=k–log-likelihood.

The samples analyzed using the methods described herein typically include various mutant allele fractions (MAFs) (e.g., sample fractions exhibiting different repeat lengths a specific microsatellite locus or other allelic alterations). In addition, samples include a tumor fraction in some embodiments. In certain embodiments, the maximum MAF (max MAF) serves as an approximation of the tumor fraction in a given sample. The tumor fraction is typically below about 0.05%, about 0.1%, about 0.2%, about 0.5%, about 1%, about 2%, about 3%, about 4%, about 5%, about 6%, about 7%, about 8%, about 9%, about 10%, about 11%, about 12%, about 13%, about 14%, or about 15% of all nucleic acids in the sample.

In some embodiments, the methods disclosed herein typically include a sensitivity of at least about 94% at a limit of detection (LOD) of about a 0.2% tumor fraction of nucleic acids in a given sample. The methods also generally have a specificity of at least about 99% for non-tumor DNA in the sample. The determined MSI status of a sample also typically has at least about 95%, 96%, 97%, 98%, or 99% concordance with a corresponding MSI status of the sample determined using a standard PCR-based MSI assessment technique across a tumor fraction range of about 1.4% to about 15%. In some embodiments, this concordance is 100%.

In certain embodiments, the MSI status of a particular sample is classified as MSI-high (MSI-H) when the microsatellite instability score for the sample is greater than about 1, about 2, about 3, about 4, about 5, about 6, about 7, about 8, about 9, about 10, about 11, about 12, about 13, about 14, about 15, about 16, about 17, about 18, about 19, about 20, about 30, about 40, about 50, about 60, about 70, about 80, about 90, about 100 or more that 100 unstable microsatellite loci in that sample. In certain embodiments, the population trained threshold used to determine the instability status (e.g., MSI status) of a sample is about 1, about 2, about 3, about 4, about 5, about 6, about 7, about 8, about 9, about 10, about 11, about 12, about 13, about 14, about 15, about 16, about 17, about 18, about 19, about 20, about 30, about 40, about 50, about 60, about 70, about 80, about 90, about 100 or more that 100 unstable repetitive nucleic acid (e.g. microsatellite) loci. In some embodiments, the population trained threshold for the sample is about 5 unstable microsatellite loci. In some embodiments, the population trained threshold for the sample is about 6 unstable repetitive nucleic acid loci. In some embodiments, the population trained threshold for the sample is about 10 unstable repetitive nucleic acid loci. In some embodiments, the population trained threshold for the sample is about 15 unstable repetitive nucleic acid loci. In some embodiments, the population trained threshold for the sample is about 16 unstable repetitive nucleic acid loci. In some embodiments, the population trained threshold for the sample is about 20 unstable repetitive nucleic acid loci. In some embodiments, the population trained threshold for the sample is about 25 unstable repetitive nucleic acid loci. In some embodiments, the population trained threshold for the sample is about 26 unstable repetitive nucleic acid loci. In some embodiments, the population trained threshold for the sample is about 30 unstable repetitive nucleic acid loci. In some embodiments, the population trained threshold for the sample is about 35 unstable repetitive nucleic acid loci. In some embodiments, the population trained threshold for the sample is about 36 unstable repetitive nucleic acid loci. In some embodiments, the population trained threshold for the sample is about 40 unstable repetitive nucleic acid loci. In some embodiments, the population trained threshold for the sample is about 45 unstable repetitive nucleic acid loci. In some embodiments, the population trained threshold for the sample is about 46 unstable repetitive nucleic acid loci. In some embodiments, the population trained threshold for the sample is about 50 unstable repetitive nucleic acid loci. In some embodiments, the repetitive nucleic acid loci can be microsatellite loci. In some embodiments, the MSI status of a given sample is classified as MSI-H when the number of unstable microsatellite loci comprises about 0.1%, about 1%, about 2%, about 3%, about 4%, about 5%, about 10%, about 15%, about 20%, or about 25% of all microsatellite loci evaluated in that sample. In some embodiments, about 50, about 60, about 70, about 80, about 90, about 100, about 200, about 300, about 400, about 500, about 600, about 700, about 800, about 900, about 1000, about 1100, about 1200, about 1300, about 1400, about 1500, about 1600, about 1700, about 1800, about 1900, about 2000, or more than 2000repetitive nucleic acid (e.g. microsatellite) loci are used in determining the repetitive nucle ic acid instability (e.g. MSI) status of a given sample. In some embodiments, about 50 repetitive nucleic acid loci are used in determining the repetitive nucleic acid instability (e.g. MSI) status of a given sample. In some embodiments, about 60 repetitive nucleic acid loci are used in determining the repetitive nucleic acid instability (e.g. MSI) status of a given sample. In some embodiments, about 70 repetitive nucleic acid loci are used in determining the repetitive nucleic acid instability (e.g. MSI) status of a given sample. In some embodiments, about 80 repetitive nucleic acid loci are used in determining the repetitive nucleic acid instability (e.g. MSI) status of a given sample. In some embodiments, about 90 repetitive nucleic acid loci are used in determining the repetitive nucleic acid instability (e.g. MSI) status of a given sample. In some embodiments, about 100 repetitive nucleic acid loci are used in determining the repetitive nucleic acid instability (e.g. MSI) status of a given sample. In some embodiments, about 200 repetitive nucleic acid loci are used in determining the repetitive nucleic acid instability (e.g. MSI) status of a given sample. In some embodiments, about 300 repetitive nucleic acid loci are used in determining the repetitive nucleic acid instability (e.g. MSI) status of a given sample. In some embodiments, about 400 repetitive nucleic acid loci are used in determining the repetitive nucleic acid instability (e.g. MSI) status of a given sample. In some embodiments, about 500 repetitive nucleic acid loci are used in determining the repetitive nucleic acid instability (e.g. MSI) status of a given sample. In some embodiments, about 1000 repetitive nucleic acid loci are used in determining the repetitive nucleic acid instability (e.g. MSI) status of a given sample. In some embodiments, about 1100 repetitive nucleic acid loci are used in determining the repetitive nucleic acid instability (e.g. MSI) status of a given sample. In some embodiments, about 1200 repetitive nucleic acid loci are used in determining the repetitive nucleic acid instability (e.g. MSI) status of a given sample. In some embodiments, about 1300 repetitive nucleic acid loci are used in determining the repetitive nucleic acid instability (e.g. MSI) status of a given sample. In some embodiments, about 1400 repetitive nucleic acid loci are used in determining the repetitive nucleic acid instability (e.g. MSI) status of a given sample. In some embodiments, at least 1500 repetitive nucleic acid loci are used in determining the repetitive nucleic acid instability (e.g. MSI) status of a given sample. In some embodiments, about 1600 repetitive nucleic acid loci are used in determining the repetitive nucleic acid instability (e.g. MSI) status of a given sample. In some embodiments, at least 1700 repetitive nucleic acid loci are used in determining the repetitive nucleic acid instability (e.g. MSI) status of a given sample. In some embodiments, at least 1800 repetitive nucleic acid loci are used in determining the repetitive nucleic acid instability (e.g. MSI) status of a given sample. In some embodiments, at least 1900 repetitive nucleic acid loci are used in determining the repetitive nucleic acid instability (e.g. MSI) status of a given sample. In some embodiments, at least 2000 repetitive nucleic acid loci are used in determining the repetitive nucleic acid instability (e.g. MSI) status of a given sample. In some embodiments, the repetitive nucleic acid loci can be microsatellite loci. In some embodiments, the repetitive nucleic acid instability status can be MSI status In some embodiments, the methods include obtaining the sample from a subject. Essentially any sample type is optionally utilized. In certain embodiments, for example, the sample is tissue, blood, plasma, serum, sputum, urine, semen, vaginal fluid, feces, synovial fluid, spinal fluid, saliva, and/or the like. Additional exemplary sample types that are optionally utilized are described further herein. Typically, the subject is a mammalian subject (e.g., a human subject). Essentially any type of nucleic acid (e.g., DNA and/or RNA) can be evaluated according to the methods disclosed in this application. Some examples, include cell-free nucleic acids (e.g., cfDNA of tumor origin, fetal origin, maternal origin, and/or the like), cellular nucleic acids, including circulating tumor cells (e.g., obtained by lysing intact cells in a sample), circulating tumor nucleic acids, and the like. In some embodiments, the sample comprises cell-free DNA (cfDNA sample). In some embodiments, the cfDNA sample comprises circulating tumor nucleic acids.

The methods disclosed in this application generally include obtaining sequence information from nucleic acids in samples taken from subjects. In certain embodiments, the sequence information is obtained from targeted segments of the nucleic acids. Essentially any number of genomic regions are optionally targeted. The targeted segments can include at least 10, at least 50, at least 100, at least 500, at least 1000, at least 2000, at least 5000, at least 10,000, at least 20,000 or at least 50, 000 (e.g., 25, 50, 75, 100, 200, 300, 400, 500, 600, 700, 800, 900, 1,000, 2,000, 3,000, 4,000, 5,000, 6,000, 7,000, 8,000, 9,000, 10,000, 15,000, 25,000, 30,000, 35,000, 40,000, 45,000) different or overlapping genomic regions. In some embodiments, the targeted segments comprise selected regions of at least 50, at least 60, at least 70, at least 80, at least 90, at least 100, at least 200, at least 300, at least 400, at least 500, at least 600 or at least 700 genes. In some embodiments, the targeted segments comprise selected regions of at least 70 genes. In some embodiments, the targeted segments comprise regions of at least 500 genes.

In these embodiments, the methods also typically include various sample or library preparation steps to prepare nucleic acids for sequencing. Many different sample preparation techniques are well-known to persons skilled in the art. Essentially any of those techniques are used, or adapted for use, in performing the methods described herein. For example, in addition to various purification steps to isolate nucleic acids from other components in a given sample, typical steps to prepare nucleic acids for sequencing include tagging nucleic acids with molecular identifiers or barcodes, adding adapters (e.g., which may include the barcodes), amplifying the nucleic acids one or more times, enriching for targeted segments of the nucleic acids (e.g., using various target capturing strategies, etc.), and/or the like. Exemplary library preparation processes are described further herein. Additional details regarding nucleic acid sample/library preparation are also described in, for example, van Dijk et al., Library preparation methods for next-generation sequencing: Tone down the bias, Experimental Cell Research, 322(1):12-20 (2014), Micic (Ed.), Sample Preparation Techniques for Soil, Plant, and Animal Samples (Springer Protocols Handbooks), $1^{st}$ Ed., Humana Press (2016), and Chiu, Next-Generation Sequencing and Sequence Data Analysis, Bentham Science Publishers (2018), which are each incorporated by reference in their entirety.

Microsatellite and/or other repetitive nucleic acid instability status determined by the methods disclosed herein are optionally used to diagnose the presence of a disease or condition, particularly cancer, in a subject, to characterize such a disease or condition (e.g., to stage a given cancer, to determine the heterogeneity of a cancer, and the like), to monitor response to treatment, to evaluate the potential risk of developing a given disease or condition, and/or to assess the prognosis of the disease or condition. Microsatellite and/or other repetitive nucleic acid instability status are also optionally used for characterizing a specific form of cancer. Since cancers are often heterogeneous in both composition and staging, microsatellite and/or other repetitive nucleic acid instability status data may allow for the characterization of specific sub-types of cancer to thereby assist with diagnosis and treatment selection. This information may also provide a subject or healthcare practitioner with clues regarding the prognosis of a specific type of cancer, and enable a subject and/or healthcare practitioner to adapt treatment options in accordance with the progress of the disease. Some cancers become more aggressive and genetically unstable as they progress. Other tumors remain benign, inactive or dormant.

Microsatellite and/or other repetitive nucleic acid instability status can also be useful in determining disease progression and/or in monitoring recurrence. In certain cases, for example, a successful treatment may initially increase the observed microsatellite and/or other repetitive nucleic acid instability as an increased number of cancer cells die and shed nucleic acids. In these cases, as the therapy progresses, the microsatellite and/or other repetitive nucleic acid instability will then typically decrease as the tumor continues to reduce in size. In other cases, a successful treatment may also decrease microsatellite and/or other repetitive nucleic acid instability without an initial increase in such instability. Additionally, if a cancer is observed to be in remission after treatment, microsatellite and/or other repetitive nucleic acid instability status may be used to monitor residual disease or recurrence of disease in a patient.

Samples

A sample can be any biological sample isolated from a subject. Samples can include body tissues, whole blood, platelets, serum, plasma, stool, red blood cells, white blood cells or leucocytes, endothelial cells, tissue biopsies (e.g., biopsies from known or suspected solid tumors), cerebrospinal fluid, synovial fluid, lymphatic fluid, ascites fluid, interstitial or extracellular fluid (e.g., fluid from intercellular spaces), gingival fluid, crevicular fluid, bone marrow, pleural effusions, cerebrospinal fluid, saliva, mucous, sputum, semen, sweat, urine. Samples are preferably body fluids, particularly blood and fractions thereof, and urine. Such samples include nucleic acids shed from tumors. The nucleic acids can include DNA and RNA and can be in double and single-stranded forms. A sample can be in the form originally isolated from a subject or can have been subjected to further processing to remove or add components, such as cells, enrich for one component relative to another, or convert one form of nucleic acid to another, such as RNA to DNA or single-stranded nucleic acids to double-stranded. Thus, for example, a body fluid sample for analysis is plasma or serum containing cell-free nucleic acids, e.g., cell-free DNA (cfDNA).

In some embodiments, the sample volume of body fluid taken from a subject depends on the desired read depth for sequenced regions. Exemplary volumes are about 0.4-40 ml, about 5-20 ml, about 10-20 ml. For example, the volume can be about 0.5 ml, about 1 ml, about 5 ml, about 10 ml, about 20 ml, about 30 ml, about 40 ml, or more milliliters. A volume of sampled plasma is typically between about 5 ml to about 20 ml.

The sample can comprise various amounts of nucleic acid. Typically, the amount of nucleic acid in a given sample is equated with multiple genome equivalents. For example, a sample of about 30 ng DNA can contain about 10,000 ($10^4$) haploid human genome equivalents and, in the case of cfDNA, about 200 billion ($2\times10^{11}$) individual polynucleotide molecules. Similarly, a sample of about 100 ng of DNA can contain about 30,000 haploid human genome equivalents and, in the case of cfDNA, about 600 billion individual molecules.

In some embodiments, a sample comprises nucleic acids from different sources, e.g., from cells and from cell-free sources (e.g., blood samples, etc.). Typically, a sample includes nucleic acids carrying mutations. For example, a sample optionally comprises DNA carrying germline mutations and/or somatic mutations. Typically, a sample comprises DNA carrying cancer-associated mutations (e.g., cancer-associated somatic mutations).

Exemplary amounts of cell-free nucleic acids in a sample before amplification typically range from about 1 femtogram (fg) to about 1 microgram (μg), e.g., about 1 picogram (pg) to about 200 nanogram (ng), about 1 ng to about 100 ng, about 10 ng to about 1000 ng. In some embodiments, a sample includes up to about 600 ng, up to about 500 ng, up to about 400 ng, up to about 300 ng, up to about 200 ng, up to about 100 ng, up to about 50 ng, or up to about 20 ng of cell-free nucleic acid molecules. Optionally, the amount is at least about 1 fg, at least about 10 fg, at least about 100 fg, at least about 1 pg, at least about 10 pg, at least about 100 pg, at least about 1 ng, at least about 10 ng, at least about 100 ng, at least about 150 ng, or at least about 200 ng of cell-free nucleic acid molecules. In certain embodiments, the amount is up to about 1 fg, about 10 fg, about 100 fg, about 1 pg, about 10 pg, about 100 pg, about 1 ng, about 10 ng, about 100 ng, about 150 ng, or about 200 ng of cell-free nucleic acid molecules. In certain embodiments, methods include obtaining between about 5 ng to about 30 ng of cell-free nucleic acid molecules from samples. In certain embodiments, methods include obtaining between about 5 ng to about 100 ng of cell-free nucleic acid molecules from samples. In certain embodiments, methods include obtaining between about 5 ng to about 150 ng of cell-free nucleic acid molecules from samples. In certain embodiments, methods include obtaining between about 5 ng to about 200 ng of cell-free nucleic acid molecules from samples. In some embodiments, the amount is up to about 100 ng of cell-free nucleic acid molecules from samples. In some embodiments, the amount is up to about 150 ng of cell-free nucleic acid molecules from samples. In some embodiments, the amount is up to about 200 ng of cell-free nucleic acid molecules from samples. In some embodiments, the amount is up to about 250 ng of cell-free nucleic acid molecules from samples. In some embodiments, the amount is up to about 300 ng of cell-free nucleic acid molecules from samples. In some embodiments, methods include obtaining between about 1 fg to about 200 ng cell-free nucleic acid molecules from samples.

Cell-free nucleic acids typically have a size distribution of between about 100 nucleotides in length and about 500 nucleotides in length, with molecules of about 110 nucleotides in length to about 230 nucleotides in length representing about 90% of molecules in the sample, with a mode of about 168 nucleotides in length and a second minor peak in a range between about 240 to about 440 nucleotides in length. In certain embodiments, cell-free nucleic acids are from about 160 to about 180 nucleotides in length, or from about 320 to about 360 nucleotides in length, or from about 440 to about 480 nucleotides in length.

In some embodiments, cell-free nucleic acids are isolated from bodily fluids through a partitioning step in which cell-free nucleic acids, as found in solution, are separated from intact cells and other non-soluble components of the bodily fluid. In some of these embodiments, partitioning includes techniques such as centrifugation or filtration. Alternatively, cells in bodily fluids are lysed, and cell-free and cellular nucleic acids processed together. Generally, after addition of buffers and wash steps, cell-free nucleic acids are precipitated with, for example, an alcohol. In certain embodiments, additional clean up steps are used, such as silica-based columns to remove contaminants or salts. Non-specific bulk carrier nucleic acids, for example, are optionally added throughout the reaction to optimize certain aspects of the exemplary procedure, such as yield. After such processing, samples typically include various forms of nucleic acids including double-stranded DNA, single-stranded DNA and/or single-stranded RNA. Optionally, single stranded DNA and/or single stranded RNA are converted to double stranded forms so that they are included in subsequent processing and analysis steps.

Nucleic Acid Tags

In some embodiments, the nucleic acid molecules (from the sample of polynucleotides) may be tagged with sample indexes and/or molecular barcodes (referred to generally as "tags"). Tags may be incorporated into or otherwise joined to adapters by chemical synthesis, ligation (e.g., blunt-end ligation or sticky-end ligation), or overlap extension polymerase chain reaction (PCR), among other methods. Such adapters may be ultimately joined to the target nucleic acid molecule. In other embodiments, one or more rounds of amplification cycles (e.g., PCR amplification) are generally applied to introduce sample indexes to a nucleic acid molecule using conventional nucleic acid amplification methods. The amplifications may be conducted in one or more reaction mixtures (e.g., a plurality of microwells in an array). Molecular barcodes and/or sample indexes may be introduced simultaneously, or in any sequential order. In some embodiments, molecular barcodes and/or sample indexes are introduced prior to and/or after sequence capturing steps are performed. In some embodiments, only the molecular barcodes are introduced prior to probe capturing and the sample indexes are introduced after sequence capturing steps are performed. In some embodiments, both the molecular barcodes and the sample indexes are introduced prior to performing probe-based capturing steps. In some embodiments, the sample indexes are introduced after sequence capturing steps are performed. In some embodiments, molecular barcodes are incorporated to the nucleic acid molecules (e.g. cfDNA molecules) in a sample through adapters via ligation (e.g., blunt-end ligation or sticky-end ligation). In some embodiments, sample indexes are incorporated to the nucleic acid molecules (e.g. cfDNA molecules) in a sample through overlap extension polymerase chain reaction (PCR). Typically, sequence capturing protocols involve introducing a single-stranded nucleic acid molecule complementary to a targeted nucleic acid sequence, e.g., a coding sequence of a genomic region and mutation of such region is associated with a cancer type.

In some embodiments, the tags may be located at one end or at both ends of the sample nucleic acid molecule. In some embodiments, tags are predetermined or random or semi-random sequence oligonucleotides. In some embodiments, the tags may be less than about 500, 200, 100, 50, 20, 10, 9, 8, 7, 6, 5, 4, 3, 2, or 1 nucleotides in length. The tags may be linked to sample nucleic acids randomly or non-randomly.

In some embodiments, each sample is uniquely tagged with a sample index or a combination of sample indexes. In some embodiments, each nucleic acid molecule of a sample or sub-sample is uniquely tagged with a molecular barcode or a combination of molecular barcodes. In other embodiments, a plurality of molecular barcodes may be used such that molecular barcodes are not necessarily unique to one another in the plurality (e.g., non-unique molecular barcodes). In these embodiments, molecular barcodes are generally attached (e.g., by ligation) to individual molecules such that the combination of the molecular barcode and the sequence it may be attached to creates a unique sequence that may be individually tracked. Detection of non-uniquely tagged molecular barcodes in combination with endogenous sequence information (e.g., the beginning (start) and/or end (stop) portions corresponding to the sequence of the original nucleic acid molecule in the sample, sub-sequences of sequence reads at one or both ends, length of sequence reads, and/or length of the original nucleic acid molecule in the sample) typically allows for the assignment of a unique identity to a particular molecule. The length, or number of base pairs, of an individual sequence read are also optionally used to assign a unique identity to a given molecule. As described herein, fragments from a single strand of nucleic acid having been assigned a unique identity, may thereby permit subsequent identification of fragments from the parent strand, and/or a complementary strand.

In some embodiments, molecular barcodes are introduced at an expected ratio of a set of identifiers (e.g., a combination of unique or non-unique molecular barcodes) to molecules in a sample. One example format uses from about 2 to about 1,000,000 different molecular barcodes, or from about 5 to about 150 different molecular barcodes, or from about 20 to about 50 different molecular barcodes. Alternatively, from about 25 to about 1,000,000 different molecular barcodes may be used. The molecular barcodes can be ligated to both ends of a target molecule. For example, 20-50×20-50 molecular barcodes can be used. In some embodiments, 20-50 different molecular barcodes can be used. In some embodiments, 5-100 different molecular barcodes can be used, In some embodiments, 5-150 molecular barcodes can be used. In some embodiments, 5-200 different molecular barcodes can be used. Such numbers of identifiers are typically sufficient for different molecules having the same start and stop points to have a high probability (e.g., at least 94%, 99.5%, 99.99%, or 99.999%) of receiving different combinations of identifiers. In some embodiments, about 80%, about 90%, about 95%, or about 99% of molecules have the same combinations of molecular barcodes.

In some embodiments, the assignment of unique or non-unique molecular barcodes in reactions is performed using methods and systems described in, for example, U.S. patents application Ser. Nos. 20010053519, 20030152490, and 20110160078, and U.S. Pat. Nos. 6,582,908, 7,537,898, 9,598,731, and 9,902,992, each of which is hereby incorporated by reference in its entirety. Alternatively, in some embodiments, different nucleic acid molecules of a sample may be identified using only endogenous sequence information (e.g., start and/or stop positions, sub-sequences of one or both ends of a sequence, and/or lengths).

Nucleic Acid Amplification

Sample nucleic acids flanked by adapters are typically amplified by PCR and other amplification methods using nucleic acid primers binding to primer binding sites in adapters flanking a DNA molecule to be amplified. In some embodiments, amplification methods involve cycles of extension, denaturation and annealing resulting from thermocycling, or can be isothermal as, for example, in transcription mediated amplification. Other exemplary amplification methods that are optionally utilized, include the ligase chain reaction, strand displacement amplification, nucleic acid sequence-based amplification, and self-sustained sequence-based replication, among other approaches.

One or more rounds of amplification cycles are generally applied to introduce sample indexes to a nucleic acid molecule using conventional nucleic acid amplification methods. The amplifications are typically conducted in one or more reaction mixtures. Molecular tags and sample indexes/tags are optionally introduced simultaneously, or in any sequential order. In some embodiments, molecular tags and sample indexes/tags are introduced prior to and/or after nucleic acid molecule capturing steps (i.e., nucleic acid enrichment) are performed. In some embodiments, only the molecular tags are introduced prior to probe capturing and the sample indexes/tags are introduced after sequence capturing steps are performed. In certain embodiments, both the molecular tags and the sample indexes/tags are introduced prior to performing probe-based capturing steps. In some embodiments, the sample indexes/tags are introduced after sequence capturing steps are performed. Typically, sequence capturing protocols involve introducing a single-stranded nucleic acid molecule complementary to a targeted nucleic acid sequence, e.g., a coding sequence of a genomic region and mutation of such region associated with a cancer type. Typically, the amplification reactions generate a plurality of non-uniquely or uniquely tagged nucleic acid amplicons with molecular tags and sample indexes/tags at size ranging from about 200 nucleotides (nt) to about 700 nt, from 250 nt to about 350 nt, or from about 320 nt to about 550 nt. In some embodiments, the amplicons have a size of about 300 nt. In some embodiments, the amplicons have a size of about 500 nt.

Nucleic Acid Enrichment

In some embodiments, sequences are enriched prior to sequencing the nucleic acids. Enrichment is optionally performed for specific target regions ("target sequences"). In some embodiments, targeted regions of interest may be enriched with nucleic acid capture probes ("baits") selected for one or more bait set panels using a differential tiling and capture scheme. A differential tiling and capture scheme generally uses bait sets of different relative concentrations to differentially tile (e.g., at different "resolutions") across genomic regions associated with the baits, subject to a set of constraints (e.g., sequencer constraints such as sequencing load, utility of each bait, etc.), and capture the targeted nucleic acids at a desired level for downstream sequencing. These targeted genomic regions of interest optionally include natural or synthetic nucleotide sequences of the nucleic acid construct. In some embodiments, biotin-labeled beads with probes to one or more regions of interest can be used to capture target sequences, and optionally followed by amplification of those regions, to enrich for the regions of interest.

Sequence capture typically involves the use of oligonucleotide probes that hybridize to the target nucleic acid sequence. In certain embodiments, a probe set strategy involves tiling the probes across a region of interest. Such probes can be, for example, from about 60 to about 120 nucleotides in length. The set can have a depth of about 2×, 3×, 4×, 5×, 6×, 8×, 9×, 10×, 15×, 20×, 30×, 40×, 50× or more than 50×. The effectiveness of sequence capture generally depends, in part, on the length of the sequence in the target molecule that is complementary (or nearly complementary) to the sequence of the probe.

Nucleic Acid Sequencing

Sample nucleic acids, optionally flanked by adapters, with or without prior amplification are generally subject to sequencing. Sequencing methods or commercially available formats that are optionally utilized include, for example, Sanger sequencing, high-throughput sequencing, pyrosequencing, sequencing-by-synthesis, single-molecule sequencing, nanopore-based sequencing, semiconductor sequencing, sequencing-by-ligation, sequencing-by-hybridization, RNA-Seq (Illumina), Digital Gene Expression (Helicos), next generation sequencing (NGS), Single Molecule Sequencing by Synthesis (SMSS) (Helicos), massively-parallel sequencing, Clonal Single Molecule Array (Solexa), shotgun sequencing, Ion Torrent, Oxford Nanopore, Roche Genia, Maxim-Gilbert sequencing, primer walking, sequencing using PacBio, SOLID, Ion Torrent, or nanopore platforms. Sequencing reactions can be performed in a variety of sample processing units, which may include multiple lanes, multiple channels, multiple wells, or other means of processing multiple sample sets substantially simultaneously. Sample processing units can also include multiple sample chambers to enable the processing of multiple runs simultaneously.

The sequencing reactions can be performed on one more nucleic acid fragment types or regions known to contain markers (e.g., microsatellites and/or other repetitive nucleic acid elements) of cancer or of other diseases. The sequencing reactions can also be performed on any nucleic acid fragment present in the sample. The sequence reactions may provide for sequence coverage of the genome of at least about 5%, 10%, 15%, 20%, 25%, 30%, 40%, 50%, 60%, 70%, 80%, 90%, 95%, 99%, 99.9% or 100% of the genome. In other cases, sequence coverage of the genome may be less than about 5%, 10%, 15%, 20%, 25%, 30%, 40%, 50%, 60%, 70%, 80%, 90%, 95%, 99%, 99.9% or 100% of the genome. In some embodiments, sequence coverage of the genome may be less than about 0.01%, 0.02%, 0.05%, 0.1%, 0.2%, 0.5%, 1%, 2% or 5% of the genome. In some embodiments, sequence coverage of the genome may be less than about 0.01% of the genome. In some embodiments, sequence coverage of the genome may be less than about 0.02% of the genome. In some embodiments, sequence coverage of the genome may be less than about 0.05% of the genome. In some embodiments, sequence coverage of the genome may be less than about 0.1% of the genome. In some embodiments, sequence coverage of the genome may be less than about 0.2% of the genome. In some embodiments, sequence coverage of the genome may be less than about 0.5% of the genome. In some embodiments, sequence coverage of the genome may be less than about 1% of the genome. In some embodiments, sequence coverage of the genome may be less than about 2% of the genome. In some embodiments, sequence coverage of the genome may be less than about 5% of the genome. In some embodiments, sequence coverage of the genome may be at least about 5% of the genome. In some embodiments, sequence coverage of the genome may be at least about 10% of the genome. In some embodiments, sequence coverage of the genome may be at least about 20% of the genome.

Simultaneous sequencing reactions may be performed using multiplex sequencing techniques. In some embodiments, cell-free polynucleotides are sequenced with at least about 1000, 2000, 3000, 4000, 5000, 6000, 7000, 8000, 9000, 10000, 50000, or 100,000 sequencing reactions. In other embodiments, cell-free polynucleotides are sequenced with less than about 1000, 2000, 3000, 4000, 5000, 6000, 7000, 8000, 9000, 10000, 50000, or 100,000 sequencing reactions. Sequencing reactions are typically performed sequentially or simultaneously. Subsequent data analysis is generally performed on all or part of the sequencing reactions. In some embodiments, data analysis is performed on at least about 1000, 2000, 3000, 4000, 5000, 6000, 7000, 8000, 9000, 10000, 50000, or 100,000 sequencing reactions. In other embodiments, data analysis may be performed on less than about 1000, 2000, 3000, 4000, 5000, 6000, 7000, 8000, 9000, 10000, 50000, or 100,000 sequencing reactions. An exemplary read depth is from about 1000 to about 50000 reads per locus (base position) or >50,000 reads per locus.

In some embodiments, a nucleic acid population is prepared for sequencing by enzymatically forming blunt-ends on double-stranded nucleic acids with single-stranded overhangs at one or both ends. In these embodiments, the population is typically treated with an enzyme having a 5'-3' DNA polymerase activity and a 3'-5' exonuclease activity in the presence of the nucleotides (e.g., A, C, G and T or U) in dNTP form. Exemplary enzymes or catalytic fragments thereof that are optionally used include Klenow large fragment and T4 polymerase. At 5' overhangs, the enzyme typically extends the recessed 3' end on the opposing strand until it is flush with the 5' end to produce a blunt end. At 3' overhangs, the enzyme generally digests from the 3' end up to and sometimes beyond the 5' end of the opposing strand. If this digestion proceeds beyond the 5' end of the opposing strand, the gap can be filled in by an enzyme having the same polymerase activity that is used for 5' overhangs. The formation of blunt-ends on double-stranded nucleic acids facilitates, for example, the attachment of adapters and subsequent amplification.

In some embodiments, nucleic acid populations are subject to additional processing, such as the conversion of single-stranded nucleic acids to double-stranded and/or conversion of RNA to DNA. These forms of nucleic acid are also optionally linked to adapters and amplified.

With or without prior amplification, nucleic acids subject to the process of forming blunt-ends described above, and optionally other nucleic acids in a sample, can be sequenced to produce sequenced nucleic acids. A sequenced nucleic acid can refer either to the sequence of a nucleic acid (i.e., sequence information) or a nucleic acid whose sequence has been determined. Sequencing can be performed so as to provide sequence data of individual nucleic acid molecules in a sample either directly or indirectly from a consensus sequence of amplification products of an individual nucleic acid molecule in the sample.

In some embodiments, double-stranded nucleic acids with single-stranded overhangs in a sample after blunt-end formation are linked at both ends to adapters including barcodes, and the sequencing determines nucleic acid sequences as well as in-line barcodes introduced by the adapters. The blunt-end DNA molecules are optionally ligated to a blunt end of an at least partially double-stranded adapter (e.g., a Y shaped or bell-shaped adapter). Alternatively, blunt ends of sample nucleic acids and adapters can be tailed with complementary nucleotides to facilitate ligation (e.g., sticky end ligation).

The nucleic acid sample is typically contacted with a sufficient number of adapters such that there is a low probability (e.g., <1 or <0.1%) that any two identical same nucleic acids receive the same combination of adapter barcodes from the adapters linked at both ends. The use of adapters in this manner permits identification of families of nucleic acid sequences with the same start and stop points on a reference nucleic acid and linked to the same combination of barcodes. Such a family represents sequences of amplification products of a nucleic acid in the sample before amplification. The sequences of family members can be compiled to derive consensus nucleotide(s) or a complete consensus sequence for a nucleic acid molecule in the original sample, as modified by blunt end formation and adapter attachment. In other words, the nucleotide occupying a specified position of a nucleic acid in the sample is determined to be the consensus of nucleotides occupying that corresponding position in family member sequences. Families can include sequences of one or both strands of a double-stranded nucleic acid. If members of a family include sequences of both strands from a double-stranded nucleic acid, sequences of one strand are converted to their complement for purposes of compiling all sequences to derive consensus nucleotide(s) or sequences. Some families include only a single member sequence. In this case, this sequence can be taken as the sequence of a nucleic acid in the sample before amplification. Alternatively, families with only a single member sequence can be eliminated from subsequent analysis.

Nucleotide variations in sequenced nucleic acids can be determined by comparing sequenced nucleic acids with a reference sequence. The reference sequence is often a known sequence, e.g., a known whole or partial genome sequence from a subject (e.g., a whole genome sequence of a human subject). The reference sequence can be, for example, hG19 or hG38. The sequenced nucleic acids can represent sequences determined directly for a nucleic acid in a sample, or a consensus of sequences of amplification products of such a nucleic acid, as described above. A comparison can be performed at one or more designated positions on a reference sequence. A subset of sequenced nucleic acids can be identified including a position corresponding with a designated position of the reference sequence when the respective sequences are maximally aligned. Within such a subset it can be determined which, if any, sequenced nucleic acids include a nucleotide variation at the designated position, and optionally which if any, include a reference nucleotide (i.e., same as in the reference sequence). If the number of sequenced nucleic acids in the subset including a nucleotide variant exceeding a selected threshold, then a variant nucleotide can be called at the designated position. The threshold can be a simple number, such as at least 1, 2, 3, 4, 5, 6, 7, 9, or 10 sequenced nucleic acids within the subset including the nucleotide variant or it can be a ratio, such as a least 0.5, 1, 2, 3, 4, 5, 10, 15, or 20 of sequenced nucleic acids within the subset that include the nucleotide variant, among other possibilities. The comparison can be repeated for any designated position of interest in the reference sequence. Sometimes a comparison can be performed for designated positions occupying at least about 20, 100, 200, or 300 contiguous positions on a reference sequence, e.g., about 20-500, or about 50-300 contiguous positions.

Additional details regarding nucleic acid sequencing, including the formats and applications described herein are also provided in, for example, Levy et al., Annual Review of Genomics and Human Genetics, 17:95-115 (2016), Liu et al., J. of Biomedicine and Biotechnology, Volume 2012, Article ID 251364:1-11 (2012), Voelkerding et al., Clinical Chem., 55:641-658 (2009), MacLean et al., Nature Rev. Microbiol., 7:287-296 (2009), Astier et al., J Am Chem Soc., 128(5): 1705-10 (2006), U.S. Pat. Nos. 6,210,891, 6,258,568, 6,833,246, 7,115,400, 6,969,488, 5,912,148, 6,130,073, 7,169,560, 7,282,337, 7,482,120, 7,501,245, 6,818,395, 6,911,345, 7,501,245, 7,329,492, 7,170,050, 7,302,146, 7,313,308, and 7,476,503, which are each incorporated by reference in their entirety.

Comparator Results

A given subject's microsatellite and/or other repetitive nucleic acid instability status, determined according to the methods disclosed in this application, is typically compared with a database of comparator results from a reference population to identify customized or targeted therapies for that subject. In some embodiments, the test subject's microsatellite and/or other repetitive nucleic acid instability status and comparator results are measured across, for example, the entire genome or entire exome, whereas in other embodiments, those markers are measured based, for example, upon a subset or targeted regions of the genome or exome, which are optionally extrapolated to determine, for example, microsatellite instability for the whole genome or whole exome. Typically, the reference population includes patients with the same cancer type as the test subject and/or patients who are receiving, or who have received, the same therapy as the test subject. In some embodiments, test subject microsatellite and/or other repetitive nucleic acid instability status and comparator microsatellite and/or other repetitive nucleic acid instability status are measured by determining the mutational count or load in a predetermined or selected set of genes or genomic regions. Essentially any gene (e.g., oncogene) is optionally selected for such analysis. In certain of these embodiments, the selected genes or genomic regions include at least about 50, 100, 200, 300, 400, 500, 600, 700, 800, 900, 1000, 1,500, 2,000 or more selected genes or genomic regions. In some of these embodiments, the selected genes or genomic regions optionally include one or more genes listed in Table 1.

TABLE 1

| Point Mutations (SNVs) | | | | | | Amplifications (CNVs) | | Fusions | Indels |
|---|---|---|---|---|---|---|---|---|---|
| AKT1 | ALK | APC | AR | ARAF | ARID1A | AR | BRAF | ALK | EGFR |
| ATM | BRAF | BRCA1 | BRCA2 | CCND1 | CCND2 | CCND1 | CCND2 | FGFR2 | (exons |
| CCNE1 | CDH1 | CDK4 | CDK6 | CDKN2A | CDKN2B | CCNE1 | CDK4 | FGFR3 | 19 & 20) |
| CTNNB1 | EGFR | ERBB2 | ESR1 | EZH2 | FBXW7 | CDK6 | EGFR | NTRK1 | ERBB2 |
| FGFR1 | FGFR2 | FGFR3 | GATA3 | GNAI1 | GNAQ | ERBB2 | FGFR1 | RET | (exons |
| GNAS | HNF1A | HRAS | IDH1 | 1DH2 | JAK2 | FGFR2 | KIT | ROS1 | 19 & 20) |
| JAK3 | KIT | KRAS | MAP2K1 | MAP2K2 | MET | KRAS | MET | | MET |

TABLE 1-continued

| Point Mutations (SNVs) | | | | | | Amplifications (CNVs) | | Fusions | Indels |
|---|---|---|---|---|---|---|---|---|---|
| MLH1 | MPL | MYC | NF1 | NFE2L2 | NOTCH1 | MYC | PDGFRA | | (exon 14 |
| NPM1 | NRAS | NTRK1 | PDGFRA | PIK3CA | PTEN | PIK3CA | RAF1 | | skipping) |
| PTPN11 | RAF1 | RB1 | RET | RHEB | RHOA | | | | |
| RIT1 | ROS1 | SMAD4 | SMO | SRC | STK11 | | | | |
| TERT | TP53 | TSC1 | VHL | | | | | | |

Cancer and Other Diseases

In certain embodiments, the methods and systems disclosed herein are used to identify customized therapies to treat a given disease, disorder or condition in patients. Typically, the disease under consideration is a type of cancer. Non-limiting examples of such cancers include biliary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, Wilms tumor, leukemia, acute lymphocytic leukemia (ALL), acute myeloid leukemia (AML), chronic lymphocytic (CLL), chronic myeloid (CML), chronic myelomonocytic (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T cell lymphomas, non-Hodgkin lymphoma, precursor T-lymphoblastic lymphoma/leukemia, peripheral T cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas. Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma.

Non-limiting examples of other genetic-based diseases, disorders, or conditions that are optionally evaluated using the methods and systems disclosed herein include achondroplasia, alpha-1 antitrypsin deficiency, antiphospholipid syndrome, autism, autosomal dominant polycystic kidney disease, Charcot-Marie-Tooth (CMT), cri du chat, Crohn's disease, cystic fibrosis, Dercum disease, down syndrome, Duane syndrome, Duchenne muscular dystrophy, Factor V Leiden thrombophilia, familial hypercholesterolemia, familial mediterranean fever, fragile X syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency (scid), sickle cell disease, spinal muscular atrophy, Tay-Sachs, thalassemia, trimethylaminuria, Turner syndrome, velocardiofacial syndrome, WAGR syndrome, Wilson disease, or the like.

Customized Therapies and Related Administration

In some embodiments, the methods disclosed herein relate to identifying and administering customized therapies to patients having a given microsatellite and/or other repetitive nucleic acid instability status. Essentially any cancer therapy (e.g., surgical therapy, radiation therapy, chemotherapy, and/or the like) is included as part of these methods. Typically, customized therapies include at least one immunotherapy (or an immunotherapeutic agent). Immunotherapy refers generally to methods of enhancing an immune response against a given cancer type. In certain embodiments, immunotherapy refers to methods of enhancing a T cell response against a tumor or cancer.

In some embodiments, the immunotherapy or immunotherapeutic agents targets an immune checkpoint molecule. Certain tumors are able to evade the immune system by co-opting an immune checkpoint pathway. Thus, targeting immune checkpoints has emerged as an effective approach for countering a tumor's ability to evade the immune system and activating anti-tumor immunity against certain cancers. Pardoll, Nature Reviews Cancer, 2012, 12:252-264.

In certain embodiments, the immune checkpoint molecule is an inhibitory molecule that reduces a signal involved in the T cell response to antigen. For example, CTLA4 is expressed on T cells and plays a role in downregulating T cell activation by binding to CD80 (aka B7.1) or CD86 (aka B7.2) on antigen presenting cells. PD-1 is another inhibitory checkpoint molecule that is expressed on T cells. PD-1 limits the activity of T cells in peripheral tissues during an inflammatory response. In addition, the ligand for PD-1 (PD-L1 or PD-L2) is commonly upregulated on the surface of many different tumors, resulting in the downregulation of anti-tumor immune responses in the tumor microenvironment. In certain embodiments, the inhibitory immune checkpoint molecule is CTLA4 or PD-1. In other embodiments, the inhibitory immune checkpoint molecule is a ligand for PD-1, such as PD-L1 or PD-L2. In other embodiments, the inhibitory immune checkpoint molecule is a ligand for CTLA4, such as CD80 or CD86. In other embodiments, the inhibitory immune checkpoint molecule is lymphocyte activation gene 3 (LAG3), killer cell immunoglobulin like receptor (KIR), T cell membrane protein 3 (TIM3), galectin 9 (GAL9), or adenosine A2a receptor (A2aR).

Antagonists that target these immune checkpoint molecules can be used to enhance antigen-specific T cell responses against certain cancers. Accordingly, in certain embodiments, the immunotherapy or immunotherapeutic agent is an antagonist of an inhibitory immune checkpoint molecule. In certain embodiments, the inhibitory immune checkpoint molecule is PD-1. In certain embodiments, the inhibitory immune checkpoint molecule is PD-L1. In certain embodiments, the antagonist of the inhibitory immune checkpoint molecule is an antibody (e.g., a monoclonal antibody). In certain embodiments, the antibody or monoclonal antibody is an anti-CTLA4, anti-PD-1, anti-PD-L1, or anti-PD-L2 antibody. In certain embodiments, the antibody is a monoclonal anti-PD-1 antibody. In some embodiments, the antibody is a monoclonal anti-PD-L1 antibody. In certain embodiments, the monoclonal antibody is a combination of an anti-CTLA4 antibody and an anti-PD-1 antibody, an anti-CTLA4 antibody and an anti-PD-L1 antibody, or an anti-PD-L1 antibody and an anti-PD-1 antibody. In certain embodiments, the anti-PD-1 antibody is one or more of pembrolizumab (Keytruda®) or nivolumab (Opdivo®). In certain embodiments, the anti-CTLA4 antibody is ipilimumab (Yervoy®). In certain embodiments, the anti-PD-L1 antibody is one or more of atezolizumab (Tecentriq®), avelumab (Bavencio®), or durvalumab (Imfinzi®).

In certain embodiments, the immunotherapy or immunotherapeutic agent is an antagonist (e.g. antibody) against CD80, CD86, LAG3, KIR, TIM3, GAL9, or A2aR. In other embodiments, the antagonist is a soluble version of the inhibitory immune checkpoint molecule, such as a soluble fusion protein comprising the extracellular domain of the inhibitory immune checkpoint molecule and an Fc domain of an antibody. In certain embodiments, the soluble fusion protein comprises the extracellular domain of CTLA4, PD-1, PD-L1, or PD-L2. In some embodiments, the soluble fusion protein comprises the extracellular domain of CD80, CD86, LAG3, KIR, TIM3, GAL9, or A2aR. In one embodiment, the soluble fusion protein comprises the extracellular domain of PD-L2 or LAG3.

In certain embodiments, the immune checkpoint molecule is a co-stimulatory molecule that amplifies a signal involved in a T cell response to an antigen. For example, CD28 is a co-stimulatory receptor expressed on T cells. When a T cell binds to antigen through its T cell receptor, CD28 binds to CD80 (aka B7.1) or CD86 (aka B7.2) on antigen-presenting cells to amplify T cell receptor signaling and promote T cell activation. Because CD28 binds to the same ligands (CD80 and CD86) as CTLA4, CTLA4 is able to counteract or regulate the co-stimulatory signaling mediated by CD28. In certain embodiments, the immune checkpoint molecule is a co-stimulatory molecule selected from CD28, inducible T cell co-stimulator (ICOS), CD137, OX40, or CD27. In other embodiments, the immune checkpoint molecule is a ligand of a co-stimulatory molecule, including, for example, CD80, CD86, B7RP1, B7-H3, B7-H4, CD137L, OX40L, or CD70.

Agonists that target these co-stimulatory checkpoint molecules can be used to enhance antigen-specific T cell responses against certain cancers. Accordingly, in certain embodiments, the immunotherapy or immunotherapeutic agent is an agonist of a co-stimulatory checkpoint molecule. In certain embodiments, the agonist of the co-stimulatory checkpoint molecule is an agonist antibody and preferably is a monoclonal antibody. In certain embodiments, the agonist antibody or monoclonal antibody is an anti-CD28 antibody. In other embodiments, the agonist antibody or monoclonal antibody is an anti-ICOS, anti-CD137, anti-OX40, or anti-CD27 antibody. In other embodiments, the agonist antibody or monoclonal antibody is an anti-CD80, anti-CD86, anti-B7RP1, anti-B7-H3, anti-B7-H4, anti-CD137L, anti-OX40L, or anti-CD70 antibody.

Therapeutic options for treating specific genetic-based diseases, disorders, or conditions, other than cancer, are generally well-known to those of ordinary skill in the art and will be apparent given the particular disease, disorder, or condition under consideration.

In certain embodiments, the customized therapies described herein are typically administered parenterally (e.g., intravenously or subcutaneously). Pharmaceutical compositions containing the immunotherapeutic agent are typically administered intravenously. Certain therapeutic agents are administered orally. However, customized therapies (e.g., immunotherapeutic agents, etc.) may also be administered by any method known in the art, including, for example, buccal, sublingual, rectal, vaginal, intraurethral, topical, intraocular, intranasal, and/or intraauricular, which administration may include tablets, capsules, granules, aqueous suspensions, gels, sprays, suppositories, salves, ointments, or the like.

Systems and Computer Readable Media

Figure 2:
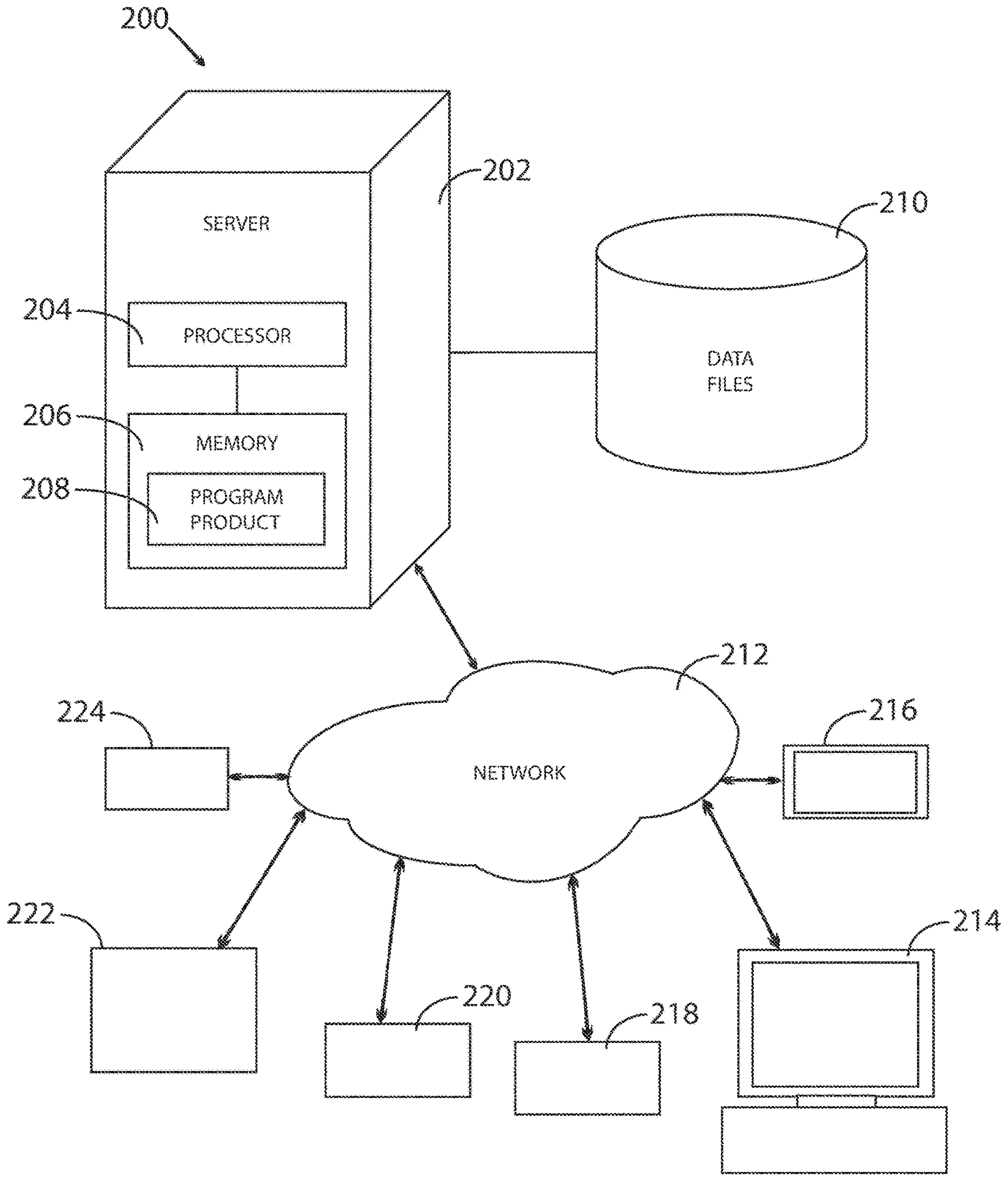
FIG. 2 is a schematic diagram of an exemplary system suitable for use with certain embodiments of the invention.

The present disclosure also provides various systems and computer program products or machine readable media. In some embodiments, for example, the methods described herein are optionally performed or facilitated at least in part using systems, distributed computing hardware and applications (e.g., cloud computing services), electronic communication networks, communication interfaces, computer program products, machine readable media, electronic storage media, software (e.g., machine-executable code or logic instructions) and/or the like. To illustrate, FIG. 2 provides a schematic diagram of an exemplary system suitable for use with implementing at least aspects of the methods disclosed in this application. As shown, system 200 includes at least one controller or computer, e.g., server 202 (e.g., a search engine server), which includes processor 204 and memory, storage device, or memory component 206, and one or more other communication devices 214 and 216 (e.g., client-side computer terminals, telephones, tablets, laptops, other mobile devices, etc.) positioned remote from and in communication with the remote server 202, through electronic communication network 212, such as the internet or other internetwork. Communication devices 214 and 216 typically include an electronic display (e.g., an internet enabled computer or the like) in communication with, e.g., server 202 computer over network 212 in which the electronic display comprises a user interface (e.g., a graphical user interface (GUI), a web-based user interface, and/or the like) for displaying results upon implementing the methods described herein. In certain embodiments, communication networks also encompass the physical transfer of data from one location to another, for example, using a hard drive, thumb drive, or other data storage mechanism. System 200 also includes program product 208 stored on a computer or machine readable medium, such as, for example, one or more of various types of memory, such as memory 206 of server 202, that is readable by the server 202, to facilitate, for example, a guided search application or other executable by one or more other communication devices, such as 214 (schematically shown as a desktop or personal computer) and 216 (schematically shown as a tablet computer). In some embodiments, system 200 optionally also includes at least one database server, such as, for example, server 210 associated with an online website having data stored thereon (e.g., control sample or comparator result data, indexed customized therapies, etc.) searchable either directly or through search engine server 202. System 200 optionally also includes one or more other servers positioned remotely from server 202, each of which are optionally associated with one or more database servers 210 located remotely or located local to each of the other servers. The other servers can beneficially provide service to geographically remote users and enhance geographically distributed operations.

As understood by those of ordinary skill in the art, memory 206 of the server 202 optionally includes volatile and/or nonvolatile memory including, for example, RAM, ROM, and magnetic or optical disks, among others. It is also understood by those of ordinary skill in the art that although illustrated as a single server, the illustrated configuration of server 202 is given only by way of example and that other types of servers or computers configured according to various other methodologies or architectures can also be used. Server 202 shown schematically in FIG. 2, represents a server or server cluster or server farm and is not limited to any individual physical server. The server site may be deployed as a server farm or server cluster managed by a server hosting provider. The number of servers and their architecture and configuration may be increased based on usage, demand and capacity requirements for the system 200. As also understood by those of ordinary skill in the art, other user communication devices 214 and 216 in these embodiments, for example, can be a laptop, desktop, tablet, personal digital assistant (PDA), cell phone, server, or other types of computers. As known and understood by those of ordinary skill in the art, network 212 can include an internet, intranet, a telecommunication network, an extranet, or world wide web of a plurality of computers/servers in communication with one or more other computers through a communication network, and/or portions of a local or other area network.

As further understood by those of ordinary skill in the art, exemplary program product or machine readable medium 208 is optionally in the form of microcode, programs, cloud computing format, routines, and/or symbolic languages that provide one or more sets of ordered operations that control the functioning of the hardware and direct its operation. Program product 208, according to an exemplary embodiment, also need not reside in its entirety in volatile memory, but can be selectively loaded, as necessary, according to various methodologies as known and understood by those of ordinary skill in the art.

As further understood by those of ordinary skill in the art, the term "computer-readable medium" or "machine-readable medium" refers to any medium that participates in providing instructions to a processor for execution. To illustrate, the term "computer-readable medium" or "machine-readable medium" encompasses distribution media, cloud computing formats, intermediate storage media, execution memory of a computer, and any other medium or device capable of storing program product 208 implementing the functionality or processes of various embodiments of the present disclosure, for example, for reading by a computer. A "computer-readable medium" or "machine-readable medium" may take many forms, including but not limited to, non-volatile media, volatile media, and transmission media. Non-volatile media includes, for example, optical or magnetic disks. Volatile media includes dynamic memory, such as the main memory of a given system. Transmission media includes coaxial cables, copper wire and fiber optics, including the wires that comprise a bus. Transmission media can also take the form of acoustic or light waves, such as those generated during radio wave and infrared data communications, among others. Exemplary forms of computer-readable media include a floppy disk, a flexible disk, hard disk, magnetic tape, a flash drive, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave, or any other medium from which a computer can read.

Program product 208 is optionally copied from the computer-readable medium to a hard disk or a similar intermediate storage medium. When program product 208, or portions thereof, are to be run, it is optionally loaded from their distribution medium, their intermediate storage medium, or the like into the execution memory of one or more computers, configuring the computer(s) to act in accordance with the functionality or method of various embodiments. All such operations are well known to those of ordinary skill in the art of, for example, computer systems.

To further illustrate, in certain embodiments, this application provides systems that include one or more processors, and one or more memory components in communication with the processor. The memory component typically includes one or more instructions that, when executed, cause the processor to provide information that causes sequence information, microsatellite and/or other repetitive nucleic acid instability status, comparator results, customized therapies, and/or the like to be displayed (e.g., via communication devices 214, 216, or the like) and/or receive information from other system components and/or from a system user (e.g., via communication devices 214, 216, or the like).

In some embodiments, program product 208 includes non-transitory computer-executable instructions which, when executed by electronic processor 204 perform at least: (i) receiving sequence information from a population of microsatellite loci in a sample, (ii) quantifying a number of different repeat lengths present at each of a plurality of the microsatellite loci from the sequence information to generate a site score for each of the plurality of the microsatellite loci, (iii) comparing the site score of a given microsatellite locus to a site specific trained threshold for the given microsatellite locus for each of the plurality of the microsatellite loci, (iv) calling the given microsatellite locus as being unstable when the site score of the given microsatellite locus exceeds the site specific trained threshold for the given microsatellite locus to generate a microsatellite instability score comprising a number of unstable microsatellite loci from the plurality of the microsatellite loci, (v) classifying the MSI status of the sample as being unstable when the microsatellite instability score exceeds a population trained threshold for the population of microsatellite loci in the sample to identify an unstable sample, and optionally (vi) comparing the microsatellite instability score of the unstable sample to one or more comparator results in which a substantial match between the microsatellite instability score of the unstable sample and the comparator results indicates a predicted response to therapy for the subject.

System 200 also typically includes additional system components that are configured to perform various aspects of the methods described herein. In some of these embodiments, one or more of these additional system components are positioned remote from and in communication with the remote server 202 through electronic communication network 212, whereas in other embodiments, one or more of these additional system components are positioned local, and in communication with server 202 (i.e., in the absence of electronic communication network 212) or directly with, for example, desktop computer 214.

In some embodiments, for example, additional system components include sample preparation component 218 is operably connected (directly or indirectly (e.g., via electronic communication network 212)) to controller 202. Sample preparation component 218 is configured to prepare the nucleic acids in samples (e.g., prepare libraries of nucleic acids) to be amplified and/or sequenced by a nucleic acid amplification component (e.g., a thermal cycler, etc.) and/or a nucleic acid sequencer. In certain of these embodiments, sample preparation component 218 is configured to isolate nucleic acids from other components in a sample, to attach one or adapters comprising barcodes to nucleic acids as described herein, selectively enrich one or more regions from a genome or transcriptome prior to sequencing, and/or the like.

In certain embodiments, system 200 also includes nucleic acid amplification component 220 (e.g., a thermal cycler, etc.) operably connected (directly or indirectly (e.g., via electronic communication network 212)) to controller 202. Nucleic acid amplification component 220 is configured to amplify nucleic acids in samples from subjects. For example, nucleic acid amplification component 220 is optionally configured to amplify selectively enriched regions from a genome or transcriptome in the samples as described herein.

System 200 also typically includes at least one nucleic acid sequencer 222 operably connected (directly or indirectly (e.g., via electronic communication network 212)) to controller 202. Nucleic acid sequencer 222 is configured to provide the sequence information from nucleic acids (e.g., amplified nucleic acids) in samples from subjects. Essentially any type of nucleic acid sequencer can be adapted for use in these systems. For example, nucleic acid sequencer 222 is optionally configured to perform pyrosequencing, single-molecule sequencing, nanopore sequencing, semiconductor sequencing, sequencing-by-synthesis, sequencing-by-ligation, sequencing-by-hybridization, or other techniques on the nucleic acids to generate sequencing reads. Optionally, nucleic acid sequencer 222 is configured to group sequence reads into families of sequence reads, each family comprising sequence reads generated from a nucleic acid in a given sample. In some embodiments, nucleic acid sequencer 222 uses a clonal single molecule array derived from the sequencing library to generate the sequencing reads. In certain embodiments, nucleic acid sequencer 222 includes at least one chip having an array of microwells for sequencing a sequencing library to generate sequencing reads.

To facilitate complete or partial system automation, system 200 typically also includes material transfer component 224 operably connected (directly or indirectly (e.g., via electronic communication network 212)) to controller 202. Material transfer component 224 is configured to transfer one or more materials (e.g., nucleic acid samples, amplicons, reagents, and/or the like) to and/or from nucleic acid sequencer 222, sample preparation component 218, and nucleic acid amplification component 220.

Additional details relating to computer systems and networks, databases, and computer program products are also provided in, for example, Peterson, Computer Networks: A Systems Approach, Morgan Kaufmann, $5^{th}$ Ed. (2011), Kurose, Computer Networking: A Top-Down Approach, Pearson, $7^{th}$ Ed. (2016), Elmasri, Fundamentals of Database Systems, Addison Wesley, 6th Ed. (2010), Coronel, Database Systems: Design, Implementation, & Management, Cengage Learning, $11^{th}$ Ed. (2014), Tucker, Programming Languages, McGraw-Hill Science/Engineering/Math, 2nd Ed. (2006), and Rhoton, Cloud Computing Architected: Solution Design Handbook, Recursive Press (2011), which are each incorporated by reference in their entirety.

EXAMPLES

Example 1

MSI high (MSI-H) samples were computationally simulated with variable tumor fractions and numbers of unstable sites using non-tumor samples as background. The distribution observed in a cohort of 3000 samples of different cancer types was used as a prior for the number of unstable sites. This analysis demonstrated a sensitivity of 94% at limit of detection (LoD) of 0.2% of tumor content. The expected specificity of the method to determine MSI status according to an embodiment described herein on non-tumor donor samples was 99.999%. Comparison of these results against standard or conventional PCR-based MSI assessment showed 100% concordance across a tumor content range of 1.4%-15%. Additionally, the performance of this analysis was tested on 155 clinical samples from three cancer types, for which standard PCR-based assessment of MSI status was available (10 MSI-H, 145 microsatellite stable (MSS)). The MSI calls generated according to an embodiment described herein showed 100% concordance with the standard PCR-based MSI assessment.

Example 2

The MSI status of 82 samples was evaluated using the Digital Sequencing clinical platform (Guardant Health, Inc., Redwood City, CA, USA). Digital Sequencing platform is an NGS panel of cancer-related genes utilizing high-quality sequencing of cell-free DNA (which could comprise circulating tumor DNA) isolated from a simple, non-invasive blood draw. Digital Sequencing employs pre-sequencing preparation of a digital library of individually tagged cfDNA molecules combined with post-sequencing bioinformatic reconstruction to eliminate nearly all false positives. Sequence information was obtained using targeted sequencing of cfDNA in the samples. Sites scores (ΔAIC) were determined for 61 of the most informative microsatellite loci in each sample. The tumor fraction of samples ranged from 0.5% to 15%. The site scores were compared with corresponding site specific trained thresholds for each sample to identify the number of unstable microsatellite loci in each sample. The number of unstable microsatellite loci identified in a given sample was used as the microsatellite instability score (i.e., MSI sample score) for that particular sample. A population trained threshold for the 61 microsatellite loci in the samples was determined in which a microsatellite instability score that was greater than or equal to five was predicted to classify a sample as being MSI-High (MSI-H), whereas a microsatellite instability score that was less than or equal to four was predicted to classify a sample as being microsatellite stable (MSS). Nine of the 82 samples were classified as being MSI-H. The remaining 73 samples were classified as being MSS. In all of the 82 samples, the predicted stability status matched the expected stability status. MSI status was confirmed based on orthogonal validation.

Example 3

Introduction

Microsatellite instability (MSI) is a guideline-recommended biomarker with prognostic significance in a variety of tumor types as well as predictive significance for treatment with immune checkpoint inhibitors. Traditionally, microsatellite instability detection has relied on testing tumor tissue by PCR or immunohistochemistry. More recently, next generation sequencing (NGS) methods have been developed that also rely on availability of tumor tissue. In contrast, a plasma-based MSI detection method could provide non-invasive, real-time assessment of MSI status. Guardant Health's large panel cell-free DNA (cfDNA) NGS assay assesses 500 cancer-associated genes to identify genomic alterations and tumor mutation burden (TMB). In addition to single nucleotide variants (SNVs), indels, copy number amplifications (CNAs), fusions, and TMB, the panel can detect microsatellite instability high (MSI-high) status based on somatic changes in >1,000 MSI sites. The analytical validation presented in this example has four main components that serve to determine the performance of the 500 cancer-associated gene cfDNA NGS assay for MSI-high detection: accuracy, limit of detection (LoD), precision, and Limit of Blank (LoB).

Methods

Accuracy analysis used 258 samples from 3 sources with MSI status predicted by 500 cancer-associated gene cfDNA NGS assay compared with truth based on tissue MSI status determined with an orthogonal method. 36 collaborator samples with tissue MSI status (truth: tissue MSI status), 121 healthy donors (truth: microsatellite stable, MSS), and 101 samples sequenced by 500 cancer-associated gene cfDNA NGS assay (large panel assay) and 73 cancer-associated gene cfDNA NGS assay (small panel assay, MSI status as truth) were used. Reproducibility and repeatability analysis used 2 sets of replicates (56 replicates in total). MSI status and MSI scores were compared within run and between run. LoD was obtained both by simulation. LoB was calculated using healthy donor samples and known MSS samples.

Results

1. Accuracy Analysis

Among 13 MSI high samples based on tissue MSI status, 12 were called MSI-High by the large panel assay. All MSS/MSI-low (MSI-L) samples were correctly detected (Table 2). When restricted to the microsatellite regions covered by the small panel assay (~90 sites), the 12 samples detected as MSI-high by the large panel assay also met the small panel assay thresholds for being called MSI-high.

TABLE 2

| | | TRUTH | | |
|---|---|---|---|---|
| | | MSI-H | MSS/MSI-L | |
| Large Panel Assay | MSI-H | 12 | 0 | PPV = 100% |
| | MSS/MSI-L | 1 | 245 | NPV = 99.6% |
| | | Sensitivity = 92.3% | Specificity = 100% | 258 (total) |

2. LoD Analysis

Figure 3:
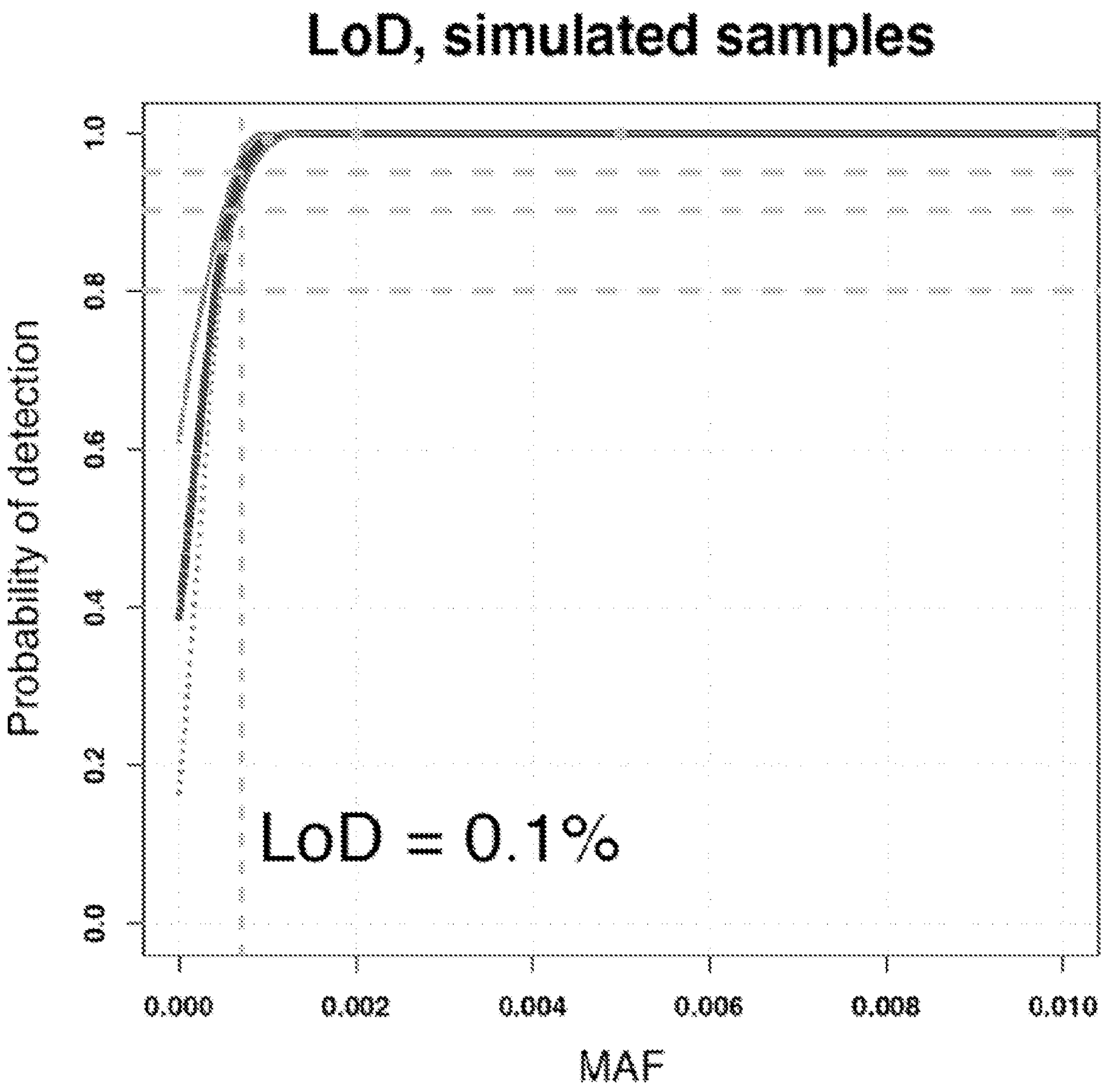
FIG. 3 is a plot of limit of detection (LoD) for simulated samples (probability of detection (y-axis); mutant allele fraction (MAF) (x-axis)).

Simulation on the >1,000 sites used to detect MSI across five tumor fractions ranging from 0.05% to 1% indicates a LoD of 0.1% (FIG. 3).

Figure 4A:
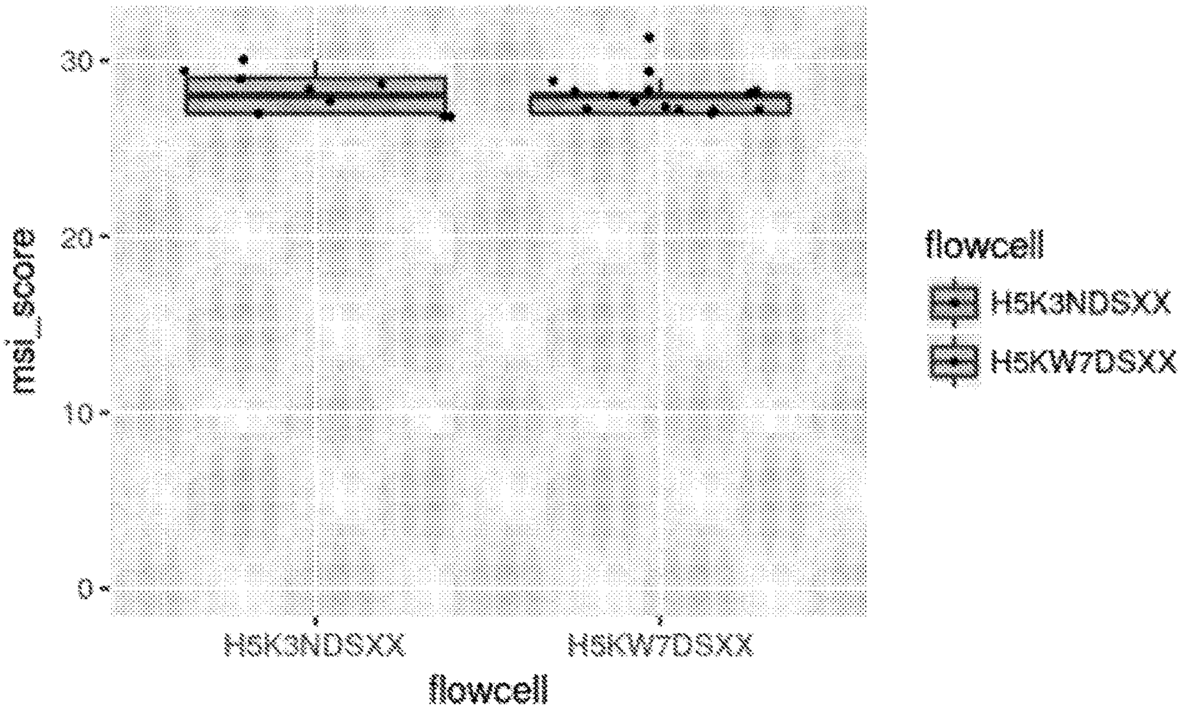
FIG. 4A (MSI score (y-axis); flowcell (x-axis)) and 4B (MSI score (y-axis); reference sample (x-axis)) are plots of data from repeatability and reproducibility analysis.
Figure 4B:
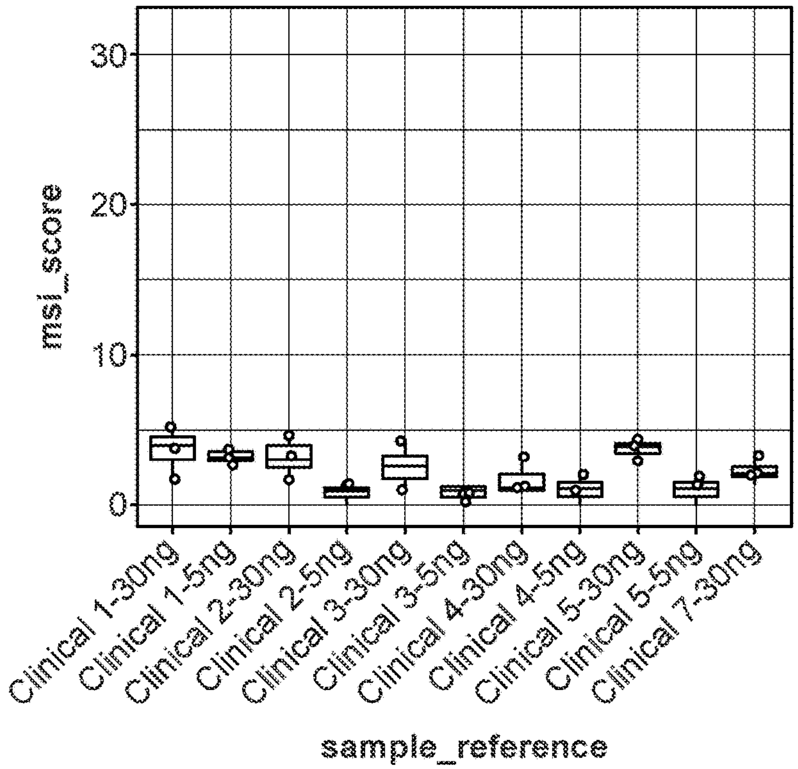

3. MSI-High Detection with 500 Cancer-Associated Gene cfDNA NGS Assay is Replicable and Repeatable 24 MSI-high replicates were tested in two runs. All replicates were detected as MSI-high with 500 cancer-associated gene cfDNA NGS assay. MSI numeric scores are ±4 within and between runs (FIG. 4A). 10 MSS/MSI low samples have 2-3 replicates (32 replicates in total) tested in the same flow cell. All replicates are detected as MSS/MSI low with 500 cancer-associated gene cfDNA NGS assay. MSI scores are ±3 within each sample (FIG. 4B).

4. LoB Analysis 121 healthy donors and 25 collaborator samples with known MSS status were used in LoB analysis. All 146 samples were correctly classified as MSS/MSI low with large panel assay, showing a false positive rate as 0%.

5. Tumor Fraction with MSI Scores

Figure 5A:
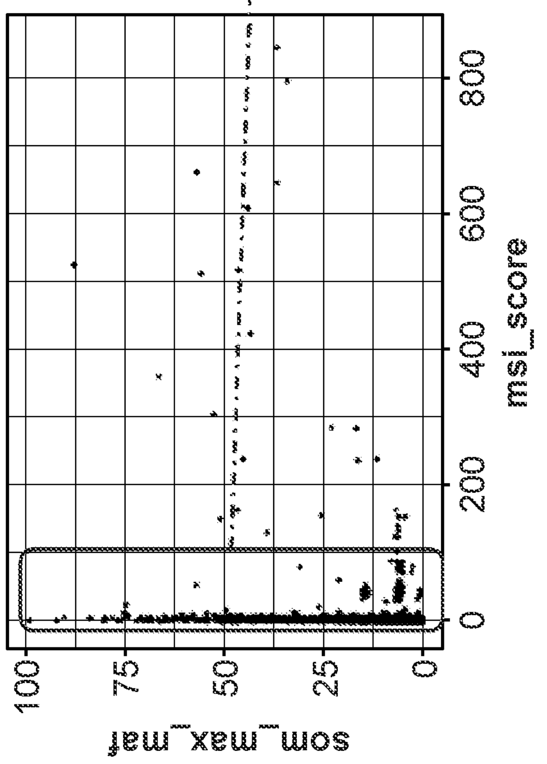
FIG. 5A (somatic max-MAF (y-axis); MSI score (x-axis)) and 5B (somatic max-MAF (y-axis); MSI score (x-axis)) are plots showing that tumor fraction does not correlate with MSI scores.
Figure 5B:
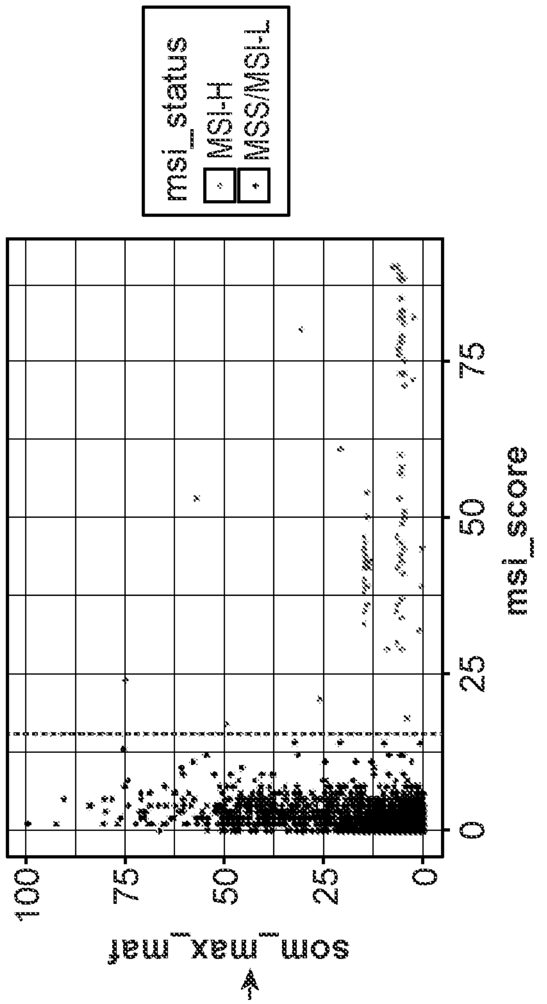

MSI scores are plotted vs max mutant allele fraction (MAF) of somatic calls (FIGS. 5A and B) in more than 2,000 large panel assay samples showing that tumor fraction (as measured by MAF) did not correlate with MSI status.

Conclusions

MSI high detection with 500 cancer-associated gene cfDNA NGS assay showed high sensitivity (>90%) and specificity (100%). Repeatability and reproducibility within and across runs were high. LoD of MSI high detection was 0.1% MAF. LoB study showed the false positive rate of 0%. 500 cancer-associated gene cfDNA NGS assay provides a reliable prediction of MSI high status with cfDNA, which will give treatment values to physicians, without the need of tissue samples.

Example 4

Introduction

Microsatellite instability (MSI) is a National Comprehensive Cancer Network (NCCN) clinical practice guidelines-recommended biomarker in at least nine cancer types—cervical, cholangiocarcinoma, colorectal, endometrial, esophageal and esophagogastric, gastric, ovarian, pancreatic, and prostate cancers (1-9)—due to its importance as a predictive biomarker for response to immune checkpoint blockade (ICB) as exemplified by pan-cancer approval of pembrolizumab (10,11). Detection of MSI in a patient with advanced cancer can also alert the clinician to evaluate the patient's asymptomatic family members for hereditary cancer risk.

MSI is the archetypical manifestation of defective DNA mismatch repair (dMMR), which leads to dramatically increased mutation rates throughout the genome, including gain and/or loss of nucleotides within repeating motifs known as microsatellite tracts, from which the entity derives its name. MSI is most prevalent in endometrial, colorectal, and gastroesophageal cancers, where it can be a sequela of sporadic mutations in MMR-related genes or a manifestation of Lynch syndrome, a hereditary cancer predisposition syndrome most commonly caused by germline mutations in MLH1, MSH2, MSH6, PMS2, or EPCAM (12). However, despite an increased prevalence in these cancer types, landscape analyses have shown that MSI also occurs at non-negligible rates in most other solid tumors, including common tumor types such as lung, prostate, and breast cancer (13).

Recent studies have shown that MSI predicts clinical benefit from ICB with PD-1/PD-L1 inhibitors, which has led to the approval of these agents in several indications when MSI is present, including nivolumab±ipilimumab for MSI-High (MSI-H, positive for MSI) metastatic colorectal cancer and pembrolizumab for unresectable or metastatic MSI-H solid tumors following progression on prior approved therapies (14). In addition to its value as a predictive biomarker for ICB benefit, MSI also has prognostic significance, most notably in colorectal cancer (CRC), where testing is recommended in clinical practice guidelines for all patients (3,15).

Currently, MSI testing is most commonly performed via polymerase chain reaction (PCR) and/or immunohistochemistry (IHC) analysis of tumor tissue specimens. The former assesses five canonical microsatellite loci originally recommended by the Bethesda panel (16,17) and compares their length in tumor DNA relative to the germline genotype assessed in matched non-tumor DNA; instability in the length of each microsatellite tract is used as direct evidence of MSI. However, this limited microsatellite panel was developed primarily for CRC and has more limited sensitivity in other cancer types (18). IHC approaches, in contrast, assess levels of four MMR proteins, with absence of expression of one or more (deficient MMR, dMMR) strongly correlated with MSI status. However, about 5% to 11% of MSI-H cases demonstrate intact MMR staining and localization (proficient MMR, pMMR) due to retained antigenicity and intracellular trafficking of an otherwise nonfunctional protein (19). Recent publications (20,21) have demonstrated that next-generation sequencing (NGS) can also accurately characterize MSI status in tumors, allowing for comprehensive profiling of targetable genomic biomarkers as well as MSI status via a single NGS test.

Despite recommendations across many cancer types in NCCN guidelines and associated FDA-approved treatment options, current rates of MSI testing outside of CRC and gastroesophageal carcinoma remain very low (22). Even in CRC, where MSI testing recommendations have been in place since 2005 (17,23), fewer than 50% of patients are tested (24), which results in missed ICB treatment opportunities and failure to recognize patients whose family members may be at increased risk for cancer. While multifactorial, such MSI undergenotyping is often due to barriers associated with tissue acquisition and complex testing recommendations/algorithms. For example, testing of archival diagnostic specimens can incur significant delays associated with locating and obtaining this material and result in inaccurate assessment of MSI status due to tumor evolution and/or heterogeneity. Similarly, testing of newly-obtained tissue specimens can also result in significant delays associated with biopsy scheduling and failure and is additionally associated with risk and cost due to procedure complications. As such, invasive tissue acquisition procedures are contraindicated in many heavily pre-treated and/or frail patients. Additionally, the rapidly growing number of biomarkers and diversification of testing options creates daunting complexity for already over-burdened physicians.

Cell-free circulating-tumor DNA (ctDNA) assays ("liquid biopsies") have successfully addressed such barriers in many genotyping indications by enabling minimally-invasive profiling of contemporaneous tumor DNA. Liquid biopsies thus expand patient access to standard-of-care targeted therapies, including ICBs, by identifying patients whose tumors harbor biomarkers of interest not otherwise identifiable due to tissue sampling limitations and do so more rapidly than typical tissue testing (25). Moreover, comprehensive liquid biopsies can provide all guideline recommended somatic genomic biomarker information for all adult solid tumors in a single test. In this study, it was sought to enhance the utility of a previously validated ctDNA-based genotyping test through the addition of MSI detection. Here is described the design and validation of MSI assessment on this platform, report its performance on the largest ctDNA-tissue MSI validation cohort yet described (n=1145) and evaluate response prediction in 16 advanced gastric cancer patients treated with ICB. Also reported here is the MSI-H landscape of more than 28,000 consecutive solid tumor patients tested in a Clinical Laboratory Improvement Amendment (CLIA)-certified, College of American Pathologists (CAP)-accredited, New York State Department of Health-approved laboratory.

Materials and Methods

1. Microsatellite Loci Selection

Guardant Health's small panel cell-free DNA (cfDNA) NGS assay is a 74-gene panel previously validated for detection of SNVs, indels, CNAs, and fusions in all guideline-recommended indications for advanced solid tumors (26,27). The assay initially incorporated 99 putative microsatellite loci consisting of short tandem repeats (STRs) of length 7 or more, which were selected to include sites susceptible to instability across multiple tumor types, including three of the five Bethesda panel sites (BAT-25, BAT-26, and NR-21). The remaining two Bethesda sites (NR-24 and MONO-27) were not included due to extremely low mappability of the regions. Coverage and noise profiles at these sites were assessed using sequencing data from a set of 84 healthy donor samples, to exclude uninformative sites from the final MSI detection algorithm.

2. Model Description

MSI detection is based on integrating observed read sequences with molecular barcoding information into a single probabilistic model that compares the likelihood of observed data under PCR and sequencing noise assumptions with that under somatic MSI instability assumption. Each of the individual sites is scored independently using Akaike Information Criterion (AIC) (28). The AIC model generates a locus score (ranging from 0 to infinity), reflecting the likelihood that observed variability at any given microsatellite locus is due to biological instability vs. noise, and a locus is considered unstable if its score (i.e., site score) is above a site specific trained threshold. The number of affected loci is calculated across the final 90 sites and the sample is called positive if the number of unstable loci (the "MSI Score") is above a population trained threshold (n=6). The thresholds for individual loci and total MSI score per sample were established using permutation-based simulations with data from healthy donor samples varying the frequencies of molecules with different repeat lengths and the error parameters at individual loci, as well as the overall number of unstable loci within a simulated sample. Through this approach, simulations were used here in order to interrogate 100,000 combinations of microsatellite lengths and unstable locus numbers, which allows assessment of a diverse landscape of scenarios, some of which may not be represented in a non-simulated dataset. The algorithm does not distinguish between microsatellite stable (MSS) and MSI-Low (a category defined by the observation of a single unstable Bethesda locus using PCR methods), grouping them into a single category. This is based on previous reports that MSI-L status is not a distinct phenotype but an artifact of testing a small number of microsatellites, such that when a large number of microsatellite loci are tested, previously characterized MSI-L samples mimic the MSS phenotype in overall MSI burden.

3. Samples

MSI algorithm development and training was performed using simulated data as well as a set of 84 healthy donor samples. The clinical validation study included 1145 archived samples (residual plasma and/or cell-free DNA) collected and processed as part of routine standard of care clinical testing in the Guardant Health CLIA laboratory as previously described (26), or archival patient plasma samples collected in EDTA blood collection tubes. Twenty healthy donor samples were also used for the analytical specificity study. Contrived samples used in the analytical validation studies comprise cfDNA pools extracted from cell line supernatants and healthy donor plasma. Cell-free DNA prepared from culture supernatants from the following cell lines were used (ATCC, Inc.): KM12, NCI-H660, HCC1419, NCI-H2228, NCI-H1650, NCI-H1648, NCI-H1975, NCI-H1993, NCIH596, HCC78, GM12878, MCF-7. cfDNA isolated from cell line culture supernatant mimics the fragment size and mechanisms of extracellular release (29), library conversion, and sequencing properties of patient-derived cfDNA, while also providing a renewable source of well-defined material of sufficient quantity to support the high material demands of studies such as limit of detection and precision.

4. Sample Processing and Bioinformatics Analysis

Cell-free DNA was extracted from plasma samples or cell line supernatants (QIAmp Circulating Nucleic Acid Kit, Qiagen, Inc.), and up to 30 ng of extracted cfDNA was labeled with non-random oligonucleotide barcodes (IDT, Inc.), followed by library preparation, hybrid capture enrichment (Agilent Technologies, Inc.), and sequencing by paired-end synthesis (NextSeq 500/550 or HiSeq 2500, Illumina, Inc.) as previously described (26). Bioinformatics analysis and variant detection were performed as previously described (26).

5. Analytical Validation Approach

The studies performed for analytical validation were based on established CLIA, Nex-StoCT Working Group, and Association of Molecular Pathologists/CAP guidance regarding performance characteristics and validation principles. To determine the sensitivity of the assay for MSI status, cfDNA from cell line supernatant from an MSI-H cell line (KM12) (29) was diluted with cfDNA from a microsatellite stable (MSS) cell line (NCI-H660) (30,31) and tested at both standard (30 ng) and low (5 ng) cfDNA inputs. The dilution series targeted maximal mutant allele fractions (max MAFs) of 0.03-2% for 5 ng input, and 0.01-1% for 30 ng input. Targeted tumor fractions were verified using known germline variants unique to the titrant and diluent materials. Assessment of repeatability (within-run precision) and reproducibility (between-run precision) was based on clinical and contrived model samples. Six of the clinical samples for precision (three MSI-H, and three MSS) were selected with max MAF values of 1-2%, representing ~2-3× the predicted LoD at 5 ng. MSI analytical specificity was determined by analyzing 20 healthy donor samples and 245 known MSS contrived samples.

6. Clinical Validation Approach

Archived plasma or cfDNA from clinical samples from patients with available results from standard of care tissue-based MSI testing were tested using the ctDNA MSI algorithm (n=1145). Tissue-based MSI status was derived from IHC, PCR, or, less commonly, NGS. Clinical outcome data were extracted from patient medical records and deidentified by the treating physician.

7. Landscape Analysis of Plasma MSI status from 28,459 Advanced Cancer Patient Samples The cohort comprised 28459 consecutive advanced cancer patient samples tested using the 73 cancer-associated gene cfDNA NGS assay (small panel assay) in the course of their clinical care. All analyses were conducted with de-identified data and according to an IRB-approved protocol. The prevalence of MSI-H in this cohort was assessed across 16 primary tumor types: bladder carcinoma, breast carcinoma, cholangiocarcinoma, colon adenocarcinoma, cancer of unknown primary, head and neck squamous cell carcinoma, hepatocellular carcinoma, lung adenocarcinoma, lung cancer not otherwise specified, lung squamous cell carcinoma, "other" cancer diagnosis, pancreatic adenocarcinoma, prostate adenocarcinoma, stomach adenocarcinoma, and uterine endometrial carcinoma.

8. Statistics

Statistical analyses were performed using Student's t-test for analysis of number of variants per sample and Fisher exact test for comparison of proportions. The lower and upper limits of the 95% confidence intervals (CI) for binomial proportions were calculated using Wilson's score interval with continuity correction.

9. Ethics

This research was conducted utilizing deidentified data as per a protocol approved by the Quorum Institutional Review Board.

Results

1. MSI Algorithm Development

Traditional challenges for ctDNA genotyping using NGS include efficient molecule capture due to low inputs and low tumor fraction in circulation (26,27) and correction of sequencing and other technical artifacts. MSI detection presents additional challenges due to the need for 1) efficient molecular capture, sequencing, and mapping of repetitive genomic regions that accurately reflect MSI status; 2) error correction and variant detection within repetitive regions; and 3) differentiation of signal due to MSI from non-MSI somatic variation and the strong PCR slippage artifacts at sites typically impacted by somatic instability. Indeed, technical PCR error is typically at least an order of magnitude higher than typical sequencing error rates in homopolymeric sites, necessitating iterative site selection and optimal use of molecular barcoding to achieve relevant signal-to-noise detection ratios across a large number of candidate microsatellite sites.

While tissue sequencing panels often comprise sufficient informative microsatellite loci simply due to large panel size and longer DNA fragment lengths (13,32), the moderate size of the ctDNA panel utilized here and short cell-free DNA (cfDNA) fragment lengths require purposeful microsatellite selection and inclusion. To accomplish this, an iterative approach was used informed by literature and tissue sequencing compendia to evaluate candidate sites to provide pan-cancer MSI detection with minimal background noise. The list of candidate loci was further refined based on the performance criteria referenced above using healthy donor cfDNA.

Figure 6A:
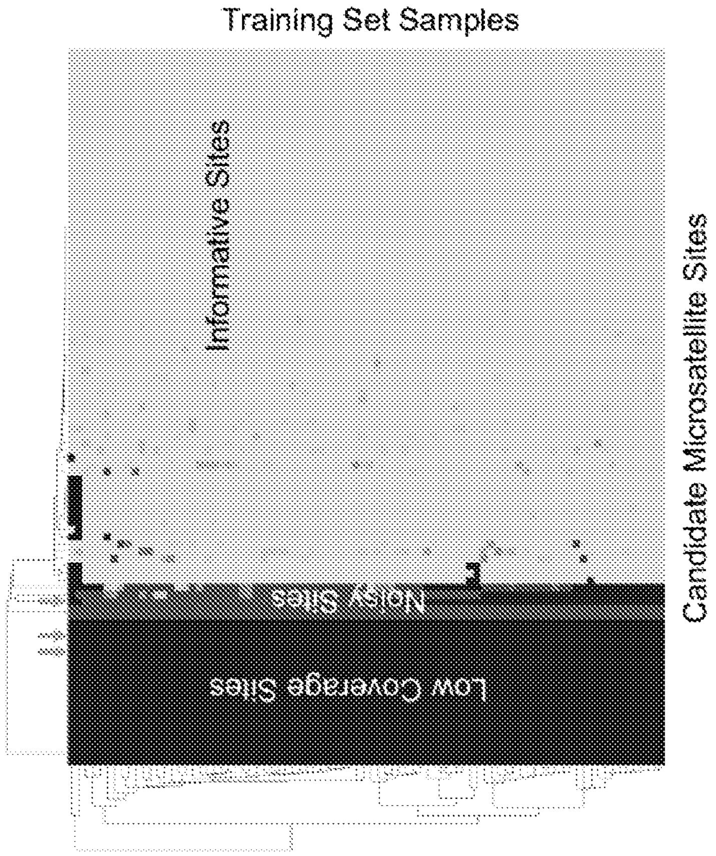
FIGS. 6A and 6B are plots showing technical features of microsatellite detection.

Based on the performance assessment in training healthy donor samples, informative loci were defined as those that were effectively captured, sequenced, and mapped and were associated with little variation within MSS samples (shown in light gray in FIG. 6A). Uninformative loci either failed capture, sequencing, or mapping, resulting in inadequate molecular representation (shown in black in FIG. 6A), or demonstrated substantial variation within MSS samples, resulting in excessive artifactual signal (shown in dark grey in FIG. 6A). Interestingly, the BAT-25, BAT-26, and NR-21 Bethesda loci utilized in traditional MSI tissue tests (16,17) and some ctDNA panels (33) performed poorly relative to other candidates and were excluded from the final marker set (indicated by arrows in FIG. 6A).

Using this approach, 90 microsatellite loci were selected for inclusion in the final test version: 89 mononucleotide repeats and a single trinucleotide repeat, all of which comprise repeat lengths of 7 or above. Assessment of unique molecule coverage distribution demonstrated that 65% of these loci have coverage above 0.5× median sample coverage.

In addition to effective molecular capture and mapping, MSI detection also entails highly accurate differentiation of cancer-related signal from background noise due to sequencing and polymerase errors at the very low allele fractions at which ctDNA is typically found (26,27,34). Importantly, the same repetitive genomic context that makes microsatellite candidates informative for MSI detection due to polymerase slippage during in vivo cellular replication also makes them particularly susceptible to the same polymerase slippage during in vitro library preparation and sequencing, resulting in high levels of technical noise. To address this, Digital Sequencing error correction was used to define true biological insertion-deletion events at microsatellite loci at high fidelity as previously described (26,27). Digital Sequencing platform is an NGS panel of cancer-related genes utilizing high-quality sequencing of cell-free DNA (which could comprise circulating tumor DNA) isolated from a simple, non-invasive blood draw. Digital Sequencing employs pre-sequencing preparation of a digital library of individually tagged cfDNA molecules combined with post-sequencing bioinformatic reconstruction to eliminate nearly all false positives.

Figure 6B:
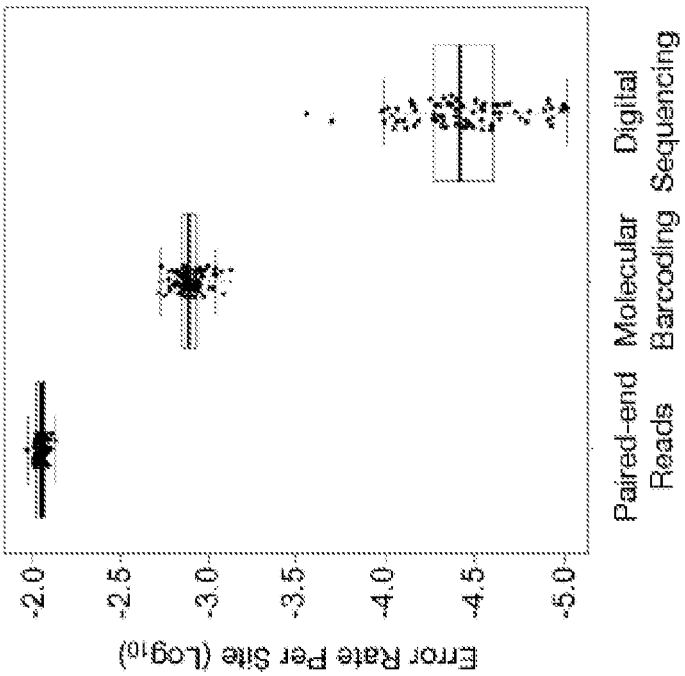

Among these high background error repeats, Digital Sequencing was associated with 100-fold reduction in per-molecule sequencing error relative to standard sequencing approaches (FIG. 6B), allowing efficient and accurate reconstruction of microsatellite sequences of individual unique molecules present in the original patient blood sample. Site-specific and aggregate sample-level MSI status determination thresholds were then established using permutation-based threshold simulations of healthy donor samples. When these per-site and per sample thresholds were combined with the effects of Digital Sequencing correction, the per-sample false positive rate was estimated to be ~10-7.3. Additionally, titration simulations adjusted for the distribution of clinical inputs predicted robust MSI detection to ~0.2% tumor fraction, with a marked decline in detection efficiency thereafter. As such, samples with a circulating tumor fraction (as defined by the maximum somatic variant allele fraction) of <0.2% were considered unevaluable for MSI status.

2. Analytical Validation Studies

Figure 7A:
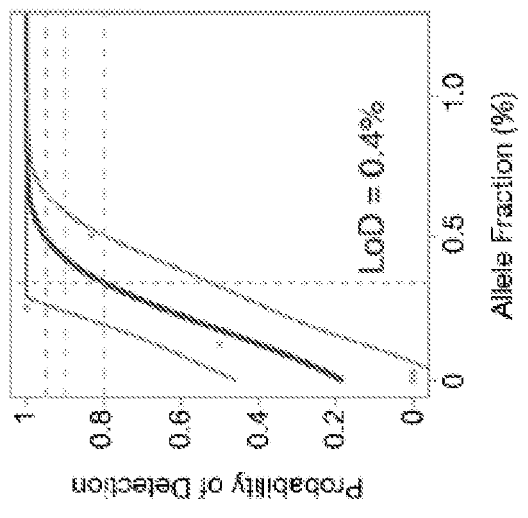
FIGS. 7A-7C are plots showing analytical validation of ctDNA MSI detection. Observed MSI detection rate was plotted by titration level (grey dots), and probit regression was used to determine the 95% limit of detection for 5 ng (FIG. 7A) and 30 ng (FIG. 7B) cfDNA inputs.
Figure 7B:
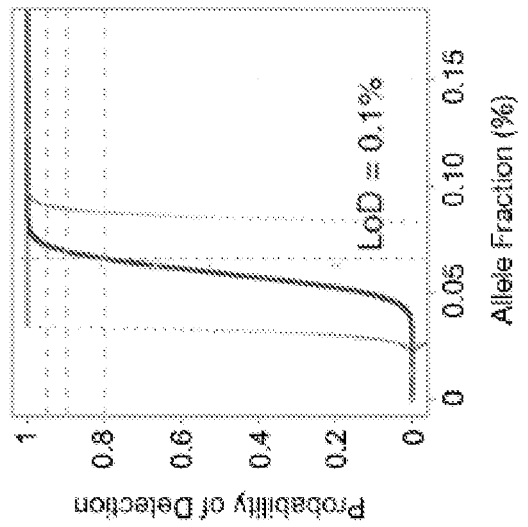

To assess the analytical sensitivity of MSI detection, cfDNA derived from the supernatant of the MSI-H cell line KM12 was diluted into MSS cfDNA targeting five titration points comprising 15 independently processed replicates bracketing the limit of detection (LoD) predicted by the in silico simulations described above. Each titration series was analyzed at both 5 ng, the minimum acceptable cfDNA input, and 30 ng, the maximum and most common cfDNA input. Using probit analysis, the 95% LoD (LOD95) was calculated to be 0.4% at 5 ng input (FIG. 7A) and 0.1% at 30 ng input (FIG. 7B).

Figure 7C:
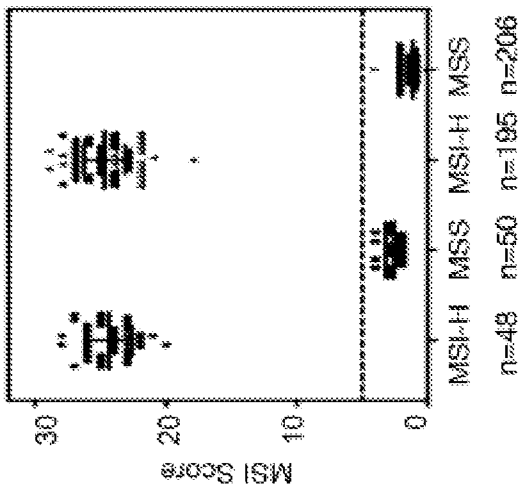
Figure 8:
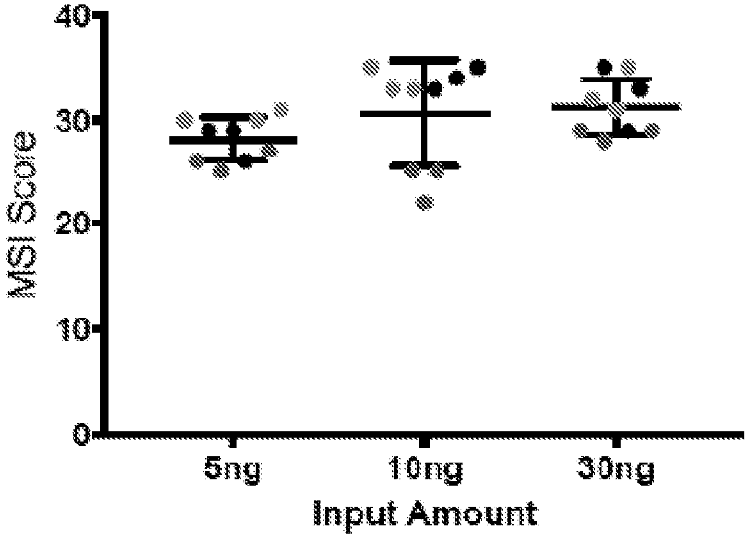
FIG. 8 is a plot showing precision studies using a contrived sample at three input levels (5, 10, and 30 ng) processed in triplicate within run and between runs. Each greyscale shade represents a different run.

To assess analytical intermediate precision, replicates of four different contrived materials were analyzed, two MSS and two MSI-H (FIG. 7C). Across 499 replicates, categorical concordance for MSI status was 100% (499/499, 95% CI 99-100%), with coefficients of variation for quantitative MSI score ranging from 6.3-7.2% for MSI-H samples (Table 3). Repeatability and input robustness were also assessed by replicate testing of MSS and MSI-H contrived material at 5 ng, 10 ng, and 30 ng cfDNA input, which similarly demonstrated 100% concordance (27/27, 95% CI 85-100%, FIG. 8 and Table 4). Clinical precision was confirmed in 72 independent patient sample replicates representing a range of MSI scores and tumor fractions processed across three independent batches, days, operators, and reagent lots, which demonstrated a qualitative concordance of 100% (72/72, 95% CI 94-100%) with coefficients of variation for the underlying quantitative MSI score of 2.0-15.2% (Table 5).

TABLE 3

| controlLot | mean MSI score | % cv | count |
|---|---|---|---|
| A | 24.4 | 7.2 | 48 |
| B | 2.6 | 25.2 | 50 |
| C | 1.1 | 35.5 | 195 |
| D | 24.7 | 6.3 | 206 |

TABLE 4

| Input amount | Mean | Stdev | % cv |
|---|---|---|---|
| 5 ng | 28.1 | 2.1 | 7.6 |
| 10 ng | 30.6 | 5.1 | 16.5 |
| 30 ng | 32.0 | 3.0 | 9.2 |

TABLE 5

| Sample Number | max MAF | Categorical call | Between run replicates (n) | Concordance (%) | Within run replicates (n) | Concordance (%) | avg MSI score | % CV |
|---|---|---|---|---|---|---|---|---|
| 1 | 2.6 | MSI-H | 3 | 100 | 3 | 100 | 8 | 10.7 |
| 2 | 2.2 | MSI-H | 3 | 100 | 3 | 100 | 18 | 6.5 |
| 3 | 2.0 | MSS | 3 | 100 | 3 | 100 | 0 | n/a (score = 0/1) |
| 4 | 1.2 | MSI-H | 3 | 100 | 3 | 100 | 14 | 15.2 |
| 5 | 2.5 | MSS | 3 | 100 | 3 | 100 | 0 | n/a (score = 0/1) |
| 6 | 3.4 | MSS | 3 | 100 | 3 | 100 | 0 | n/a (score = 0/1) |

TABLE 5-continued

| Sample Number | max MAF | Categorical call | Between run replicates (n) | Concordance (%) | Within run replicates (n) | Concordance (%) | avg MSI score | % CV |
|---|---|---|---|---|---|---|---|---|
| 7 | 33.4 | MSS | 3 | 100 | 3 | 100 | 0 | n/a (score = 0/1) |
| 8 | 0 | MSS | 3 | 100 | N/A | N/A | 0 | n/a (score = 0/1) |
| 9 | 27.95 | MSS | N/A | N/A | 3 | 100 | 0 | n/a (score = 0/1) |
| 10 | 2.01 | MSS | 3 | 100 | 3 | 100 | 0 | n/a (score = 0/1) |
| 11 | 62.7 | MSS | 3 | 100 | 3 | 100 | 0 | n/a (score = 0/1) |
| 12 | 37.8 | MSI-H | 3 | 100 | 3 | 100 | 28 | 2.0 |
| 13 | 17.1 | MSS | 3 | 100 | 3 | 100 | 0 | n/a (score = 0/1) |

To assess analytical specificity, healthy donor plasma samples (distinct from those used in training), MSS contrived materials, and MSS patient samples were analyzed for spurious MSI-H calls. Analytical specificity was 100% across healthy donor samples (20/20, 95% CI 83-100%), contrived material (245/245, 95% CI 98-100%), and patient samples (48/48, 95% CI 92-100%).

3. Clinical Validation Studies

Figure 9:
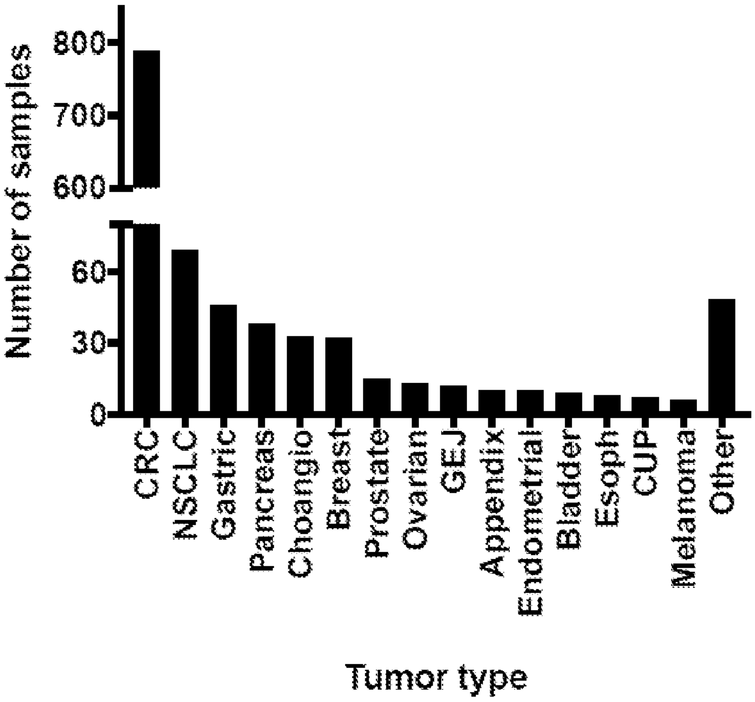
FIG. 9 is a plot showing tumor types represented in a clinical validation cohort. In particular, shown are only the tumor types with at least 5 representative samples. All others (n=25 distinct tumor types) are grouped in the "Other" category.

As no orthogonal cfDNA-based method was available to use as a comparator, clinical accuracy was determined by comparing ctDNA MSI assessment to MSI status from the medical record determined using standard-of-care tissue testing (a mixture of IHC, PCR, and NGS methods) for 1145 samples comprising 40 distinct cancer types, 15 of which had at least 5 representative specimens (FIG. 9). In 949 unique evaluable patients, ctDNA detected 87% of patients reported as MSI-H (71/82, 95% CI 77-93%) and 99.5% of patients reported as MSS/MSI-L (863/867, 95% CI 98.7-99.8%) for an overall accuracy of 98.4% (934/949, 95% CI 97.3-99.1%), with a positive predictive value (PPV) of 95% (71/75, 95% CI 86-98%) (FIG. 10C, Table 8). Consistent with in silico modeling studies, MSI-H detection was rare (0/19) in samples classified as unevaluable due to low tumor fraction (FIG. 10A), which explained 57% (16/28) of the observed ctDNA-tissue discordance in the total unique patient sample set (Tables 6-9). For samples with tumor fractions above 1%, ctDNA PPA rose to 93% (54/58, 95% CI 82-98%, Table 9).

TABLE 6

A. All samples regardless of max VAF

| | | Tissue MSI PCR/IHC/NGS | | |
|---|---|---|---|---|
| | | MSI-H | MSS | PPV/NPV |
| cfDNA MSI | MSI-H | 71 | 4 | 94.7% |
| | MSS | 28 | 1042 | 97.4% |
| Sensitivity (PPA)/Specificity (NPA) | | 71.7% | 99.6% | 1145 (total) |

TABLE 7

B. Tumor not detected excluded

| | | Tissue MSI PCR/IHC/NGS | | |
|---|---|---|---|---|
| | | MSI-H | MSS | PPV/NPV |
| cfDNA MSI | MSI-H | 71 | 4 | 94.7% |
| | MSS | 14 | 947 | 98.5% |
| Sensitivity (PPA)/Specificity (NPA) | | 83.5% | 99.6% | 1036 (total) |

TABLE 8

C. Max VAF ≥0.2%

| | | Tissue MSI PCR/IHC/NGS | | |
|---|---|---|---|---|
| | | MSI-H | MSS | PPV/NPV |
| cfDNA MSI | MSI-H | 71 | 4 | 94.7% |
| | MSS | 11 | 863 | 98.7% |
| Sensitivity (PPA)/Specificity (NPA) | | 86.6% | 99.5% | 949 (total) |

TABLE 9

D. Max VAF ≥1%

| | | Tissue MSI PCR/IHC/NGS | | |
|---|---|---|---|---|
| | | MSI-H | MSS | PPV/NPV |
| cfDNA MSI | MSI-H | 54 | 3 | 94.7% |
| | MSS | 4 | 690 | 99.4% |
| Sensitivity (PPA)/Specificity (MPA) | | 93.1% | 99.6% | 751 (total) |

Interestingly, despite the high correlation between IHC and PCR tissue tests reported in the literature (23,35), concordance between ctDNA and tissue MSI status here varied by tissue test methodology (97.4% by PCR (450/462), 98.0% by NGS (239/244), and 83.0% by IHC (93/

112), FIG. 10B and Tables 10 and 11). On further investigation, it was noted that this discordance was due to both an increased tissue IHC-positive, ctDNA-negative population (2.4% by PCR, 2.0% by NGS, and 12.5% by IHC, Fisher exact test p<0.001 for IHC-PCR and IHC-NGS) and an increased tissue IHC-negative, ctDNA-positive population (0.2% by PCR, 0% by NGS, and 4.5% by IHC, Fisher exact test p<0.01 for both comparisons). These discrepancies led us to investigate whether IHC limitations may be contributing to the observed IHC-ctDNA discordance rather than compromised ctDNA accuracy. Of the 25 samples for which IHC and another tissue test result were available, 12 demonstrated IHC-ctDNA discordance. Importantly, PCR and/or NGS tissue testing supported the ctDNA NGS results rather than the tissue IHC in 5 of 12 discordances. Together, these data support previous report that IHC may not be as reliable in MSI determination as the PCR diagnostic archetype (36).

TABLE 10

| A. All samples | | | | |
|---|---|---|---|---|
| Tissue | cfDNA | PCR | NGS | IHC |
| Negative | Negative | 408 | 226 | 78 |
| Positive | Positive | 42 | 13 | 15 |
| Positive | Negative | 11 | 5 | 14 |
| Negative | Positive | 1 | 0 | 5 |
| | Total | 462 | 244 | 112 |

TABLE 11

| B. Evaluable | | | | |
|---|---|---|---|---|
| Tissue | cfDNA | PCR | NGS | IHC |
| Negative | Negative | 353 | 179 | 64 |
| Positive | Positive | 42 | 13 | 15 |
| Positive | Negative | 5 | 2 | 5 |
| Negative | Positive | 1 | 0 | 5 |
| | Total | 401 | 194 | 89 |

4. ctDNA MSI Status in 28,459 Consecutive Advanced Cancer Patients

Figure 11A:
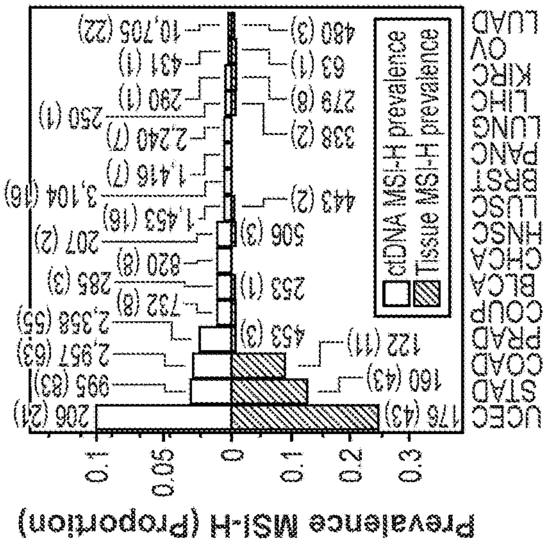
FIGS. 11A-11C are plots showing ctDNA MSI landscape across 28,459 clinical samples.

Although a number of studies have assessed the prevalence of MSI across different tumor types in tissue (13,32, 37), to date there is no published landscape analysis of ctDNA MSI status across cancer types. To this end, the MSI algorithm described above was applied to 28,459 consecutive advanced cancer patient clinical samples tested in the Guardant Health Clinical Laboratory. In this cohort, 278 samples (tumor fraction median of 6.55%, range 0.09%-89%) comprising 16 different tumor types were identified as MSI-H by ctDNA, which corresponds to an overall pan-cancer prevalence of ~1%, similar to that previously reported for tissue (13,32,37). Similarly, MSI-H prevalence among tumor types also closely reflected that observed in tissue-based analyses (FIG. 11A); as expected, MSI-H was most prevalent in endometrial, colorectal, and gastric cancers, whereas other tumors such as lung, bladder, and head and neck cancers demonstrated lower prevalence. Specific exceptions to previous MSI-H prevalence estimates included marginally lower prevalence in endometrial, colorectal, and gastric cancers, and marginally higher prevalence in prostate cancer.

Figure 11B:
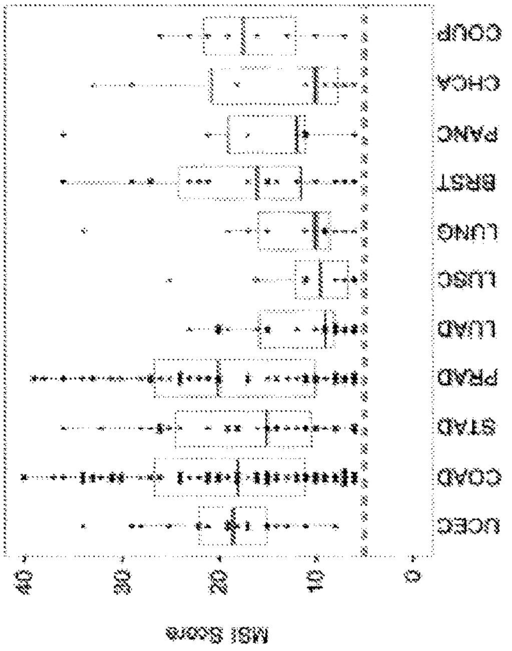
Figure 11C:
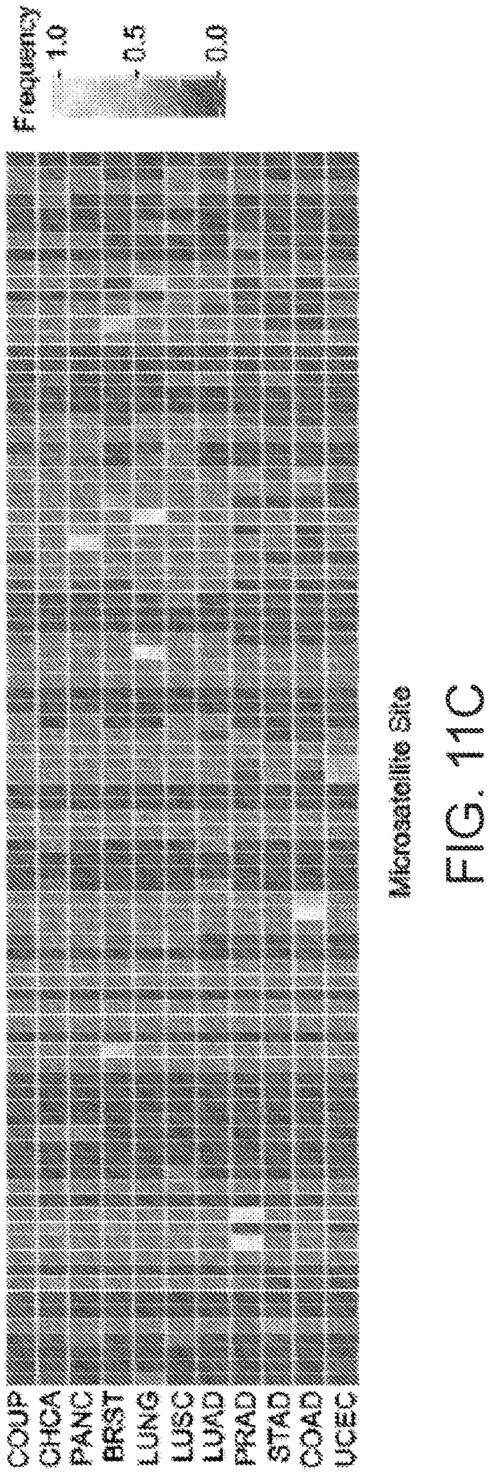

Given the pan-solid tumor nature of the ctDNA intended use population and immunotherapy approval for MSI-H tumors, microsatellite loci for this panel were intentionally selected to be informative of MSI status across all solid tumor types. Consistent with this design intent, analysis of sample- and locus-level MSI score distributions—i.e., MSI score and site score respectively (FIGS. 11B and 11C) demonstrated consistent performance across tumor types, with MSI-H samples demonstrating signal substantially above threshold. Moreover, the diagnostic yield of MSI assessment outside of the tumor types for which MSI is commonly tested was substantial; more than half of the identified cases (143/278) occurred in tumor types in which MSI testing is very uncommon and thus identified patients that would otherwise never have been tested.

Figure 12A:
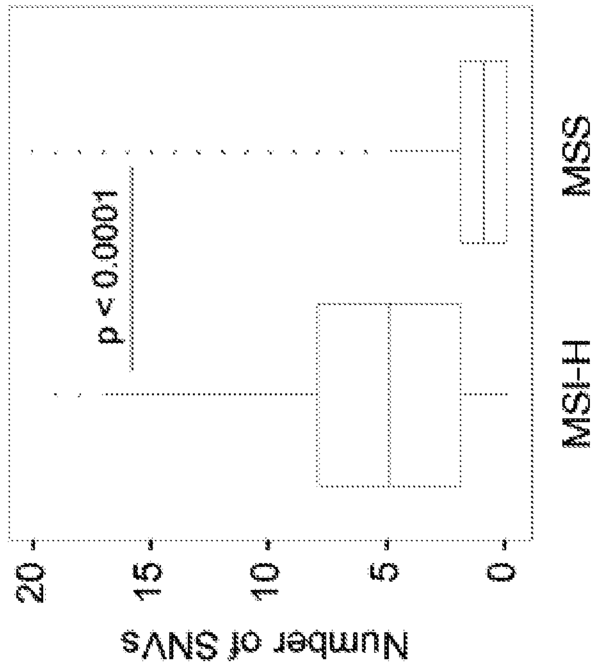
FIGS. 12A and 12B are plots showing tumor mutation burden by MSI status. Number of single nucleotide variants (SNVs) (FIG. 12A) and indels (FIG. 12B) detected per sample categorized by MSI status across 278 MSI-H and 28,181 MSS samples.
Figure 12B:
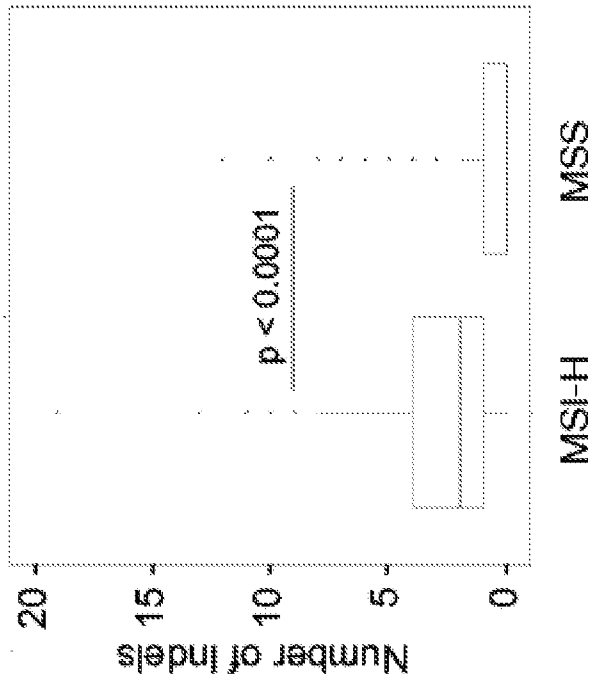

Consistent with what has been reported in tissue (38), the number of indels and SNVs (inclusive of non-synonymous and synonymous variants) is significantly increased in MSI-H samples relative to those characterized as having MSS status (FIG. 12). Specifically, the median number of SNVs in MSI-H samples was 6.3 vs 1.4 in MSS (Chi-squared p<0.0001) and the median number of indels in MSI-H samples was 2.6 vs 0.4 in MSS (Chi-squared p<0.0001).

5. ctDNA MSI Status Predicts Immunotherapy Response

Figure 13A:
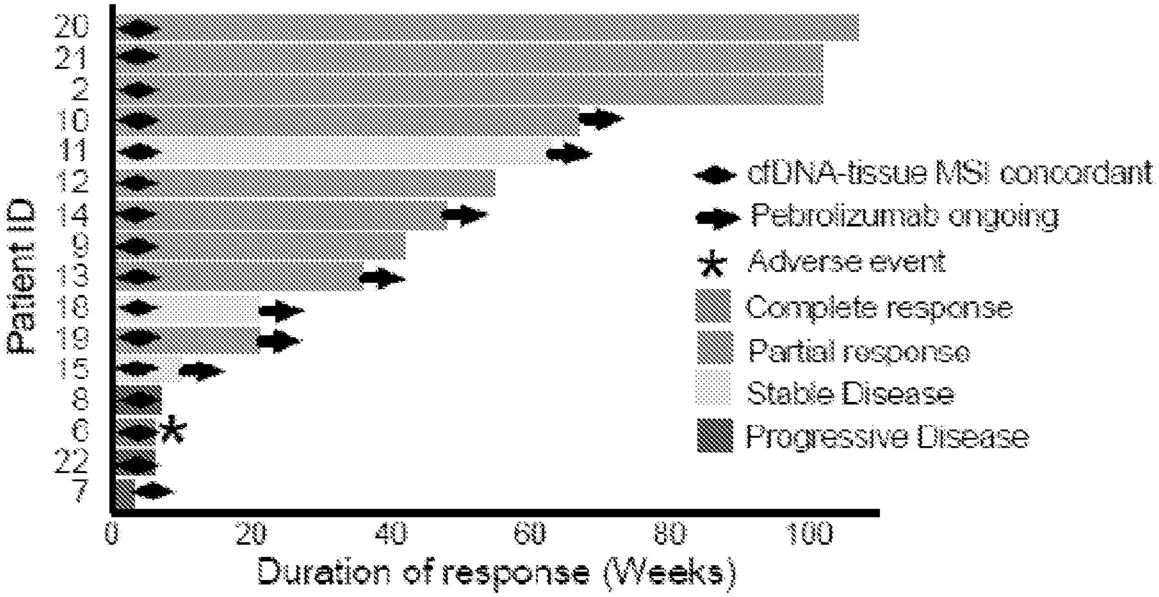
FIGS. 13A-13E show clinical outcome data to immune checkpoint blockade (ICB) therapy in ctDNA MSI-H patients.
Figure 13B:
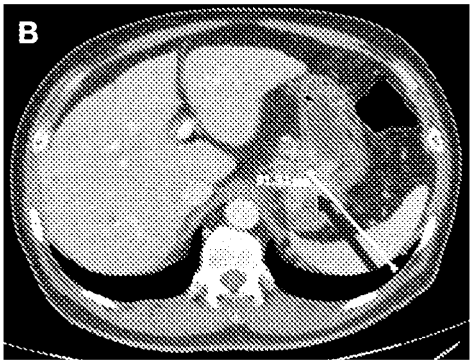
Figure 13C:
Figure 13D:
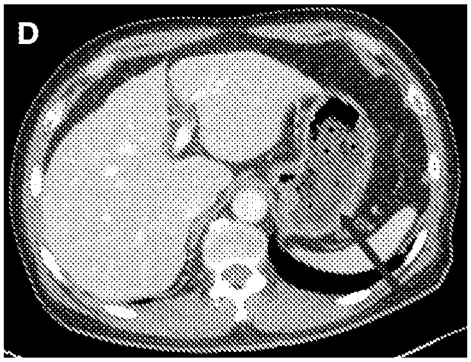
Figure 13E:
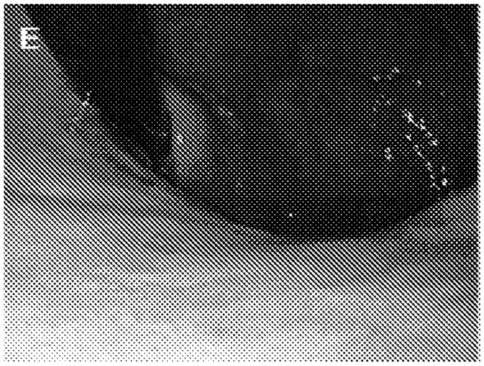

The most salient utility of MSI status today is its ability to select patients for immunotherapy. Despite this and the barriers to obtaining tissue in many patients, the ability of ctDNA MSI status to predict response to immunotherapy has not been reported. To establish clinical validity for this biomarker, we present clinical outcomes for 16 ctDNA MSI-H metastatic gastric cancer patients treated with pembrolizumab (n=15) or nivolumab (n=1) after the failure of standard of care chemotherapy in a phase II pembrolizumab trial in gastric cancer (NCT #02589496). cfDNA and tissue PCR MSI assessment in pre-treatment samples was 100% concordant for MSI-H (16/16, 95% CI 76-100%). Ten of 16 patients achieved either complete (n=3) or partial (n=7) investigator assessed objective response by RECIST 1.1 criteria, with an additional three patients with stable disease (FIG. 13A), for an objective response rate of 63% (10/16, 95% CI 36-84%) and a disease control rate of 81% (13/16, 95% CI 54-95%), similar to responses previously reported for MSI-H patients defined by tissue testing (39). Importantly, even in this pretreated population, these responses were durable, with a median duration of treatment of 39 weeks. Indeed, Patient 21, for example, experienced complete regression of disease following pembrolizumab treatment after failure of fluoropyrimidine/platinum chemotherapy and is still disease-free more than 6 months following completion of 35 cycles of therapy (FIGS. 13B-13E).

Discussion

A novel cfDNA-based targeted NGS approach was validated for MSI detection-by using a large panel of microsatellites, this approach achieved high sensitivity relative to tissue-based methods, while maintaining very high specificity. Plasma-detected prevalences of MSI-H across 16 common solid tumors were similar to published tissue-based compendia demonstrating pan-tumor performance intended with the MSI detection algorithm design. Furthermore, clinical utility was demonstrated by showing that MSI-H patients as detected by cfDNA benefit from ICB therapy in a manner similar to that reported for tissue-defined populations (39), expanding the availability of MSI detection to all patients regardless of tissue availability or requirement to undergo invasive tissue acquisition procedures.

This example demonstrates robust analytical performance for MSI detection on a ctDNA panel previously validated for detection of the other four variant types in all guideline-recommended indications (26). In particular, the analytical sensitivity for MSI detection in contrived samples demonstrated reproducible detection to 0.1%, congruent with previous reports of similar sensitivity for indels and SNVs (26). Importantly, this example assessed the performance of ctDNA MSI testing in 1145 samples with orthogonal tissue MSI, which constitutes the largest ctDNA-tissue MSI concordance cohort yet described. Relative to standard-of-care tissue MSI testing for the same patients, ctDNA MSI assessment demonstrated high PPV (95%), which compares favorably to the reported PPV of 90-92% reported for local vs. central tissue-based MSI assessment (36), and high PPA (87%) in the evaluable population, which is consistent with previous studies examining concordance of plasma and tissue genotyping for other variant types (25,26,45,46). Factors that can contribute to incomplete concordance may include tumor heterogeneity, differential shedding by the primary vs. metastatic lesions, temporal discordance of tissue and plasma collection, and low tumor shedding by some tumors (40,44,47-49). Interestingly, a gastric cancer patient identified as MSI-H by plasma and by pentaplex PCR in this report was previously reported to comprise discrete tumor populations of MSS and MSI-H disease as assessed by both IHC and PCR performed on tissue (40). The same study found 9% discordance for MSI-H between paired tissue biopsies in the same patient (40), highlighting the potential contribution of intratumoral heterogeneity to discordances in MSI status. Moreover, the observation of non-trivial discordance between PCR and IHC tissue methods in this report highlight the importance of accurate MSI testing, which has been reported as a primary source of ICB failure (36). Consistent with the challenges presented by tissue genotyping in advanced solid tumors, a study in metastatic non-small cell lung cancer (NSCLC) has shown that relative to tissue, plasma-based testing increases the number of patients with successful tumor genotyping results, as well as the frequency of detecting targetable mutations while returning results at least a week faster than typical tissue genotyping results (25,45).

This example presents the first ctDNA-based landscape analysis of MSI in a large advanced pan-cancer cohort. Overall, the relative prevalence across tumor types in a set of >28,000 consecutive clinical samples are consistent with what has been reported for tissue (13,32,37), with only marginal differences. For example, the prevalence in CRC and endometrial cancer is lower than what has been reported for tissue (13), which most likely reflects the fact that the tissue-based landscape analyses include large numbers of early stage MSI-H tumors, which have a better prognosis (15) and are less likely to be part of the advanced cancer population tested with ctDNA. On the other hand, the larger than expected prevalence of MSI-H prostate cancer is attributable to increased representation of MSI-H disease in advanced patients; two recent studies focusing on MSI status in advanced prostate cancer have shown MSI-H prevalence of 3.1% and 3.8% in that patient population (50,51), which is similar to our the 2.6% observed in this study. Unsurprisingly, given the design intent for pan-cancer MSI detection, landscape analysis did not reveal tumor type-specific patterns of microsatellite instability. However, this does not preclude the possibility that in plasma, similar to what has been shown in tissue (37,52), tumor-type specific patterns could emerge with the assessment of a larger number of microsatellite loci and larger numbers of representative MSI-H samples.

The clinical outcomes reported here are limited to gastric cancer; nevertheless, the observed objective response rate is consistent with expectations from tissue-based studies, suggesting that ICB treatment based on cfDNA MSI results should achieve expected outcomes across solid tumor types. Additionally, lack of germline dMMR data prevented conclusions about familial implications for cfDNA-detected MSI. Lastly, treatment data were not available for the majority of patients with cfDNA-/tissue+discordance, but it is expected that at least some have received ICB therapy based on the tumor result, which may suppress MSI-H disease and lead to lack of MSI detection by cfDNA. As such, the 87% sensitivity for MSI-H detection relative to tissue may be higher in patients who are treatment-naïve or not receiving therapy. Future studies should be pursued to address these questions.

In summary, a cfDNA-based targeted NGS panel has been developed and validated that accurately assesses MSI status while also providing comprehensive tumor genotyping, allowing pan-solid tumor guideline-complete testing from a single peripheral blood draw with high sensitivity, specificity and precision. Clinical validation using both comparison to tissue testing, population-level prevalence analyses, and the first reported outcomes for cfDNA MSI-H patients treated with ICB therapy supported the clinical accuracy and relevance of this approach. Such simultaneous characterization of MSI status and tumor genotype from a simple peripheral blood draw has the potential to expand access to both targeted therapy and immunotherapies to all advanced cancer patients including those for whom current tissue-based testing paradigms are inadequate.

REFERENCES

1. Koh W-J, Abu-Rustum N R, Bean S, Bradley K, Campos S M, Cho K R, et al. Cervical Cancer, Version 3.2019, NCCN Clinical Practice Guidelines in Oncology. J Natl Compr Canc Netw. 2019; 17:64-84.
2. Benson, Al B., D'Angelica, Michael I., Abbott, Daniel E., Abrams, Thomas A., Alberts, Steven R., Anaya, Daniel A., et al. Hepatobiliary Cancers, Version 4.2018: Featured Updates to the NCCN Guidelines. National Comprehensive Cancer Network Clinical Practice Guidelines in Oncology [Internet]. 2018; Available from: https://www.nccn.org/professionals/physician_gls/pdf/hepatobiliary.pdf.
3. Benson, Al B., Venook, Alan P., Bekaii-Saab, Tanios, Chan, Emily, Chen, Yi-Jen, Cooper, Harry S., et al. Colon Cancer Version 1.2016, NCCN Practice Guidelines in Oncology. 2015; Available from: https://www.nccn.org/professionals/physician_gls/pdf/colorectal.pdf.
4. Koh W-J, Abu-Rustum N R, Bean S, Bradley K, Campos S M, Cho K R, et al. Uterine Neoplasms, Version 1.2018, NCCN Clinical Practice Guidelines in Oncology. J Natl Compr Canc Netw. 2018;16:170-99.
5. Ajani, Jaffer A., D'Amico, Thomas A., Baggstrom, Maria, Bentrem, David J., Chao, Joseph, Das, Prajnan, et al. Esophageal and Esophagogastric Junction Cancers Version 4.2017. 2017; Available from: https://www.nccn.org/professionals/physician_gls/pdf/esophageal.pdf.
6. Ajani, Jaffer A., D'Amico, Thomas A., Baggstrom, Maria, Bentrem, David J., Chao, Joseph, Das, Prajnan, et al. Gastric Cancer, Version 5.2017, NCCN Clinical Practice Guidelines in Oncology. 2017; Available from: https://www.nccn.org/professionals/physician_gls/pdf/gastric.pdf.
7. Armstrong, Deborah K., Alvarez, Ronald D., Bakkum-Gamez, Jamie N., Barroilhet, Lisa, Behbakht, Kian, Berchuck, Andrew, et al. NCCN Guidelines Version 1.2019 Ovarian Cancer. 2019; Available from: https://www.nccn.org/professionals/physician_gls/pdf/ovarian.pdf.
8. Tempero, Margaret A., Malafa, Mokenge P., Al-Hawary, Mahmoud, Asbun, Horacio, Bain, Andrew, Behrman, Stephen W., et al. Pancreatic Adenocarcinoma Version 2.2018, NCCN Clinical Practice Guidelines in Oncology. 2018; Available from: httpshttps://www.nccn.org/professionals/physician_gls/pdf/pancreatic.pdf.
9. Mohler JL, Lee R J, Antonarakis E S, Armstrong A J, D'Amico A V, Davis B J, et al. NCCN Guidelines Version 1.2018 Prostate Cancer [Internet]. NCCN Clinical Practice Guidelines in Oncology (NCCN Guidelines). 2018. Available from: https://www.nccn.org.
10. Diaz L A, Le D T. PD-1 Blockade in Tumors with Mismatch-Repair Deficiency. N Engl J Med. 2015;373: 1979.
11. Le D T, Durham J N, Smith K N, Wang H, Bartlett B R, Aulakh LK, et al. Mismatch-repair deficiency predicts response of solid tumors to PD-1 blockade. Science. 2017.
12. Buza N, Ziai J, Hui P. Mismatch repair deficiency testing in clinical practice. Expert Rev Mol Diagn. 2016; 16:591-604.
13. Bonneville R, Krook M A, Kautto E A, Miya J, Wing M R, Chen H-Z, et al. Landscape of Microsatellite Instability Across 39 Cancer Types. JCO Precis Oncol. 2017.
14. Marcus L, Lemery S J, Keegan P, Pazdur R. FDA Approval Summary: Pembrolizumab for the treatment of microsatellite instability-high solid tumors. Clin Cancer Res. 2019.
15. Benson A B, Arnoletti J P, Bekaii-Saab T, Chan E, Chen Y-J, Choti M A, et al. Colon cancer. J Natl Compr Canc Netw. 2011;9:1238-90.
16. Boland C R, Thibodeau S N, Hamilton S R, Sidransky D, Eshleman J R, Burt RW, et al. A National Cancer Institute Workshop on Microsatellite Instability for cancer detection and familial predisposition: development of international criteria for the determination of microsatellite instability in colorectal cancer. Cancer Res. 1998;58:5248-57.
17. Umar A, Boland C R, Terdiman J P, Syngal S, de la Chapelle A, Rüschoff J, et al. Revised Bethesda Guidelines for hereditary nonpolyposis colorectal cancer (Lynch syndrome) and microsatellite instability. J Natl Cancer Inst. 2004;96:261-8.
18. Lu Y, Soong T D, Elemento O. A novel approach for characterizing microsatellite instability in cancer cells. PLOS ONE. 2013;8: e63056.
19. Dudley J C, Lin M-T, Le DT, Eshleman J R. Microsatellite Instability as a Biomarker for PD-1 Blockade. Clin Cancer Res. 2016;22:813-20.
20. Salipante S J, Scroggins S M, Hampel H L, Turner E H, Pritchard C C. Microsatellite instability detection by next generation sequencing. Clin Chem. 2014;60:1192-9.
21. Latham A, Srinivasan P, Kemel Y, Shia J, Bandlamudi C, Mandelker D, et al. Microsatellite Instability Is Associated With the Presence of Lynch Syndrome Pan-Cancer. J Clin Oncol. 2019;37:286-95.
22. Guardant Health, Inc. Tissue Findings Submitted with Guardant360 Test Requisitions-Data on File. Redwood City, California; 2019.
23. Hampel H, Frankel W L, Martin E, Arnold M, Khanduja K, Kuebler P, et al. Screening for the Lynch syndrome (hereditary nonpolyposis colorectal cancer). N Engl J Med. 2005;352:1851-60.
24. Shaikh T, Handorf E A, Meyer J E, Hall M J, Esnaola N F. Mismatch Repair Deficiency Testing in Patients With Colorectal Cancer and Nonadherence to Testing Guidelines in Young Adults. JAMA Oncol. 2017; e173580.
25. Leighl N B, Page R D, Raymond V M, Daniel D B, Divers S G, Reckamp K L, et al. Clinical Utility of Comprehensive Cell-Free DNA Analysis to Identify Genomic Biomarkers in Patients with Newly Diagnosed Metastatic Non-Small Cell Lung Cancer. Clinical Cancer Research. 2019;clincanres.0624.2019.
26. Odegaard J I, Vincent J J, Mortimer S, Vowles J V, Ulrich B C, Banks K C, et al. Validation of a Plasma-Based Comprehensive Cancer Genotyping Assay Utilizing Orthogonal Tissue-and Plasma-Based Methodologies. Clin Cancer Res. 2018;24:3539-49.
27. Lanman R B, Mortimer S A, Zill O A, Sebisanovic D, Lopez R, Blau S, et al. Analytical and Clinical Validation of a Digital Sequencing Panel for Quantitative, Highly Accurate Evaluation of Cell-Free Circulating Tumor DNA. PLOS ONE. 2015;10: e0140712.
28. Akaike H. Information Theory and an Extension of the Maximum Likelihood Principle. In: Petrov BN, Csaki F, editors. Proceedings of the 2nd International Symposium on Information Theory (pp 267-281) Budapest: Akademiai Kiado. 1973.
29. Berg K C G, Eide P W, Eilertsen I A, Johannessen B, Bruun J, Danielsen S A, et al. Multi-omics of 34 colorectal cancer cell lines-a resource for biomedical studies. Mol Cancer. 2017;16:116.
30. Cosmic. COSMIC-Catalogue of Somatic Mutations in Cancer [Internet]. [cited 2019 Apr. 17]. Available from: https://cancer.sanger.ac.uk/cosmic.
31. Forbes S A, Beare D, Boutselakis H, Bamford S, Bindal N, Tate J, et al. COSMIC: somatic cancer genetics at high-resolution. Nucleic Acids Research. 2017;45: D777-83.
32. Hause R J, Pritchard C C, Shendure J, Salipante S J. Classification and characterization of microsatellite instability across 18 cancer types. Nat Med. 2016;22: 1342-50.
33. Georgiadis A, Wood D, Murphy D, Parpart-Li S, Riley D, Sengamalay N, et al. Abstract 1286: Analytical validation of an integrated next-generation sequencing pan-cancer liquid biopsy approach for detection of microsatellite instability. Cancer Res. 2018;78:1286.
34. Zill O A, Banks K C, Fairclough S R, Mortimer S A, Vowles J V, Mokhtari R, et al. The Landscape of Actionable Genomic Alterations in Cell-Free Circulating Tumor DNA from 21,807 Advanced Cancer Patients. Clin Cancer Res. 2018;24:3528-38.
35. Lindor N M, Burgart L J, Leontovich O, Goldberg R M, Cunningham J M, Sargent D J, et al. Immunohistochemistry versus microsatellite instability testing in phenotyping colorectal tumors. J Clin Oncol. 2002;20: 1043-8.

36. Cohen R, Hain E, Buhard O, Guilloux A, Bardier A, Kaci R, et al. Association of Primary Resistance to Immune Checkpoint Inhibitors in Metastatic Colorectal Cancer With Misdiagnosis of Microsatellite Instability or Mismatch Repair Deficiency Status. JAMA Oncology. 2019;5:551.
37. Vanderwalde A, Spetzler D, Xiao N, Gatalica Z, Marshall J. Microsatellite instability status determined by next-generation sequencing and compared with PD-L1 and tumor mutational burden in 11,348 patients. Cancer Medicine. 2018;7:746-56.
38. Bonneville R, Krook M A, Kautto E A, Miya J, Wing M R, Chen H-Z, et al. Landscape of Microsatellite Instability Across 39 Cancer Types. JCO Precis Oncol. 2017;2017.
39. Le D T, Uram J N, Wang H, Bartlett B R, Kemberling H, Eyring A D, et al. PD-1 Blockade in Tumors with Mismatch-Repair Deficiency. New England Journal of Medicine. 2015;372:2509-20.
40. Kim S T, Cristescu R, Bass A J, Kim K-M, Odegaard J I, Kim K, et al. Comprehensive molecular characterization of clinical responses to PD-1 inhibition in metastatic gastric cancer. Nat Med. 2018;24:1449-58.
41. Accordino M K, Wright J D, Buono D, Neugut A I, Hershman D L. Trends in use and safety of image-guided transthoracic needle biopsies in patients with cancer. J Oncol Pract. 2015;11: e351-359.
42. Lokhandwala T, Bittoni M A, Dann R A, D'Souza A O, Johnson M, Nagy R J, et al. Costs of Diagnostic Assessment for Lung Cancer: A Medicare Claims Analysis. Clin Lung Cancer. 2017; 18: e27-34.
43. De Mattos-Arruda L, Weigelt B, Cortes J, Won H H, Ng C K Y, Nuciforo P, et al. Capturing intratumor genetic heterogeneity by de novo mutation profiling of circulating cell-free tumor DNA: a proof-of-principle. Ann Oncol. 2014;25:1729-35.
44. Goyal L, Saha S K, Liu L Y, Siravegna G, Leshchiner I, Ahronian L G, et al. Polyclonal Secondary FGFR2 Mutations Drive Acquired Resistance to FGFR Inhibition in Patients with FGFR2 Fusion-Positive Cholangiocarcinoma. Cancer Discov. 2017;7:1-12.
45. Aggarwal C, Thompson J C, Black T A, Katz SI , Fan R, Yee S S, et al. Clinical Implications of Plasma-Based Genotyping With the Delivery of Personalized Therapy in Metastatic Non-Small Cell Lung Cancer. JAMA Oncol. 2018.
46. Siravegna G, Lazzari L, Crisafulli G, Sartore-Bianchi A, Mussolin B, Cassingena A, et al. Radiologic and Genomic Evolution of Individual Metastases during HER2 Blockade in Colorectal Cancer. Cancer Cell. 2018;34:148-162.e7.
47. Pectasides E, Stachler MD, Derks S, Liu Y, Maron S, Islam M, et al. Genomic Heterogeneity as a Barrier to Precision Medicine in Gastroesophageal Adenocarcinoma. Cancer Discov. 2018;8:37-48.
48. Thompson J C, Yee S S, Troxel A B, Savitch S L, Fan R, Balli D, et al. Detection of Therapeutically Targetable Driver and Resistance Mutations in Lung Cancer Patients by Next-Generation Sequencing of Cell-Free Circulating Tumor DNA. Clin Cancer Res. 2016; 22:5772-82.
49. Sacher A G, Komatsubara K M, Oxnard G R. Application of plasma genotyping technologies in non-small cell lung cancer: a practical review. J Thorac Oncol. 2017.
50. Mayrhofer M, De Laere B, Whitington T, Van Oyen P, Ghysel C, Ampe J, et al. Cell-free DNA profiling of metastatic prostate cancer reveals microsatellite instability, structural rearrangements and clonal hematopoiesis. Genome Med. 2018;10:85.
51. Abida W, Armenia J, Gopalan A, Brennan R, Walsh M, Barron D, et al. Prospective Genomic Profiling of Prostate Cancer Across Disease States Reveals Germline and Somatic Alterations That May Affect Clinical Decision Making. JCO Precision Oncology. 2017;1-16.
52. Hause R J, Pritchard C C, Shendure J, Salipante S J. Classification and characterization of microsatellite instability across 18 cancer types. Nature Medicine. 2016;22:1342-50.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, systems, computer readable media, and/or component features, steps, elements, or other aspects thereof can be used in various combinations.

All patents, patent applications, websites, other publications or documents, accession numbers and the like cited herein are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number, if applicable. Likewise if different versions of a publication, website or the like are published at different times, the version most recently published at the effective filing date of the application is meant, unless otherwise indicated.

The invention claimed is:

1. A method, comprising:

(a) obtaining a sample comprising cell-free deoxyribonucleic acids (cfDNA) molecules from a human subject having cancer characterized by microsatellite instability;

(b) preparing a sequencing library by tagging the cfDNA molecules with a plurality of molecular barcodes;

(c) sequencing, via a nucleic acid sequencer, the cfDNA molecules tagged with the plurality of molecular barcodes to generate sequencing reads;

(d) analyzing the sequencing reads to determine the number of different repeat lengths present at each of a plurality of microsatellite loci for the human subject;

(e) generating a plurality of likelihood scores, each of the plurality of likelihood scores comprising each likelihood score comprising a probabilistic log-likelihood score determined from the sequencing reads based on: (i) allele frequency of different repeat lengths and (ii) one or more error modes including a random error mode and a strand-specific error mode, applied to the sequence information;

(f) comparing each of the plurality of likelihood scores to a trained threshold corresponding to each of the plurality of microsatellite loci, wherein the trained threshold is derived from a training dataset comprising sequence information from tumor cfDNA and non-tumor cfDNA samples;

(g) identifying one or more of the plurality of microsatellite loci as unstable based on the comparison of the likelihood score of each of the plurality of microsatellite loci to the trained threshold corresponding to that microsatellite locus;

(h) generating an instability score based on the amount of identified unstable microsatellite loci in the plurality of microsatellite loci;

(i) classifying the sample as being microsatellite unstable in the subject, if the instability score exceeds a population trained threshold for the plurality of microsatellite loci, the population trained threshold having been derived from the training dataset; and (j) administering at least one immunotherapy to the subject after classifying the sample as being microsatellite unstable, wherein the at least one immunotherapy comprises at least one of:

an immune checkpoint molecule, an antibody specific for an antigen selected from the group consisting of: PD-I, PD-2, PD-L1, PD-L2, CTLA-4, OX40, B7.1, B7He, LAG3, CD137,KIR, CCR5, CD27, CD40, and CD47, proinflammatory cytokine selected from the group consisting of: IL-IP, IL-6, and TNF-α, and activated T-cells, thereby treating the cancer in the human subject.

2. The method of claim 1, wherein the likelihood score is a probabilistic log likelihood-based score.

3. The method of claim 1, wherein the trained threshold corresponding to each of the plurality of microsatellite loci is the maximum value of a site score for a microsatellite locus to be classified as stable.

4. The method of claim 1, wherein the likelihood score comprises strand specific error parameter, random error parameter, or both.

5. The method of claim 4, wherein the random error parameter comprises one or more of: a rate of read-level errors where a microsatellite length observed within a sequencing read is one repeat unit longer than an expected microsatellite length, and a rate of read-level errors where a microsatellite length observed within a sequencing read is one repeat unit shorter than an expected microsatellite length.

6. The method of claim 4, wherein the strand specific error parameter comprises one or more of: a rate of strand-level errors where an expected microsatellite length of a sense strand is one repeat unit longer than an expected microsatellite length, a rate of strand-level errors where an expected microsatellite length of an antisense strand is one repeat unit longer than an expected microsatellite length, a rate of strand-level errors where an expected microsatellite length of a sense strand is one repeat unit shorter than an expected microsatellite length, and a rate of strand-level errors where an expected microsatellite length of an antisense strand is one repeat unit shorter than an expected microsatellite length.

7. The method of claim 1, comprising generating a trained threshold for each of the plurality of microsatellite loci by training on sequence information from a population of microsatellite loci in one or more training DNA samples, generating a population trained threshold by training on sequence information from a population of microsatellite loci in one or more training DNA samples, or both.

8. The method of claim 7, wherein the one or more training DNA samples, comprises at least one of: (a) non-tumor cfDNA samples, and (b) DNA samples from one or more tumor types.

9. The method of claim 1, further comprising classifying the instability score as high if the number of unstable microsatellite loci comprises about 0.1%, about 1%, about 2%, about 3%, about 4%, about 5%, about 10%, about 15%, about 20%, or about 25% of the plurality of the microsatellite loci.

10. The method of claim 1, wherein the immune checkpoint molecule comprises an inhibitory molecule that reduces a signal involved in the T cell response to antigen.

11. The method of claim 1, wherein the immune checkpoint molecule comprises at least one of CTLA4, PD-I, PD-LI, PD-L2, CTLA4, CD80, CD86, lymphocyte activation gene 3 (LAG3), killer cell immunoglobulin like receptor (KIR), T cell membrane protein 3 (TIM3), galectin 9 (GAL9), or adenosine A2a receptor (A2aR).

12. The method of claim 1, wherein the human subject is afflicted with breast, colon or lung cancer.

13. The method of claim 1, further comprising:

decoding, from the sequencing reads generated by the nucleic-acid sequencer, barcode- identifier strings corresponding to the plurality of molecular barcodes attached to the cfDNA molecules; and storing, in a computer memory, data records comprising each of the barcode-identifier strings and one or more sequencing reads associated with that barcode-identifier string, wherein sequencing reads having a common barcode-identifier string are organized as a family of sequence reads corresponding to a single cfDNA molecule.

14. The method of claim 13, further comprising modifying the data records stored in the computer memory by adding, for each data record corresponding to a family of sequence reads, a data field containing consensus nucleotide(s) or a complete consensus sequence derived from the sequences of family members to generate augmented data records that include both a corresponding barcode-identifier string of the barcode-identifier strings and the derived consensus sequence for the cfDNA molecule represented by the family of sequence reads.

15. The method of claim 14, further comprising linking the augmented data records that share a common barcode-identifier string or common combination of barcodes to define a relational data structure representing the cfDNA molecules of the sample, and accessing the relational data structure to retrieve the consensus sequences associated with selected barcode-identifier strings for analysis of microsatellite loci.

* * * * *

SEQUENCE LISTING

```
Sequence total quantity: 1
SEQ ID NO: 1            moltype = DNA  length = 34
FEATURE                 Location/Qualifiers
source                  1..34
                        mol_type = other DNA
                        organism = synthetic construct
SEQUENCE: 1
cgaggattat tattattatt attattattg cact                  34
```